(12) United States Patent
An Haack et al.

(10) Patent No.: US 12,251,430 B2
(45) Date of Patent: Mar. 18, 2025

(54) COMPOSITIONS AND METHODS FOR TREATING POMPE DISEASE

(71) Applicant: Genzyme Corporation, Cambridge, MA (US)

(72) Inventors: Kristina An Haack, Shanghai (CN); Patrick Finn, Franklin, MA (US); Catherine Wilson, Durham, NC (US)

(73) Assignee: Genzyme Corporation, Cambridge, MA (US)

( * ) Notice: Subject to any disclaimer, the term of this patent is extended or adjusted under 35 U.S.C. 154(b) by 519 days.

(21) Appl. No.: 17/170,667

(22) Filed: Feb. 8, 2021

(65) Prior Publication Data

US 2021/0244803 A1    Aug. 12, 2021

Related U.S. Application Data

(60) Provisional application No. 63/115,975, filed on Nov. 19, 2020, provisional application No. 62/971,930, filed on Feb. 8, 2020.

(51) Int. Cl.
| | | |
|---|---|---|
| *A61K 39/395* | (2006.01) |
| *A61K 9/00* | (2006.01) |
| *A61K 9/16* | (2006.01) |
| *A61K 9/19* | (2006.01) |
| *A61K 31/519* | (2006.01) |
| *A61K 38/47* | (2006.01) |
| *A61K 47/54* | (2017.01) |
| *A61K 47/61* | (2017.01) |
| *A61P 3/00* | (2006.01) |
| *A61K 39/00* | (2006.01) |

(52) U.S. Cl.
CPC ............ *A61K 38/47* (2013.01); *A61K 9/0019* (2013.01); *A61K 9/1617* (2013.01); *A61K 9/1623* (2013.01); *A61K 9/1641* (2013.01); *A61K 9/19* (2013.01); *A61K 31/519* (2013.01); *A61K 39/39516* (2013.01); *A61K 39/3955* (2013.01); *A61K 47/54* (2017.08); *A61K 47/61* (2017.08); *A61P 3/00* (2018.01); *A61K 2039/545* (2013.01); *A61K 2039/55* (2013.01)

(58) Field of Classification Search
None
See application file for complete search history.

(56) References Cited

U.S. PATENT DOCUMENTS

| 7,723,296 | B2 | 5/2010 | Zhu | |
|---|---|---|---|---|
| 8,835,614 | B2 * | 9/2014 | Avila | A61P 3/00 536/18.5 |
| 11,279,725 | B2 * | 3/2022 | Avila | C07H 15/04 |
| 2005/0058634 | A1 | 3/2005 | Zhu | |
| 2006/0228348 | A1 | 10/2006 | Stefano | |
| 2014/0135337 | A1 | 5/2014 | Joseph | |

FOREIGN PATENT DOCUMENTS

| WO | 2008089403 A3 | 7/2008 |
|---|---|---|
| WO | 2010075010 A2 | 7/2010 |
| WO | 2021159092 A1 | 8/2021 |

OTHER PUBLICATIONS

Anjema, K et al. (Sep. 4-7, 2012). "Tetrahydrobiopterin Responsiveness In PKU: Prediction With The 48-Hour Loading Test And Genotype," In Journal Of Inherited Metabolic Disease 35(Suppl. 1):S2, 182 pages.

Bali, D. S. et al. (Feb. 15, 2012, e-pub. Jan. 17, 2012). "Predicting Cross-Reactive Immunological Material (CRIM) Status In Pompe Disease Using GAA Mutations: Lessons Learned From 10 Years Of Clinical Laboratory Testing Experience," In American Journal of Medical Genetics Part C: Seminars in Medical Genetics 160(1):40-49. 18 pages.

Barker, P. C. et al. (Dec. 2010, e-pub. Dec. 1, 2011). "Use Of Cardiac Magnetic Resonance Imaging To Evaluate Cardiac Structure, Function And Fibrosis In Children With Infantile Pompe Disease On Enzyme Replacement Therapy," Molecular Genetics And Metabolism 101(4):332-337.

Burton, B. K. et al. (Jul. 2017). "The Initial Evaluation Of Patients After Positive Newborn Screening: Recommended Algorithms Leading To A Confirmed Diagnosis Of Pompe Disease," Pediatrics 140(Supplement 1):S14-S23.

Chien, Y. H. et al. (2015). "Long-Term Prognosis Of Patients With Infantile-Onset Pompe Disease Diagnosed By Newborn Screening And Treated Since Birth," The Journal Of Pediatrics 166(4):985-991.

Chien, Y. H. et al. (Sep. 2007). "A Review Of Treatment Of Pompe Disease In Infants," Biologics: Targets And Therapy 1(3):195-201.

Chubb, H. et al. (Jul.-Dec. 2012). "The Use Of Z-Scores In Paediatric Cardiology," Annals Of Pediatric Cardiology 5(2):179-184.

Dasouki, M. et al.(2014). "Pompe Disease: Literature Review And Case Series," Neurologic Clinics 32(3):751-776.

De Wilde, F. et al. (1995). "Surgical Treatment Of Myogenic Blepharoptosis," Bull Soc Belge Ophtalmol. 255:139-146.

Figueiredo, M. (Feb. 13, 2020). "Sanofi 's Next-generation ERT Halts Progression of Pompe Disease in Patients, Interim Trial Data Show," Pompe Disease, 8 pages.

Garman, R.D. et al. (2004). "Methotrexate Reduces Antibody Responses To Recombinant Human α-Galactosidase A Therapy In A Mouse Model Of Fabry Disease," Clin. Exp. Immunol. 137(3):496-502.

(Continued)

*Primary Examiner* — Yunsoo Kim
(74) *Attorney, Agent, or Firm* — MORRISON & FOERSTER LLP

(57) ABSTRACT

The present application provides methods of treating Pompe disease such as infantile-onset Pompe disease (IOPD) using a pharmaceutical composition comprising an oligosaccharide-acid α-glucosidase (GAA) conjugate, such as avalglucosidase alfa. Also provided are formulations of the oligosaccharide-GAA conjugates.

15 Claims, 16 Drawing Sheets

(56) References Cited

OTHER PUBLICATIONS

Hahn, S. H. et al. (Oct. 2018, e-pub. Mar. 22, 2018). "Efficacy, Safety Profile, And Immunogenicity Of Alglucosidase Alfa Produced At The 4,000-Liter Scale In US Children And Adolescents With Pompe Disease: Advance, A Phase Iv, Open-Label, Prospective Study," Genetics In Medicine 20(10):1284-1294.

Haley, S. M. et al. (2004). "Pediatric Physical Functioning Reference Curves," Pediatric Neurology 31(5):333-341.

Haley, S. M. et al. (Apr.-Jun. 2003, e-pub. Jul. 10, 2009). "Development Of A Disease-Specific Disability Instrument For Pompe Disease," Pediatric Rehabilitation 6(2):77-84.

Hoefsloot, L. H. et al. (1990). "Characterization Of The Human Lysosomal A-Glucosidase Gene," Biochemical Journal 272(2):493-497.

Hug, C. et al. (Oct. 1, 2019). "177. Mini-COMET Study: Safety Data and Immunogenicity for Repeat Avalglucosidase Alfa Dosing in Patients with Infantile-onset Pompe Disease who were Previously Treated with Alglucosidase Alfa and Demonstrated Clinical Decline, "brAnnals Of Neurology 86, pp. S123-S124.

International Preliminary Report on Patentability, issued Jul. 28, 2022, mailed Jun. 8, 2021, for PCT Application No. PCT/US2021/017113, filed Feb. 8, 2021, 7 pages.

International Search Report and Written Opinion of the International Searching Authority, mailed Jun. 8, 2021, for PCT Application No. PCT/US2021/017113, filed Feb. 8, 2021, 13 pages.

Jones, A.J.S. (1993). "Analysis of Polypeptides and Proteins," Adv. Drug Delivery Rev. 10:29-90.

Joseph, A. et al. (2008). "Immune Tolerance Induction To Enzyme-Replacement Therapy By Co-Administration Of Short-Term, Low-Dose Methotrexate In A Murine Pompe Disease Model," Clin. Exp. Immunol. 152(1):138-146.

Kishnani, P. S. et al. (May 2006). "Pompe Disease Diagnosis And Management Guideline," Genetics In Medicine 8(5):267-288.

Kishnani, P.S. et al. (Jan. 9, 2007). "Recombinant Human Acid A-Glucosidase: Major Clinical Benefits In Infantile-Onset Pompe Disease," Neurology 68(2):99-109.

Kohler, L. et al. (Aug. 16, 2018). "Pompe Disease: From Basic Science To Therapy," Neurotherapeutics 15:928-942.

Kronn, D. et al. (2020). "222. Mini-COMET Study: Safety, Immunogenicity, And Preliminary Efficacy For Repeat Avalglucosidase Alfa Dosing In Patients With Infantile-Onset Pompe Disease (IOPD) Who Were Previously Treated With Alglucosidase Alfa And Demonstrated Clinical Decline," Molecular Genetics and Metabolism 129(2):S92, 2 pages.

Martiniuk, F. et al. (Dec. 1986). "Isolation Of A cDNA For Human Acid Alpha-Glucosidase And Detection Of Genetic Heterogeneity For mRNA In Three Alpha-Glucosidase-Deficient Patients," Proceedings Of The National Academy Of Sciences 83(24):9641-9644.

Mendelsohn, N. et al. (Jan. 8, 2009). "Elimination of Antibodies to Recombinant Enzyme in Pompe's Disease", NEJM 360(2):194-195.

Moreland, R. J. et al. (Feb. 25, 2005). "Lysosomal Acid A-Glucosidase Consists Of Four Different Peptides Processed From A Single Chain Precursor," Journal Of Biological Chemistry 280(8):6780-6791.

NIH (Jan. 22, 2023). "Homo Sapiens Alpha Glucosidase (GAA), Transcript Variant 1, Mrna," NCBI Reference Sequence: NM_000152.5, 6 pages.

NIH (Nov. 18, 2019). "A Study to Assess Safety and Efficacy of Avalglucosidase Alfa Administered Every Other Week in Pediatric Patients Pompe Disease Previously Treated With Alglucosidase Alfa (Mini-COMET)," ClinicalTrials.gov, Study No. NCT03019406, 6 pages.

Palisano, R. et al. (1997). "Gross Motor Function Classification System For Cerebral Palsy," Dev Med Child Neurol 39(4):214-223, 3 pages.

Palisano, R. J. et al. (2008). "Content Validity Of The Expanded And Revised Gross Motor Function Classification System," Developmental Medicine & Child Neurology 50(10):744-750.

Piper, M.C. et al. (Jul.-Aug. 1992). "Construction And Validation Of The Alberta Infant Motor Scale (AIMS)," Can J Public Health. 83 Suppl 2:S46-S50.

Prakalapakorn, S. G. et al. (Nov.-Dec. 2014, e-pub. Nov. 1, 2015). "Ocular And Histologic Findings In A Series Of Children With Infantile Pompe Disease Treated With Enzyme Replacement Therapy," Journal Of Pediatric Ophthalmology & Strabismus 51(6):355-362.

Prater, S. N. et al. (Sep. 2012, e-pub. Apr. 26, 2012). "The Emerging Phenotype Of Long-Term Survivors With Infantile Pompe Disease," Genetics In Medicine 14(9):800-810.

Sanofi (Aug. 6, 2021). "FDA Approves Nexviazyme® (avalglucosidase alfa-ngpt), An Important New Treatment Option For Late-Onset Pompe Disease," located at https://www.sanofi.com/en/media-room/press-releases/2021/2021-08-06-17-42-21-2276588, last visited on Sep. 1, 2022, 4 pages.

Sanofi (Feb. 2, 2021). "Data Presented At Worldsymposiumtm Reinforces Robust Rare Disease Pipeline And Highlights Additional Clinical Data For Investigational Avalglucosidase Alfa In Pompe Disease," located at https://www.sanofi.com/en/media-room/press-releases/2021/2021-02-02-14-00-00, last visited on Sep. 1, 2022, 5 pages.

Sanofi (Feb. 8, 2022). "Nexviazyme® (Avalglucosidase Alfa) Shows Sustained Improvements In Respiratory Function And Mobility In Patients With Pompe Disease," located at a href="https://www.sanofi.com/en/media-room/press-releases/2022/2022-02-08-14-00-00-2380936" target="_blank"https://www.sanofi.com/en/media-room/press-releases/2022/2022-02-08-14-00-00-2380936/a, last visited on Aug. 31, 2022, 4 pages.

Sanofi (Jul. 27, 2021). "Sanofi Provides Update On Avalglucosidase Alfa EU Submission For Patients With Pompe Disease," located at https://www.sanofi.com/en/media-room/press-releases/2021/2021-07-27-19-23-10-2269762, last visited on Sep. 1, 2022, 2 pages.

Sanofi (Jun. 8, 2020). "Sanofi To Present Phase 3 Results Of Avalglucosidase Alfa In Patients With Late-Onset Pompe Disease," located at a href="https://www.sanofi.com/en/media-room/press-releases/2020/2020-06-08-07-00-00" target="_blank"https://www.sanofi.com/en/media-room/press-releases/2020/2020-06-08-07-00-00/a, last visited on Sep. 1, 2022, 3 pages.

Sanofi (Nov. 12, 2021). "Sanofi Announces Results Of CHMP Re-Examination Of The New Active Substance Status For Avalglucosidase Alfa, A Potential New Standard Of Care For The Treatment Of Pompe Disease," located at https://www.sanofi.com/en/media-room/press-releases/2021/2021-11-12-11-38-38-2333221, last visited on Aug. 31, 2022, 4 pages.

Sanofi (Nov. 18, 2020). "FDA Grants Priority Review For Avalglucosidase Alfa, A Potential New Therapy For Pompe Disease," located at https://www.sanofi.com/en/media-room/press-releases/2020/2020-11-18-07-00-00, last visited on Sep. 1, 2022, 3 pages.

Sanofi (Oct. 2, 2020). "EMA Accepts Regulatory Submission For Avalglucosidase Alfa, A Potentially New Standard Of Care Enzyme Replacement Therapy For Pompe Disease," located at https://www.sanofi.com/en/media-room/press-releases/2020/2020-10-02-07-00-00, last visited on Sep. 1, 2022. 3 pages.

Slingerland, N.W. et al. (2011, e-pub. Mar. 26, 2011). "Ptosis, Extraocular Motility Disorder, And Myopia As Features Of Pompe Disease," Orbit. 30(2):111-113.

Spiridigliozzi, G. A. et al. (Jun. 2017, e-pub. Jun. 4, 2018). "Cognitive And Academic Outcomes In Long-Term Survivors Of Infantile-Onset Pompe Disease: A Longitudinal Follow-Up," Molecular Genetics And Metabolism 121(2):127-137.

Van Capelle, C. I. et al. (2018, e-pub. Jul. 19, 2019). "Cardiac Outcome In Classic Infantile Pompe Disease After 13 Years Of Treatment With Recombinant Human Acid Alpha-Glucosidase," International Journal Of Cardiology 269:104-110.

Wang, L. et al. (Jan. 7, 2003). "Addition Of The Keto Functional Group To The Genetic Code Of *Escherichia Coli*," Proceedings Of The National Academy Of Sciences 100(1):56-61.

Wang, R. Y. et al. (2014). "Carotid Intima Media Thickness Is Increased In Patients With Treated Mucopolysaccharidoses Types I And II, And Correlates With Arterial Stiffness," Molecular Genetics And Metabolism 2(111):S111, 1 page.

(56) References Cited

OTHER PUBLICATIONS

Winkel, L. P. et al. (2004, e-pub. Nov. 22, 2003). "Enzyme Replacement Therapy In Late-Onset Pompe's Disease: A Three-Year Follow-Up," Annals Of Neurology 55(4):495-502.

Wright, M. J. et al. (1998). "Long-Term Gross Motor Performance Following Treatment For Acute Lymphoblastic Leukemia," Medical And Pediatric Oncology: The Official Journal Of SIOP—International Society Of Pediatric Oncology (SocietéInternationale d'Oncologie Pédiatrique 31(2):86-90.

Diaz-Manera, J. et al. (Dec. 2021). "Safety And Efficacy Of Avalglucosidase Alfa Versus Alglucosidase Alfa In Patients With Late-Onset Pompe Disease (COMET): A Phase 3, Randomised, Multicentre Trial," The Lancet Neurology 20(12):1012-1026.

Dimachkie, M.M. et al. (Aug. 2, 2022). "Long-Term Safety And Efficacy Of Avalglucosidase Alfa In Patients With Late-Onset Pompe Disease," Neurology 99(5):e536-e548.

Kishnani, P. S. et al. (2023, e-pub. Dec. 21, 2022). "Safety and efficacy of avalglucosidase alfa in individuals with infantile-onset Pompe disease enrolled in the phase 2, open-label Mini-COMET study: The 6-month primary analysis report," Genetics in Medicine 25(2):100328, 1-13.

Pena, L.D.M. et al. (Mar. 2019). "Safety Tolerability, Pharmacokinetics, Pharmacodynamics, and Exploratory Efficacy of the Novel Enzyme Replacement Therapy Avalglucosidase alfa (neoGAA) in Treatment-Naïve and Alglucosidase Alfa-Treated Patients with Late-Onset Pompe Disease: A Phase 1, Open-Label, Multicenter, Multinational, Ascend," Neuromuscular Disorders 29(3):167-186.

Reuser, A. J. J. et al. (1984). "Uptake And Stability Of Human And Bovine Acid A-Glucosidase In Cultured Fibroblasts And Skeletal Muscle Cells From Glycogenosis Type II Patients," Experimental Cell Research 155(1):178-189.

Seo, J. et al. (2022, e-pub. May 29, 2022). "Mannose-6-Phosphate Glycan For Lysosomal Targeting: Various Applications From Enzyme Replacement Therapy To Lysosome-Targeting Chimeras," Animal Cells and Systems 26(3):84-91.

Tong, P. Y. et al. (May 15, 1989). "Ligand Interactions Of The Cation-Independent Mannose 6-Phosphate Receptor: The Stoichiometry Of Mannose 6-Phosphate Binding," Journal Of Biological Chemistry 264(14):7962-7969.

Van Den Hout, H. M. et al. (Aug. 2, 2003). "The Natural Course Of Infantile Pompe's Disease: 20 Original Cases Compared With 133 Cases From The Literature," Pediatrics 112(2):332-340.

Van Der Ploeg, A. T. et al. (Feb. 1991). "Intravenous Administration Of Phosphorylated Acid Alpha-Glucosidase Leads To Uptake Of Enzyme In Heart And Skeletal Muscle Of Mice," The Journal Of Clinical Investigation 87(2):513-518.

Zhu, Y. et al. (Aug. 2005). "Carbohydrate-Remodeled Acid A-Glucosidase With Higher Affinity For The Cation-Independent Mannose 6-Phosphate Receptor Demonstrates Improved Delivery To Muscles Of Pompe Mice," Biochem. J. 389:619-628.

Zhu, Y. et al. (Jun. 2009, e-pub. Mar. 10, 2009). "Glycoengineered Acid a-Glucosidase with Improved Efficacy at Correcting the Metabolic Aberrations and Motor Function Deficits in a Mouse Model of Pompe Disease," Molecular Therapy 17(6):954-963.

GENZYME (Apr. 25, 2006). "Text of the Labeling of the Drug: MYOZYME (alglucosidase alfa)," Center for Drug Evaluation and Research and Center for Biologics Evaluation and Research, Application No. 125141/0, 24 pages.

GENZYME (Aug. 4, 2021). "Product Quality Review(s): NEXVIAZYME (avalglucosidase alfa-ngpt)," Center for Drug Evaluation and Research, Application No. 761194Orig1s000, 80 pages.

\* cited by examiner

Measurement tool

Interpalpebral Fissure Distance (IPFD)
from flash photograph

Margin Reflex Distance-1 (MRD-1)
from flash photograph

Margin Pupil Distance (MPD)
from flash photograph

B. GMFM-88 Total percent score by Baseline value

C. QMFT Total score by cohort

D. QMFT Total score by Baseline value

A. Participant #1

A. Cohort 2 Avalglucosidase alfa (40 mg/kg qow) and
Cohort 3 Avalglucosidase alfa (40 mg/kg qow)

B. Cohort 1 Avalglucosidase alfa (20 mg/kg qow) and
Cohort 3 Alglucosidase alfa (20 mg/kg qow to 40 mg/kg weekly)

COMPOSITIONS AND METHODS FOR TREATING POMPE DISEASE

CROSS REFERENCE TO RELATED APPLICATIONS

This application claims priority benefit of U.S. Provisional Patent Applications No. 62/971,930 filed on Feb. 8, 2020, and No. 63/115,975 filed on Nov. 19, 2020, the contents of which are incorporated herein by reference in their entirety.

FIELD

The present application relates to compositions and methods for treating Pompe disease such as infantile-onset Pompe disease (IOPD).

BACKGROUND

Pompe disease (also known as glycogen storage disease type II, or GSD-II) is a genetically inherited lysosomal storage disease in which a deficiency in the glycogen degradation enzyme acid α-glucosidase (GAA) causes the accumulation of glycogen in lysosomes resulting in muscle weakness and cardiomegaly (Chien, Y. and Hwu, W. *Biologics* 2007 1:3; Kishnani, P. S. et al., *Genetics in Medicine* 2006 8). The most severe form of Pompe disease is infantile-onset Pompe disease (IOPD), in which symptoms start early in life, and the disease progresses very quickly: IOPD symptoms begin at a median age of two months, and death occurs at a median age of 8.7 months if patients are left untreated (Chien, Y., et al., *The Journal of Pediatrics* 2015 166:4; Chien, Y. and Hwu, W. *Biologics* 2007 1:3).

Enzyme replacement therapies (ERT) using recombinant GAA have been developed to treat IOPD (for example, Kishnani, P. S. et al. *Neurology* 2007 68:2). Nonetheless, IOPD is a difficult disease to treat, and there remains a need for improvement in the long-term prognosis and relief of symptoms in patients with IOPD (Prater, S. N. et al., *Genet. Med.* 2012 14:9; Chien, Y., et al., *The Journal of Pediatrics* 2015 166:4). Accordingly, there exists a need in the art for methods and compositions for treating Pompe disease, and in particular for treating IOPD.

BRIEF SUMMARY

The present application provides methods and compositions for treating Pompe disease, such as IOPD, in an individual in need thereof. Also provided are compositions and formulations for use in treating Pompe Disease such as IOPD and use of compositions and formulations in the preparation of a medicament for treating Pompe Disease such as IOPD.

One aspect of the present application provides a method for treating an infantile-onset Pompe disease (IOPD), comprising administering to a human individual in need thereof a pharmaceutical composition comprising an oligosaccharide-protein conjugate and a pharmaceutically acceptable carrier, wherein the oligosaccharide-protein conjugate has a structure of Formula I:

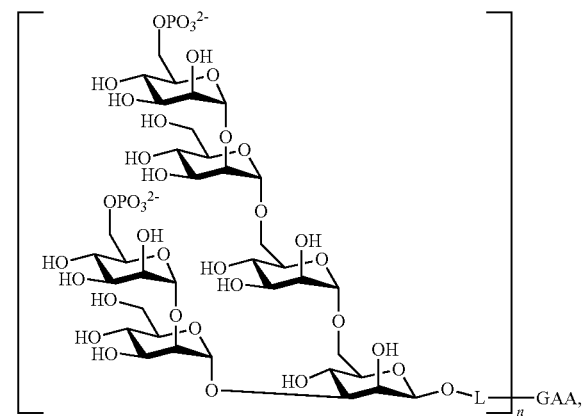

wherein GAA is acid α-glucosidase, L is a chemical linker connecting the oligosaccharide and the GAA, and n is 1 to 10, and wherein the pharmaceutical composition is administered at a dose of about 20 mg/kg to about 40 mg/kg. In some embodiments, the pharmaceutical composition is administered at a dose of about 20 mg/kg. In some embodiments, the pharmaceutical composition is administered at a dose of about 40 mg/kg. In some embodiments, the pharmaceutical composition is administered to the individual once every two weeks. In some embodiments, the pharmaceutical composition is administered intravenously. In some embodiments, the pharmaceutical composition is administered to the individual for at least about 25 weeks.

In some embodiments according to any one of the methods described above, the pharmaceutical composition is reconstituted from a lyophilized formulation comprising the oligosaccharide-protein conjugate. In some embodiments, the pharmaceutically acceptable carrier comprises a sugar that is not degraded by GAA. In some embodiments, the sugar that is not degraded by GAA is mannitol. In some embodiments, the pharmaceutically acceptable carrier further comprises glycine. In some embodiments, the pharmaceutically acceptable carrier comprises histidine. In some embodiments, the pharmaceutical composition has a pH of about 6.2. In some embodiments, the pharmaceutically acceptable carrier comprises about 10-50 mM histidine, about 0.25-2% glycine, about 1-4% mannitol, and about 0.005-0.05% polysorbate 80. In some embodiments, the pharmaceutically acceptable carrier comprises about 10 mM histidine, about 2% glycine, about 2% mannitol, and about 0.01% polysorbate 80.

In some embodiments according to any one of the methods described above, the individual has cardiomyopathy at the time of diagnosis in the first year of life. In some embodiments, the individual has arrhythmia. In some embodiments, the individual has cardiomegaly. In some embodiments, the individual is 18 years old or younger. In some embodiments, the individual is about 6 months old or younger.

In some embodiments according to any one of the methods described above, the individual has received at least 6 months of treatment with a recombinant GAA. In some embodiments, the individual shows clinical decline after treatment with the recombinant GAA, wherein the clinical decline is determined by assessing one or more parameters selected from the group consisting of respiratory functions, motor skills and cardiac parameters. In some embodiments, the individual has suboptimal clinical response to treatment with the recombinant GAA, wherein the clinical response is determined by assessing one or more parameters selected from the group consisting of respiratory functions, motor skills and cardiac parameters. In some embodiments, the individual has not received treatment with a recombinant GAA. In some embodiments, the recombinant GAA is alglucosidase alfa.

In some embodiments according to any one of the methods described above, the individual is cross-reactive immunologic material (CRIM)-negative. In some embodiments, the individual is CRIM-positive.

In some embodiments according to any one of the methods described above, the method further comprises administering to the individual an effective amount of methotrexate. In some embodiments, the effective amount of methotrexate is administered in a single cycle or in three cycles. In some embodiments, the methotrexate is administered in a single cycle. In some embodiments, the methotrexate is administered in a two, three, four, five or more cycles. In some embodiments, a cycle of methotrexate consists of 1 day of methotrexate administration or 2, 3, 4, 5, 6, 7, 8, 9, 10, or 11 consecutive days of methotrexate administration. In some embodiments, the methotrexate is administered to the individual at a time selected from one or more of before, during, and after administration of the oligosaccharide-protein conjugate. In some embodiments, the methotrexate is administered between 48 hours prior to and 48 hours after the administration of the oligosaccharide-protein conjugate. In some embodiments, the methotrexate is administered concurrently with administration of the oligosaccharide-protein conjugate and about 24 and about 48 hours after administration of the oligosaccharide-protein conjugate. In some embodiments, the methotrexate is administered at about 0.1 mg/kg to about 5 mg/kg. In some embodiments, the method further comprises administering to the individual an additional immune tolerance induction therapy. In some embodiments, the additional immune tolerance induction therapy comprises rituximab and intravenous immunoglobulin (IVIG).

In some embodiments according to any one of the methods described above, the individual has decreasing level of antidrug antibody (ADA) against the oligosaccharide-protein conjugate over time.

In some embodiments according to any one of the methods described above, creatine kinase (CK) level of the individual decreases by at least about 100 IU/L when measured after at least about 25 weeks of treatment.

In some embodiments according to any one of the methods described above, urinary hexose tetrasaccharide (Hex4) level of the individual decreases by at least about 10 mmol/mol when measured after at least about 25 weeks of treatment.

In some embodiments according to any one of the methods described above, Gross Motor Function Measure (GMFM-88) score of the individual increases by at least 5% when measured after at least about 25 weeks of treatment.

In some embodiments according to any one of the methods described above, the individual shows improvement or stabilization of one or more parameters selected from the group consisting of respiratory functions, motor skills, cardiac parameters and eyelid positions. In some embodiments, the improvement or stabilization is assessed based on one or more parameters selected from the group consisting of Alberta Infant Motor Scale (AIMS) score, Pompe-Pediatric Evaluation of Disability Inventory (PEDI) functional skills scale, Echocardiographic (ECHO)-left ventricular mass (LVM) Z-score, ECHO LVMI score, Gross Motor Function Classification System-Expanded and Revised (GMFCS-E&R) score, Quick Motor Function Test, 6 Minute Walk test (6MWT), interpalpebral fissure distance (IPFD), margin reflex distance-1 (MRD-1), margin pupil distance (MPD), onset of ptosis, and use of respiratory support. In some embodiments, the improvement or stabilization is assessed based on Pompe-PEDI functional skills scale. In some embodiments, the improvement or stabilization is assessed based on ECHO-LVM Z-score.

In some embodiments according to any one of the methods described above, the oligosaccharide-protein conjugate has a structure of Formula II:

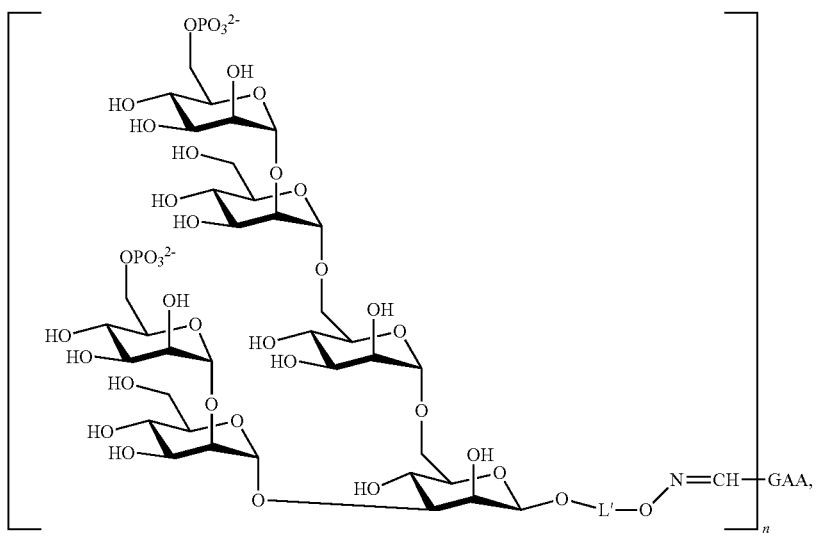

wherein GAA is acid α-glucosidase, L' is a chemical linker, and n is 1 to 10.

In some embodiments according to any one of the methods described above, the oligosaccharide-protein conjugate has a structure of Formula III:

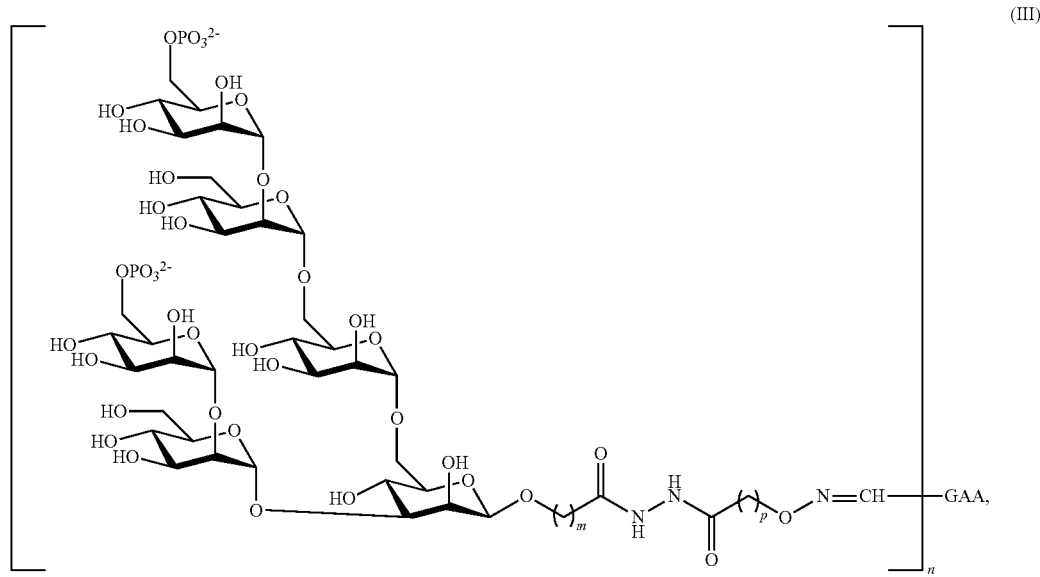

wherein GAA is acid α-glucosidase, n is 1 to 10, and wherein m and p are independently chosen from integers ranging from 1 to 10. In some embodiments, m is 3 and p is 1. In some embodiments, n is 5-7.

In some embodiments according to any one of the methods described above, the GAA is a human GAA produced in Chinese hamster ovary (CHO) cells. In some embodiments, the human GAA has glycoform alfa. In some embodiments, the oligosaccharide-protein conjugate is avalglucosidase alfa.

Another aspect of the present application provides a formulation comprising: (a) an oligosaccharide-protein conjugate; and (b) one or more cryoprotectants comprising a sugar that is not degraded by acid α-glucosidase; wherein the oligosaccharide-protein conjugate has a structure of Formula I:

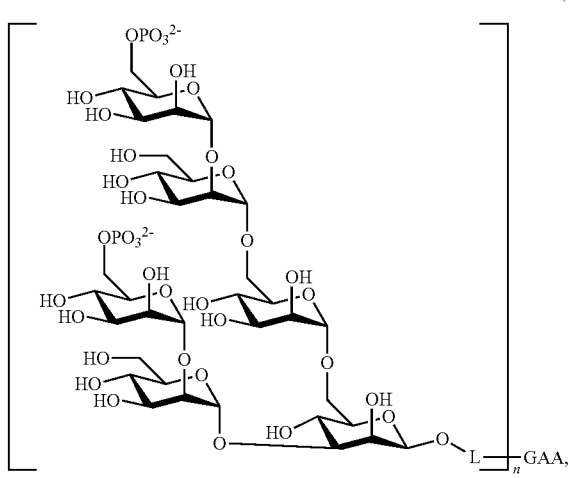

wherein GAA is acid α-glucosidase, L' is a chemical linker, and n is 1 to 10. In some embodiments, the sugar is mannitol. In some embodiments, the formulation comprises about 1-4% (w/w) mannitol, such as about 2% mannitol.

In some embodiments according to any one of the formulations described above, the one or more cryoprotectants further comprises an amino acid. In some embodiments, the amino acid is glycine. In some embodiments, the formulation comprises about 0.25-2% (w/w) glycine, such as about 2% glycine.

In some embodiments according to any one of the formulations described above, the one or more cryoprotectants further comprises a surfactant. In some embodiments, the surfactant is polysorbate 80. In some embodiments, the formulation comprises about 0.005-0.05% (w/w) polysorbate 80, such as about 0.01% polysorbate 80.

In some embodiments according to any one of the formulations described above, the formulation further comprises a buffering agent. In some embodiments, the buffering agent is histidine. In some embodiments, the formulation comprises about 10-50 mM histidine, such as about 10 mM histidine.

In some embodiments according to any one of the formulations described above, the formulation comprises about comprising 10 mM histidine, about 2% glycine, about 2% mannitol, and about 0.01% polysorbate 80.

In some embodiments according to any one of the formulations described above, the formulation is a lyophilized formulation. In some embodiments, the formulation is a pre-lyophilized (i.e., lyophilizable) formulation. In some embodiments, the formulation is a reconstituted liquid formulation. In some embodiments, the pH of the formulation is about 5.5 to about 6.5. In some embodiments, the pH of the formulation is about 6.2.

In some embodiments according to any one of the formulations described above, the formulation comprises about 5-10 mg/mL (e.g., about 5 mg/mL) of the oligosaccharide-protein conjugate.

In some embodiments according to any one of the formulations described above, the oligosaccharide-protein conjugate a structure of Formula II:

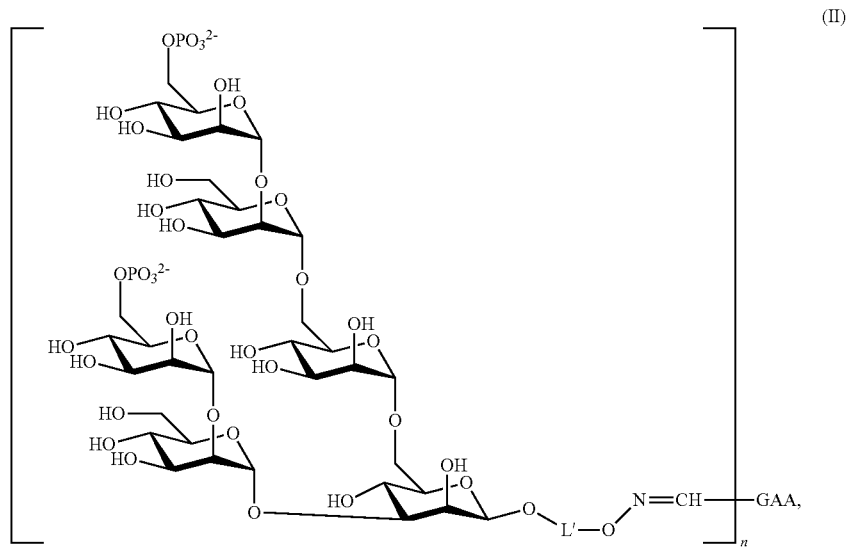

(II)

wherein GAA is acid α-glucosidase, L' is a chemical linker, and n is 1 to 10.

In some embodiments according to any one of the formulations described above, the oligosaccharide-protein conjugate has a structure of Formula III:

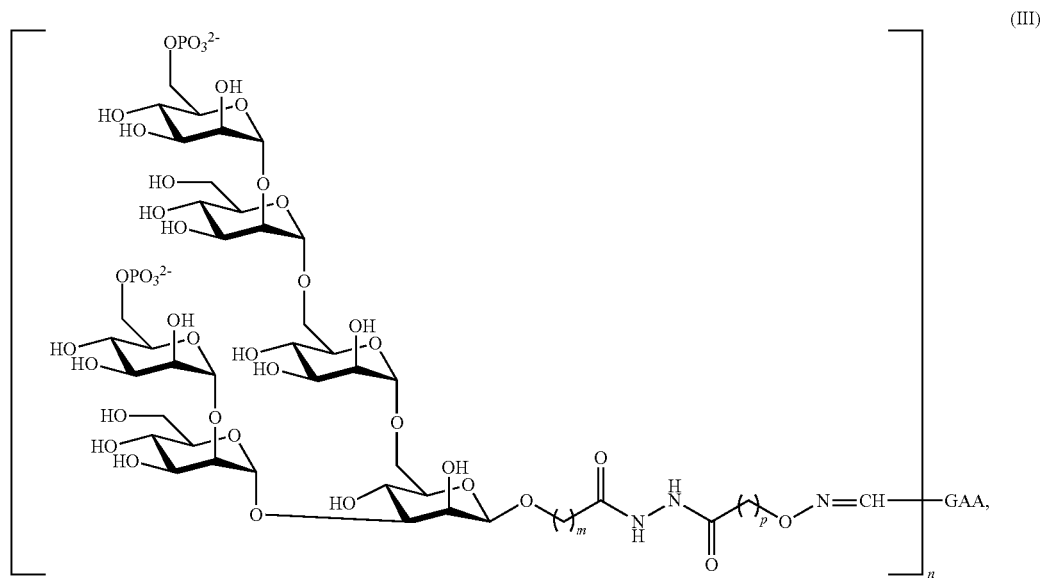

(III)

wherein GAA is acid α-glucosidase, n is 1 to 10, and wherein m and p are independently chosen from integers ranging from 1 to 10. In some embodiments, m is 3 and p is 1. In some embodiments, n is 5-7.

In some embodiments according to any one of the formulations described above, the GAA is a human GAA produced in Chinese hamster ovary (CHO) cells. In some embodiments, the human GAA has glycoform alfa. In some embodiments, the oligosaccharide-protein conjugate is avalglucosidase alfa.

Another aspect of the present application provides an article of manufacture comprising a container comprising the formulation according to any one of the formulations described above. In some embodiments, the container is a vial. In some embodiments, the formulation is a lyophilized formulation.

Further provided is a method of treating Pompe disease, comprising administering to a human individual in need thereof an effective amount of a pharmaceutical composition comprising the formulation according to any one of the formulations described above. In some embodiments, the Pompe disease is IOPD.

Also provided is a kit comprising the formulation according to any one of the formulations described above. In some embodiments, the kit further comprises instructions for use in treating Pompe disease (e.g., IOPD).

BRIEF DESCRIPTION OF THE DRAWINGS

FIG. 2A shows GMFM-88 scores of Cohort 1 (blue) and Cohort 2 (orange) during the primary analysis period. FIG. 2B shows GMFM-88 scores of Cohort 3 receiving alglucosidase alfa to be followed by avalglucosidase alfa after week 25 (pink) or receiving alglucosidase alfa (green) during the primary analysis period. In FIG. 2B, the * denotes that for one GMFCS Level V patient, GMFM-88 was not measured. In FIGS. 2A-2B, the x-axis shows the amount of time from baseline in weeks, and the y-axis shows the change from baseline (mean±standard deviation).

FIG. 4A shows change in CK levels of Cohort 1 (blue) and Cohort 2 (orange) during the primary analysis period. FIG. 4B shows change in CK levels of Cohort 3 receiving alglucosidase alfa to be followed by avalglucosidase alfa after week 25 (pink) or receiving alglucosidase alfa (green) during the primary analysis period. In FIGS. 4A-4B, the x-axis shows the amount of time from baseline in weeks, and the y-axis shows the change from baseline (median). The CK levels at baseline in IU/L for the different cohorts are as follows: Cohort 1 Mean: 1102.17, Standard deviation: 932.43, Median: 750, Minimum: 318.0, and Maximum: 2607.0; Cohort 2 Mean: 1444.80, Standard deviation: 164.17, Median: 1472, Minimum: 1188.0, Maximum: 1645.0; Cohort 3 receiving avalglucosidase alfa Mean: 1211.40, Standard deviation: 597.45, Median: 1528, Minimum: 347.0, and Maximum: 1704.0; and Cohort 3 receiving alglucosidase alfa to be followed by avalglucosidase alfa after week 25 Mean: 1136.17, Standard deviation: 672.61, Median: 1179, Minimum: 273.0, and Maximum: 1830.0.

FIG. 5A shows change in HEX4 levels of Cohort 1 (blue) and Cohort 2 (orange) during the primary analysis period. FIG. 5B shows change in HEX4 levels of Cohort 3 receiving alglucosidase alfa to be followed by avalglucosidase alfa after week 25 (pink) or receiving alglucosidase alfa (green) during the primary analysis period. In FIGS. 5A-5B, the x-axis shows the amount of time from baseline in weeks, and the y-axis shows the change from baseline (median). The HEX4 levels at baseline in mmol/mol for the different cohorts are as follows: Cohort 1 Mean: 80.25, Standard deviation: 48.38, Median: 73.12, Minimum: 16.1, and Maximum: 143.3; Cohort 2 Mean: 63.43, Standard deviation: 30.71, Median: 71.31, Minimum: 20.0, Maximum: 97.3; Cohort 3 receiving avalglucosidase alfa Mean: 54.81, Standard deviation: 50.41, Median: 42.54, Minimum: 11.9, and Maximum: 141.0; and Cohort 3 receiving alglucosidase alfa to be followed by avalglucosidase alfa after week 25 Mean: 52.16, Standard deviation: 33.93, Median: 69.17, Minimum: 4.2, and Maximum: 80.6.

FIG. 7A: right eye; FIG. 7B: left eye), Margin Reflex Distance-1 (MRD-1; FIG. 7C: right eye; FIG. 7D: left eye), Margin Pupil Distance (MPD; FIG. 7E: right eye; FIG. 7F: left eye).

FIG. 11A shows results in Cohort 2 (avalglucosidase alfa 40 mg/kg qow) and Cohort 3 (avalglucosidase alfa 40 mg/kg qow). FIG. 11B shows results in Cohort 1 (avalglucosidase alfa 20 mg/kg qow) and Cohort 3 (alglucosidase alfa 20 mg/kg qow and 40 mg/kg weekly).

Figure 1:
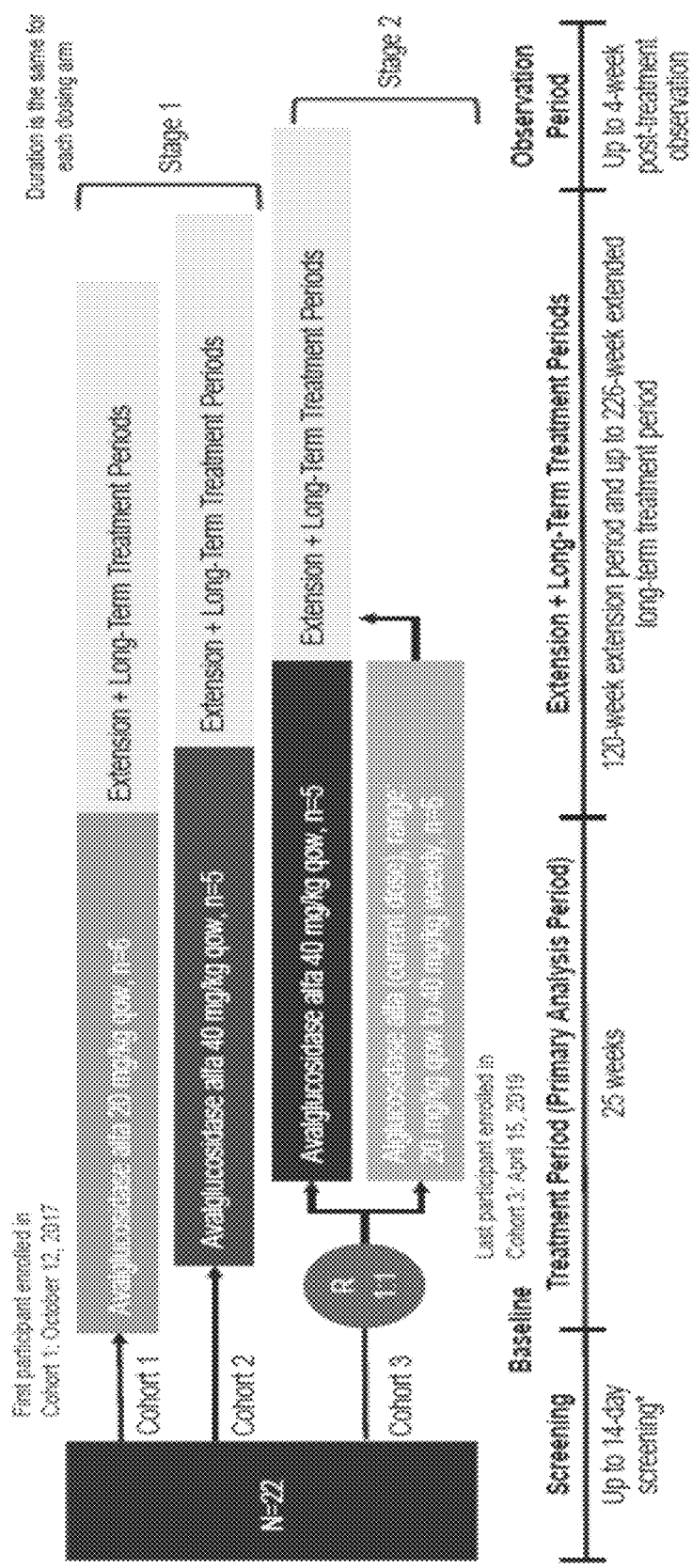
FIG. 1 provides a schematic summaries of the study design. Cohort 1 is shown in blue, Cohort 2 is shown in orange, and the two arms of Cohort 3 are shown in pink and green. Time from baseline is shown from left to right.

immune tolerance induction therapy, i.e., methotrexate, rituximab and IVIG in this dosage regimen.

DETAILED DESCRIPTION

The present application provides compositions and methods for treating Pompe disease, including infantile-onset Pompe Disease (IOPD), which is the most severe form of Pompe disease, using an oligosaccharide-acid α-glucosidase (GAA) conjugate. In some embodiments, the compositions described herein are lyophilized formulations of an oligosaccharide-GAA conjugate, which have high stability after storage and/or after reconstitution. In some embodiments, the oligosaccharide-GAA conjugate is avalglucosidase alfa. Clinical trials of avalglucosidase alfa in human patients demonstrate efficacy of the compositions described herein for treating Pompe disease such as IOPD even among patients who exhibit clinical decline or suboptimal clinical response after treatment with a recombinant GAA.

I. Definitions

Terms are used herein as generally used in the art, unless otherwise defined as follows.

The term "acid α-glucosidase" and "GAA" are used herein interchangeably to refer to the protein acid α-glucosidase. In some embodiments, the GAA is a recombinant GAA. In some embodiments, the GAA is a human GAA.

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of Pompe disease (such as IOPD). The methods of the application contemplate any one or more of these aspects of treatment.

The terms "individual," "subject" and "patient" are used interchangeably herein to describe a mammal, including humans. In some embodiments, the individual is human. In some embodiments, an individual suffers from a disease, such as IOPD. In some embodiments, the individual is in need of treatment.

As is understood in the art, an "effective amount" refers to an amount of a therapeutic agent or composition (e.g. a composition comprising avalglucosidase alfa) sufficient to produce a desired therapeutic outcome (e.g., reducing the severity or duration of, stabilizing the severity of, or eliminating one or more symptoms of IOPD), or to achieve a desired prophylactic result (e.g., induce immune tolerance to the therapeutic agent). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients. In some embodiments, an effective amount of the therapeutic agent may extend survival (including overall survival and progression free survival); result in an objective response (including a complete response or a partial response); relieve to some extent one or more signs or symptoms of the disease or condition; and/or improve the quality of life of the subject. For purposes of this application, an effective amount of drug, compound, or pharmaceutical composition is an amount sufficient to accomplish prophylactic or therapeutic treatment either directly or indirectly.

As used herein, "baseline value" refers to value of a biomarker of an individual prior to or at the beginning of a treatment.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to one or more ingredients in a pharmaceutical formulation, other than an active ingredient, which is nontoxic to a subject. A pharmaceutically acceptable carrier includes, but is not limited to, a buffer, excipient, stabilizer, cryoprotectant, tonicity agent, preservative, and combinations thereof.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

The terms "pre-lyophilized formulation" and "lyophilizable formulation" are used herein interchangeably to refer to formulations that are subject to lyophilization to prepare a lyophilized formulation.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or condition (e.g., IOPD), or a probe for specifically detecting a biomarker described herein. In certain embodiments, the manufacture or kit is promoted, distributed, or sold as a unit for performing the methods described herein.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat disease of type X means the method is used to treat disease of types other than X.

The term "about X-Y" used herein has the same meaning as "about X to about Y."

As used herein and in the appended claims, the singular forms "a," "an," or "the" include plural referents unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the compositions and methods described herein are specifically embraced by the present invention and are disclosed herein just as if each and every combination was individually and explicitly disclosed. In addition, all subcombinations of features and properties of the compositions and methods in the embodiments describing such variables are also specifically embraced by the present invention and are disclosed herein just as if each and every such sub-combination was individually and explicitly disclosed herein.

II. Methods of Treatment

The present application provides methods of treating Pompe disease, such as infantile-onset Pompe disease (IOPD), in an individual in need thereof using any one of the oligosaccharide-GAA conjugates described herein (e.g., Formulae I-III, or avalglucosidase alfa).

In some embodiments, the present disclosure provides a method of treating Pompe disease, comprising administering to a human individual in need thereof an effective amount of a pharmaceutical composition comprising an oligosaccharide-protein conjugate, wherein the oligosaccharide protein and a pharmaceutically acceptable carrier, wherein the oligosaccharide-protein conjugate has a structure of Formula I:

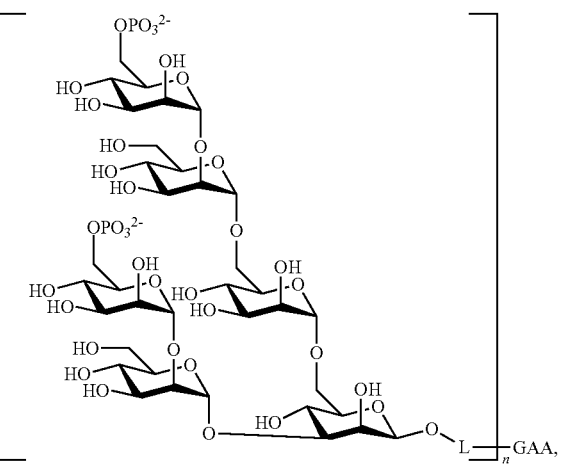

wherein GAA is acid α-glucosidase, L is a chemical linker connecting the oligosaccharide and the GAA, and n is 1 to 10. In some embodiments, the pharmaceutical composition is administered at a dose of about 20 mg/kg to about 40 mg/kg (e.g., about 20 mg/kg or about 40 mg/kg). In some embodiments, the pharmaceutically acceptable carrier comprises histidine, glycine, mannitol and/or polysorbate 80. In some embodiments, the pharmaceutically acceptable carrier comprises about 10-50 mM (e.g., about 10 mM) histidine, about 0.25-2% (e.g., about 2%) glycine, about 1-4% (e.g., about 2%) mannitol and about 0.005-0.05% (e.g., about 0.01%) polysorbate 80. In some embodiments, the pharmaceutical composition has a pH of about 5.5 to about 6.5, such as about 6.2. In some embodiments, the Pompe disease is IOPD. In some embodiments, the oligosaccharide-protein conjugate has a structure of Formula (II):

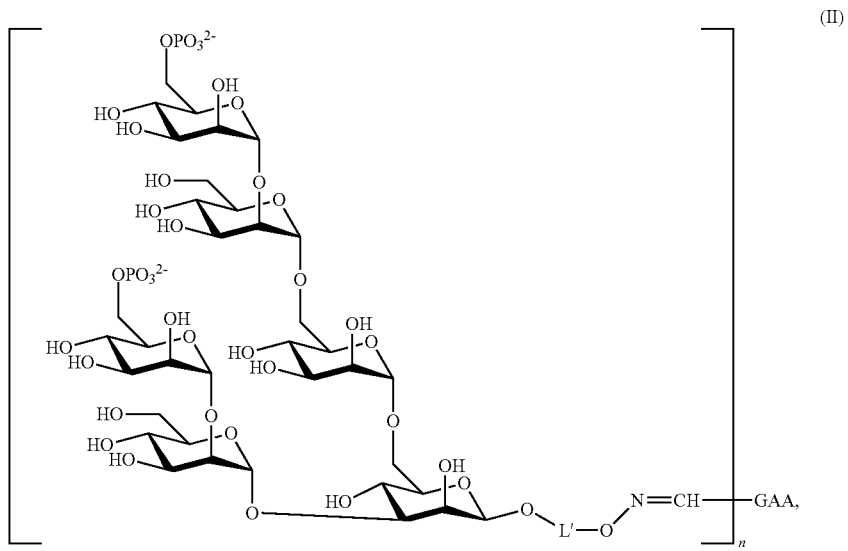
wherein GAA is acid α-glucosidase, L' is a chemical linker, and n is 1 to 10. In some embodiments, the oligosaccharide-protein conjugate has a structure of Formula (III):
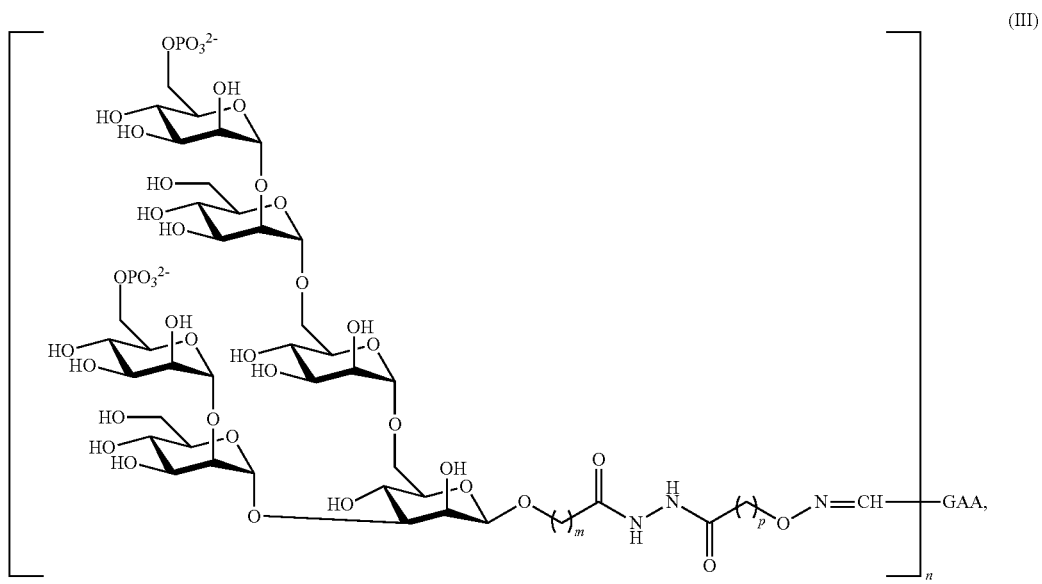

wherein GAA is acid α-glucosidase, n is 1 to 10, and m and p are independently chosen from integers ranging from 1 to 10. In some embodiments, m is 3 and p is 1. In some embodiments, n is 5-7. In some embodiments, the oligosaccharide-protein conjugate is avalglucosidase alfa.

In some embodiments, there is provided a method of treating IOPD, comprising administering to a human individual in need thereof a pharmaceutical composition comprising an oligosaccharide-protein conjugate and a pharmaceutically acceptable carrier, wherein the oligosaccharide-protein conjugate has a structure of Formula I:

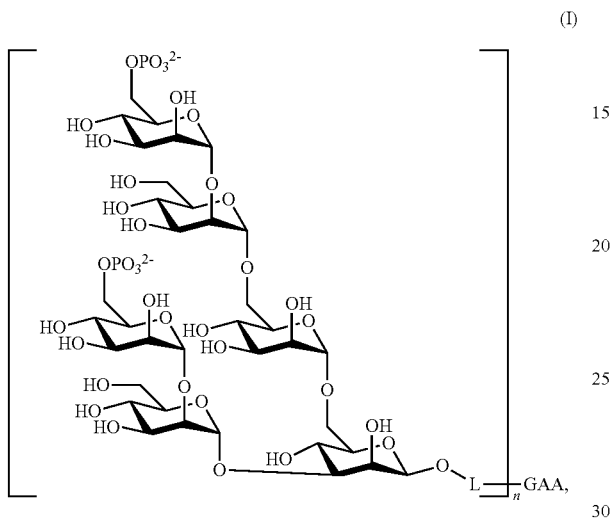

(I)

wherein GAA is acid α-glucosidase, L is a chemical linker connecting the oligosaccharide and the GAA, and n is 1 to 10, and wherein the pharmaceutical composition is administered at a dose of about 20 mg/kg to about 40 mg/kg (e.g., about 20 mg/kg or about 40 mg/kg). In some embodiments, the oligosaccharide-protein conjugate has a structure of Formula II:

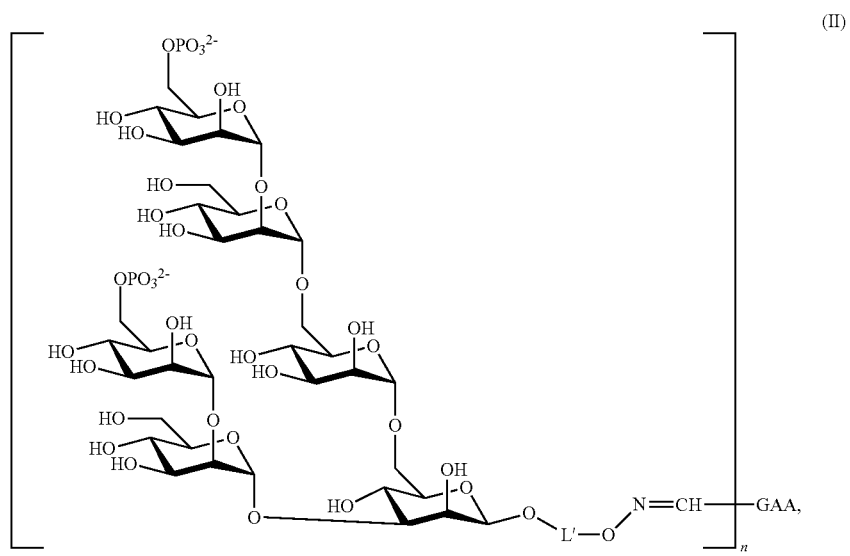

(II)

wherein GAA is acid α-glucosidase, L' is a chemical linker, and n is 1 to 10. In some embodiments, the oligosaccharide-protein conjugate has a structure of Formula III:

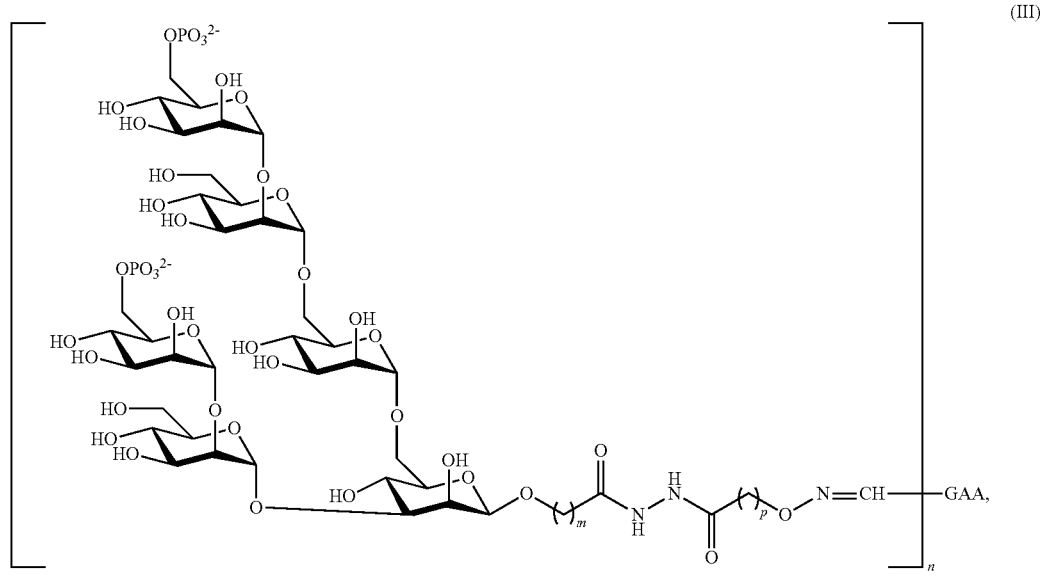

wherein GAA is acid α-glucosidase, n is 1 to 10, and m and p are independently chosen from integers ranging from 1 to 10. In some embodiments, m is 3 and p is 1. In some embodiments, n is 5-7. In some embodiments, the oligosaccharide-protein conjugate is avalglucosidase alfa.

In some embodiments, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the individual is 6 months or younger. In some embodiments, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the individual starts receiving the treatment at 6 months or younger. In some embodiments, the individual has not received treatment with a recombinant GAA prior to receiving the oligosaccharide-GAA conjugate. In some embodiments, the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

Creatine kinase (CK, also known as creatine phosphokinase) is a serum enzyme biomarker of Pompe disease that is indicative of muscle damage; CK levels are elevated in patients in with classic IOPD (Burton, B. K. et al. *Pediatrics* 2017 140:s1). A CK blood test may be performed to measure the amount of CK enzyme in an individual's blood.

Accordingly, in some embodiments of the present application, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg), and wherein creatine kinase (CK) levels of the individual decreases by at least about 100 IU/L when measured after at least about 25 weeks of treatment. In some embodiments, there is provided a method of decreasing creatine kinase level in a human individual having an IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, and wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In embodiments, CK level decreases by at least about any one of 50 IU/L, 60 IU/L, 70 IU/L, 80, IU/L, 90 IU/L, 100 IU/L, 110 IU/L, 120 IU/L, 130 IU/L, 140 IU/L, 150 IU/L, 160 IU/L, 170 IU/L, 180 IU/L, 190 IU/L, 200 IU/L, 250 IU/L, 300 IU/L, 400 IU/L, 500 IU/L, 600 IU/L, 700 IU/L, 800 IU/L or more, when measured after a certain duration of treatment. In some embodiments, the CK level decreases by about any one of 50 IU/L, 60 IU/L, 70 IU/L, 80, IU/L, 90 IU/L, 100 IU/L, 110 IU/L, 120 IU/L, 130 IU/L, 140 IU/L, 150 IU/L, 160 IU/L, 170 IU/L, 180 IU/L, 190 IU/L, 200 IU/L, 250 IU/L, 300 IU/L, 400 IU/L, 500 IU/L, 600 IU/L, 700 IU/L, 800 IU/L or more, when measured after a certain duration of treatment, including any value or range in between these values. In some embodiments, the CK level decreases by at least about any one of 10%, 20%, 30%, 40%, 50%, 60%, 70%, 80%, 90% or more, relative to baseline when measured after a certain duration of treatment. In some embodiments, the CK level decreases by no more than about any one of 90%, 80%, 70%, 60%, 50%, 40%, 30%, 20%, or 10% relative to baseline when measured after a certain duration of treatment. In some embodiments, the CK level decreases by about any one of 10%, 20%, 30%, 40%, 50%, 60%, 70%, 80%, 90%, including any value or range in between these values. In some embodiments, the CK level is measured after treatment of about any one of 1 months, 3 months, 6 months, 25 weeks, 7 months, 8 months, 9 months, 12 months, 2 years, 5 years, 10 years or more, including any value or range in between these values.

Another biomarker of IOPD is glucose tetrasaccharide, which is elevated in urine and plasma of patients with Pompe disease (Burton, B. K. et al. *Pediatrics* 2017 140:s1). Glucose tetrasaccharide can be measured as hexose tetrasaccharide (Hex4) levels in urine, as Hex4 is a breakdown product of glycogen. Thus, urinary Hex4 serves as a biomarker of glycogen storage (Burton, B. K. et al. *Pediatrics* 2017 140:s1).

Accordingly, in some embodiments of the methods herein, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg), and wherein urinary hexose tetrasaccharide (Hex4) level of the individual decreases by at least about 10 mmol/mol when measured after at least about 25 weeks of treatment. In some embodiments, there is provided a method of decreasing urinary Hex4 level in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, and wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the urinary Hex4 level of the individual decreases by at least about any one of 5 mmol/mol, 6 mmol/mol, 7 mmol/mol, 8 mmol/mol, 9 mmol/mol, 10 mmol/mol, 11 mmol/mol, 12 mmol/mol, 13 mmol/mol, 14 mmol/mol, 15 mmol/mol, 20 mmol/mol, 25 mmol/mol, 30 mmol/mol, 35 mmol/mol, 40 mmol/mol, or 50 mmol/mol, when measured after a certain duration of treatment. In some embodiments, the urinary Hex4 level of the individual decreases by about any one of 5 mmol/mol, 6 mmol/mol, 7 mmol/mol, 8 mmol/mol, 9 mmol/mol, 10 mmol/mol, 11 mmol/mol, 12 mmol/mol, 13 mmol/mol, 14 mmol/mol, 15 mmol/mol, 20 mmol/mol, 25 mmol/mol, 30 mmol/mol, 35 mmol/mol, 40 mmol/mol, or 50 mmol/mol, when measured after a certain duration of treatment, including any value or range in between these values. In some embodiments, the urinary Hex4 level decreases by at least about 10%, 20%, 30%, 40%, 50%, 60%, 70%, 80%, 90% or more, relative to baseline when measured after a certain duration of treatment. In some embodiments, the urinary Hex4 level decreases by no more than about 90%, 80%, 70%, 60%, 50%, 40%, 30%, 20%, or 10% relative to baseline when measured after a certain duration of treatment. In some embodiments, the Hex4 level decreases by about any one of 10%, 20%, 30%, 40%, 50%, 60%, 70%, 80%, 90%, including any value or range in between these values. In some embodiments, the Hex4 level is measured after treatment of about any one of 1 months, 3 months, 6 months, 25 weeks, 7 months, 8 months, 9 months, 12 months, 2 years, 5 years, 10 years or more, including any value or range in between these values.

Muscle weakness associated with IOPD may be assessed using a Gross Motor Function Measure-88 (GMFM-88) score. GMFM-88 is an 88-item measurement that takes into consideration an individual's gross motor activities in the five dimensions of (1) lying and rolling, (2) sitting, (3) crawling and kneeling, (4) standing, and (5) walking, running and jumping. Items in the GMFM-88 were selected to represent motor functions typically performed by children without motor impairments by 5 years of age. Each item is scored on a 4-point Likert scale (i.e., 0=cannot do; 1=initiates [<10% of the task]; 2=partially completes [10% to <100% of the task]; 3=task completion). The score for each dimension is expressed as a percentage of the maximum score for that dimension. Total score is obtained by adding the percentage scores for each dimension and dividing the sum by the total number of dimensions. Therefore, each dimension contributes equally to the total score.

The GMFM-88 test is intended for use in children, and can be used in young children under one year of age. There is no age cut-off for the GMFM-88. GMFM-88 is used in the art according to a published manual (Russell, D. J., et al. *Gross Motor Function Measure (GMFM-66 & GMFM-88) User's Manual,* 2nd edition 2013). While not originally validated for children with diagnoses other than cerebral palsy, the GMFM-88 has been used for other children with motor difficulties including children with osteogenesis imperfecta (Russell, D. J., et al. *Gross Motor Function Measure (GMFM-66 & GMFM-88) User's Manual,* 2nd edition 2013) and acute lymphoblastic leukemia (Wright, M. J., et al. *Med Pediatr Oncol.* 1998 31:2). The GMFM-88 has been used to evaluate children and adults with Pompe disease (Winkel, L. P. et al., *Ann Neurol.* 2004 55:4) and can be used to measure change in motor performance over time secondary to an improvement or decline in muscle strength.

Accordingly, in some embodiments of the methods herein, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg), and wherein the Gross Motor Function Measure-88 (GMFM-88) score of the individual increases by at least 5% when measured after at least about 25 weeks of treatment. In some embodiments, there is provided a method of improving and/or increasing a GMFM-88 score of a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, and wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the GMFM-88 score increases by at least about any one of 3%, 4%, 5%, 6%, 7%, 8%, 9%, 10%, 11%, 12%, 13%, 14%, 15%, or more including any value or range in between these values. In some embodiments, the GMFM-88 score increases by at least about any one of 5%, 10%, 20%, 30%, 40%, 50%, 60%, 70%, 80%, 90% or more, relative to baseline when measured after a certain duration of treatment. In some embodiments, the GMFM-88 score increases by no more than about any one of 90%, 80%, 70%, 60%, 50%, 40%, 30%, 20%, or 10% relative to baseline when measured after a certain duration of treatment. In some embodiments, the GMFM-88 score increases by about any one of 5%, 10%, 20%, 30%, 40%, 50%, 60%, 70%, 80%, or 90%, including any value or range in between these values. In some embodiments, the GMFM-88 score is determined after treatment of about any one of 1 months, 3 months, 6 months, 25 weeks, 7 months, 8 months, 9 months, 12 months, 2 years, 5 years, 10 years or more, including any value or range in between these values.

In some embodiments, the individual shows improvement or stabilization as assessed by a Gross Motor Function Classification System-Expanded and Revised (GMFCS-E&R) parameter. The GMFCS-E&R emphasizes concepts in the World Health Organization's International Classification of Functioning, Disability and Health. Emphasis is on usual performance in home, work and community settings without judgments about quality of movement or prognosis for improvement. The GMFCS-E&R is a standardized system originally developed to classify the gross motor function of children with cerebral palsy (Palisano, R., et al. *Dev. Med. Child Neurol.* 1997 39:4). GMFCS-E&R may also be applied to assessments of Pompe disease (for example, Spiridigliozzi, G. A. et al. *Mol. Genet. Metab.* 2017 121:2). The GMFCS-E&R is a 5 level classification system for specific age ranges consisting of Levels I to V based on self-initiated movement, with emphasis on sitting, transfers, and mobility. The distinctions between levels are based on functional limitations, the need for assistive mobility devices, and to a much lesser extent, quality of movement, and are designed to be meaningful in daily life (Palisano R. J., et al. *Dev Med Child Neurol.* 2008 50:10).

The general headings for the 5 levels are:
Level I: Walks without limitations
Level II: Walks with limitations
Level III: Walks using a hand-held mobility device
Level IV: Self-mobility with limitations; may use powered mobility
Level V: Transported in a manual wheelchair Accordingly, in some embodiments of the methods herein, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg), and wherein the GMFCS-E&R score of the individual increases when measured after at least about 25 weeks of treatment. In some embodiments, there is provided a method of improving a GMFCS-E&R score of a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the GMFCS-E&R score increases by at least about any one of 10%, 20%, 30%, 40%, 50%, 60%, 70%, 80%, 90% or more relative to baseline when measured after a certain duration of treatment. In some embodiments, the GMFCS-E&R score increases by no more than about any one of 90%, 80%, 70%, 60%, 50%, 40%, 30%, 20%, or 10% relative to baseline when measured after a certain duration of treatment. In some embodiments, the GMFCS-E&R score increases by about any one of 10%, 20%, 30%, 40%, 50%, 60%, 70%, 80%, or 90%, including any value or range in between these values. In some embodiments, the GMFCS-E&R score increases by 1 level, 2 levels, 3 levels, or 4 levels relative to baseline when measured after a certain duration of treatment. In some embodiments, the GMFCS-E&R score is determined after treatment of about any one of 1 months, 3 months, 6 months, 25 weeks, 7 months, 8 months, 9 months, 12 months, 2 years, 5 years, 10 years or more, including any value or range in between these values.

In some embodiments, the individual shows improvement or stabilization of one or more parameters selected from the group consisting of respiratory functions, motor skills, cardiac parameters, and eyelid positions. Exemplary parameters include, but are not limited to, Pompe-Pediatric Evaluation of Disability Inventory (PEDI) functional skills scale, Echocardiographic (ECHO)-left ventricular mass (LVM) Z-score, ECHO LVMI score, Gross Motor Function Classification System-Expanded and Revised (GMFCS-E&R) score, Quick Motor Function Test, 6 Minute Walk test (6MWT), interpalpebral fissure distance (IPFD), margin reflex distance-1 (MRD-1), margin pupil distance (MPD), onset of ptosis, and use of respiratory support. In some embodiments, the individual shows improvement or stabilization of one or more parameters relative to baseline after a certain duration of treatment. The duration of treatment may be after at least about 10 weeks, 13 weeks, 20 weeks, 25 weeks, 30 weeks, 40 weeks, 49 weeks, 61 weeks, 73 weeks, 97 weeks, or 100 weeks, 5 months, 6 months, 7 months, 8 months, 9 months, 10 months, 11 months, 1 year, 2 years, 3 years, 4 years, 5 years, or more.

In some embodiments, the individual shows improvement or stabilization of one or more of motor skills as assessed by the Pompe Pediatric Evaluation of Disability Inventory (Pompe-PEDI) Functional Skills Scale: Mobility Domain (Haley, S. M., et al. *Pediatr Rehabil* 2003 6:2; Haley, S. M., et al. *Pediatr. Neurol.* 2004 31). The Pompe-PEDI is a modification of the Pediatric Evaluation of Disability Inventory to be Pompe disease-specific, and includes both self-care and mobility items (e.g., head control, floor activity, sitting, standing, etc. (Haley, S. M., et al. *Pediatr. Neurol.* 2004 31). The raw Pompe-PEDI score is the sum of scores of items a child is capable of from the assessment. The normative and scaled scores, and associated standard deviation, are generated from a statistical program produced as part of the research study described in S.M., et al. *Pediatr. Neurol.* 2004 31; the program requires input of the subject's age and score and produces corresponding normative and scaled score data.

In some embodiments, there is provided a method of improving or stabilizing a Pompe-PEDI score in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the Pompe-PEDI Functional Skills Scale: Mobility Domain scaled score increases by at least about any one of 1, 2, 3, 4, 5, 6, 7, 8, 9, 10, 11, 12, 13, 14, 15, 16, 17, 18, 19, 20, 21, 22, 23, 24, 25, 25, 30, 40, or 50 points. In some embodiments, the Pompe-PEDI Functional Skills Scale: Mobility Domain scaled score increases by at least about any one of 5% 10%, 20%, 30%, 40%, 50%, 60%, 70%, 80%, 90% or more relative to baseline when measured after a certain duration of treatment. In some embodiments, the Pompe-PEDI Functional Skills Scale: Mobility Domain scaled score increases by no more than about any one of 90%, 80%, 70%, 60%, 50%, 40%, 30%, 20%, or 10% relative to baseline when measured after a certain duration of treatment. In some embodiments, the Pompe-PEDI Functional Skills Scale: Mobility Domain scaled score increases by about any one of 10%, 20%, 30%, 40%, 50%, 60%, 70%, 80%, or 90%, including any value or range in between these values. In some embodiments, the Pompe-PEDI Functional Skills Scale: Mobility Domain scaled score is determined after treatment of about any one of 1 months, 3 months, 6 months, 25 weeks, 7 months, 8 months, 9 months, 12 months, 2 years, 5 years, 10 years or more, including any value or range in between these values.

In some embodiments, there is provided a method of improving or stabilizing an Alberta Infant Motor Scale (AIMS) score in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

The Alberta Infant Motor Scale (AIMS) assesses gross infant motor skills from ages 0-18 months. It evaluates weight bearing, posture, and antigravity movements of infants. See, for example, Piper M C et al. Construction and validation of the Alberta Infant Motor Scale (AIMS). Can J Public Health. 1992 July-August; 83 Suppl 2:S46-50. PMID: 1468050.

In some embodiments, the individual shows improvement or stabilization of one or more motor skills as assessed by the Quick Motor Function Test (QMFT) (van Capelle, C. I., et al. *J Inherit Metab Dis.* 2012 35:2). The QMFT is a functional motor scale specific for Pompe disease, in which an evaluator observes the performance of a patient and scores them on 16 items (e.g., raising the torso, neck flexion, picking up an object, etc.) each on a 5-point scale.

In some embodiments, there is provided a method of improving or stabilizing a QMFT score of a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, individuals show an improvement on the QMFT scale. For example, an individual may show an improvement on the QMFT scale that is about any one of 2%, 3%, 4%, 5%, 6%, 7%, 8%, 9%, 10%, 11%, 12%, 13%, 14%, 15%, 16%, 17%, 18%, 19%, or 20% change from baseline after a certain duration of treatment. In some embodiments, the QMFT score increases by at least about any one of 5% 10%, 20%, 30%, 40%, 50%, 60%, 70%, 80%, 90% or more relative to baseline when measured after a certain duration of treatment. In some embodiments, the QMFT score increases by no more than about any one of 90%, 80%, 70%, 60%, 50%, 40%, 30%, 20%, or 10% relative to baseline when measured after a certain duration of treatment. In some embodiments, the QMFT score increases by about any one of 10%, 20%, 30%, 40%, 50%, 60%, 70%, 80%, or 90%, including any value or range in between these values. In some embodiments, the QMFT score is determined after treatment of about any one of 1 months, 3 months, 6 months, 25 weeks, 7 months, 8 months, 9 months, 12 months, 2 years, 5 years, 10 years or more, including any value or range in between these values.

In some embodiments, the individual shows improvement or stabilization of one or more cardiac parameters as assessed by echocardiographic (ECHO) endpoints such as the left ventricular mass index (LVMI) and/or the left ventricular mass (LVM) Z-score (Barker, P. A. C., et al. *Mol. Genet. Metab.* 2010 101:4). Cardiac failure is the main cause of death in Pompe disease patients, and echocardiography (also known as echo) is therefore used in the art to evaluate the cardiac response to ERT (van Capelle, C. I., et al. *Int. Journal of Cardiology* 2018 269). An echo Z score describes how many standard deviations above or below a size or age-specific population mean a given measurement lies (Chubb, H. and J. M. Simpson, *Ann. Pediatr. Cardiol.* 2012 5:2).

In some embodiments, there is provided a method of decreasing the LVMI of a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the LVMI decreases by at least about any one of 10%, 20%, 30%, 40%, 50%, 60%, 70%, 80%, 90% or more, relative to baseline when measured after a certain duration of treatment. In some embodiments, the LVMI decreases by no more than about any one of 90%, 80%, 70%, 60%, 50%, 40%, 30%, 20%, or 10% relative to baseline when measured after a certain duration of treatment. In some embodiments, the LVMI decreases by about any one of 10%, 20%, 30%, 40%, 50%, 60%, 70%, 80%, 90%, including any value or range in between these values. In some embodiments, the LVMI is determined after treatment of about any one of 1 months, 3 months, 6 months, 25 weeks, 7 months, 8 months, 9 months, 12 months, 2 years, 5 years, 10 years or more, including any value or range in between these values.

In some embodiments, there is provided a method of decreasing the LVM Z-score of a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the LVM Z-score decreases by at least about any one of 10%, 20%, 30%, 40%, 50%, 60%, 70%, 80%, 90% or more, relative to baseline when measured after a certain duration of treatment. In some embodiments, the LVM Z-score decreases by no more than about any one of 90%, 80%, 70%, 60%, 50%, 40%, 30%, 20%, or 10% relative to baseline when measured after a certain duration of treatment. In some embodiments, the LVM Z-score decreases by about any one of 10%, 20%, 30%, 40%, 50%, 60%, 70%, 80%, 90%, including any value or range in between these values. In some embodiments, the LVM Z-score is determined after treatment of about any one of 1 months, 3 months, 6 months, 25 weeks, 7 months, 8 months, 9 months, 12 months, 2 years, 5 years, 10 years or more, including any value or range in between these values.

In some embodiments, the individual shows improvement or stabilization of one or more of respiratory functions, motor skills and/or cardiac parameters as assessed by a 6 Minute Walk Test (6MWT). As used herein, a 6MWT assesses the distance walked in 6 minutes by patients who are able to ambulate at least 40 meters without stopping or using an assistive device. A 6MWT is improved, for example, if an individual is able to walk a greater distance in 6 minutes relative to baseline after a certain duration of treatment. In some embodiments, there is provided a method of improving the 6MWT score (e.g., increasing the distance walked) of a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, the individual shows improvement or stabilization of one or more of motor functions as assessed by the onset of ptosis. Ptosis is the drooping of the upper eyelid over the eye. In some embodiments, ptosis is delayed relative to average onset of ptosis in untreated IOPD patients when measured after a certain duration of treatment In some embodiments, there is provided a method of delaying the onset of ptosis in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

Figure 6A:
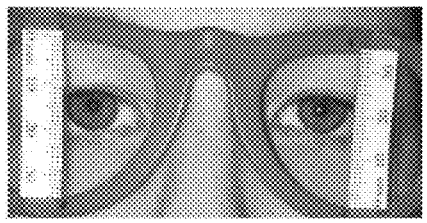
FIGS. 6A-6D show eyelid position measurements.
Figure 6B:
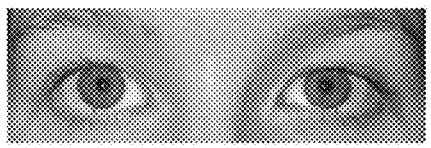
Figure 6C:
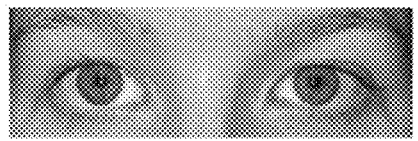
Figure 6D:
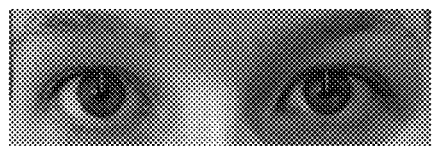
Figure 7A:
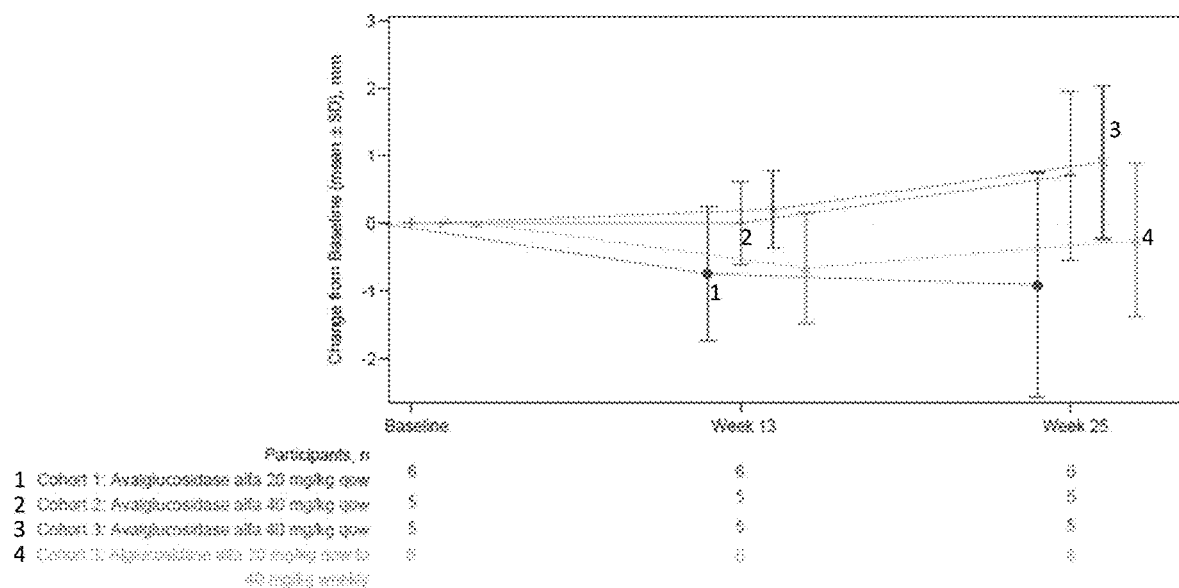
FIGS. 7A-7F show mean±standard deviation (SD) from baseline at Weeks 13 and 25 in Interpalpebral Fissure Distance (IPFD.
Figure 7B:
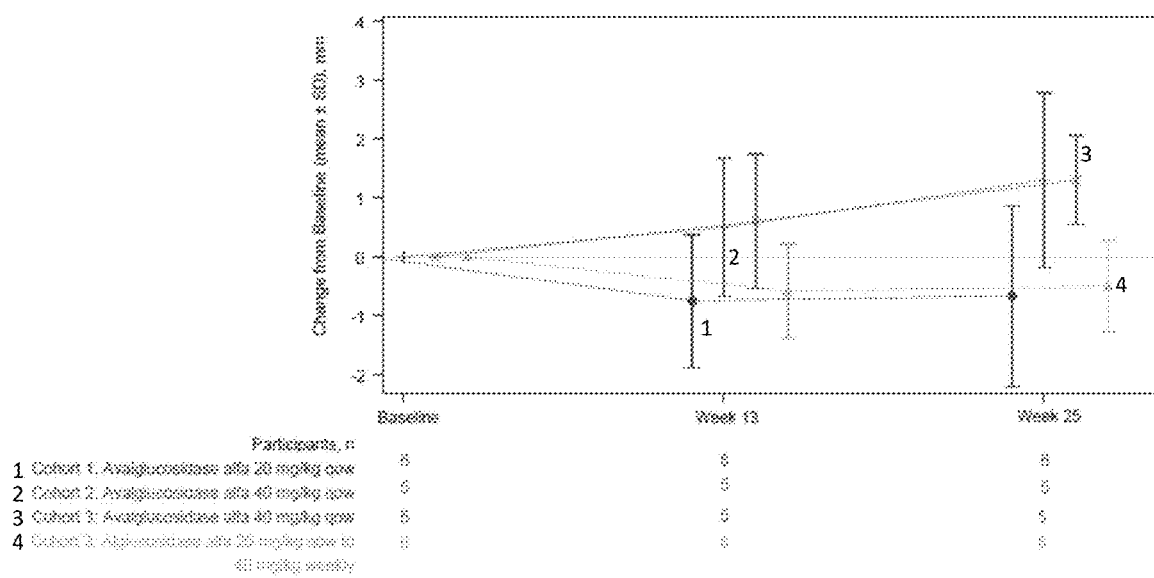
Figure 7C:
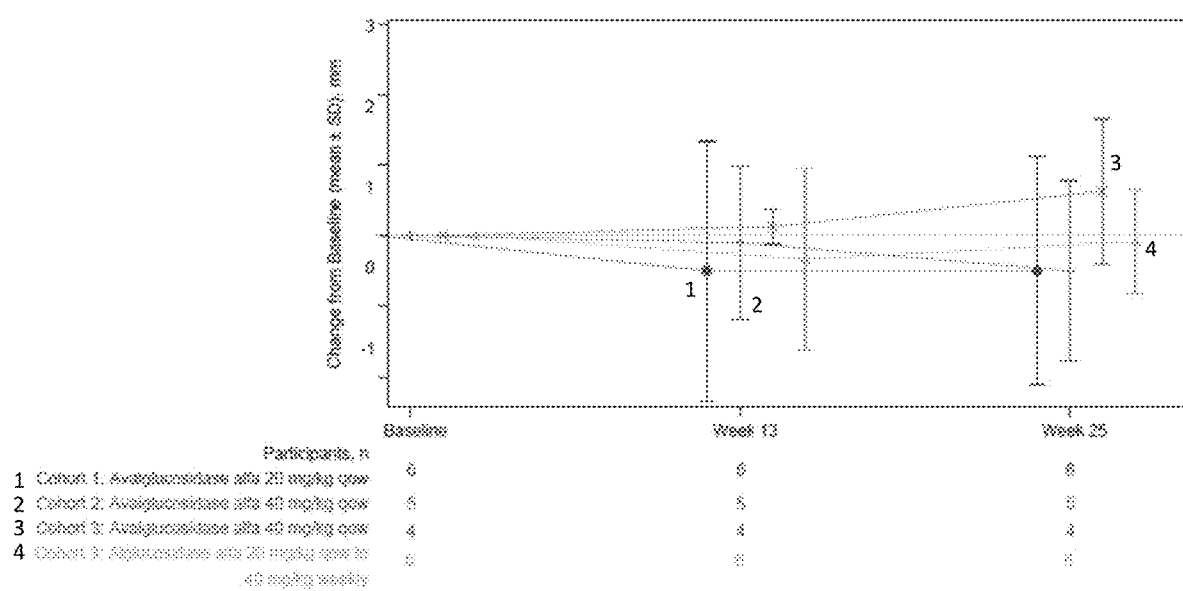
Figures 7D, 7E:
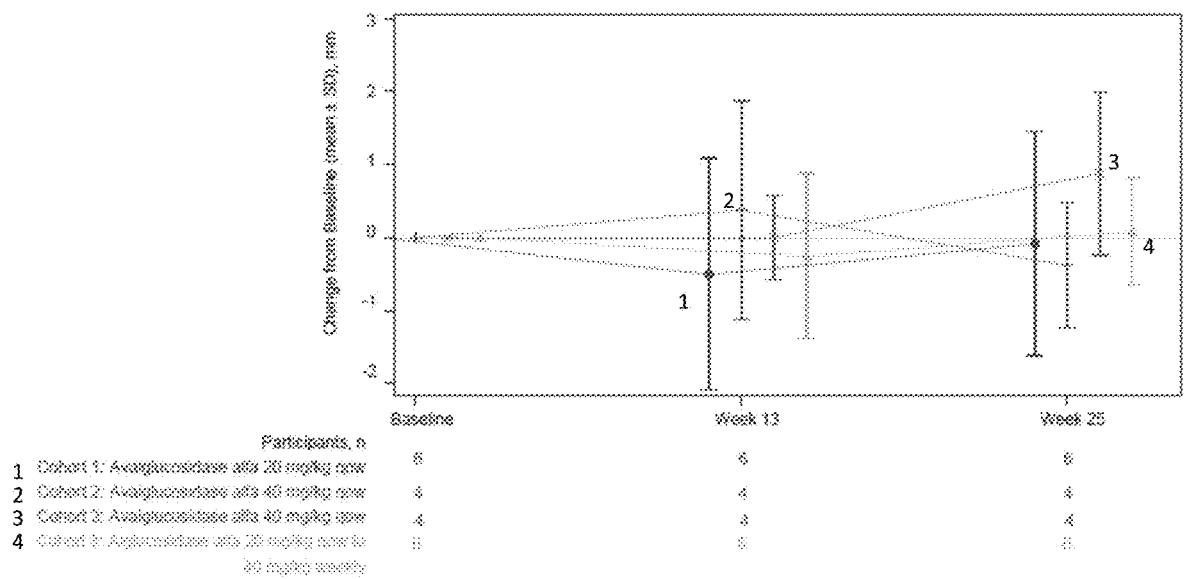
Figure 7F:
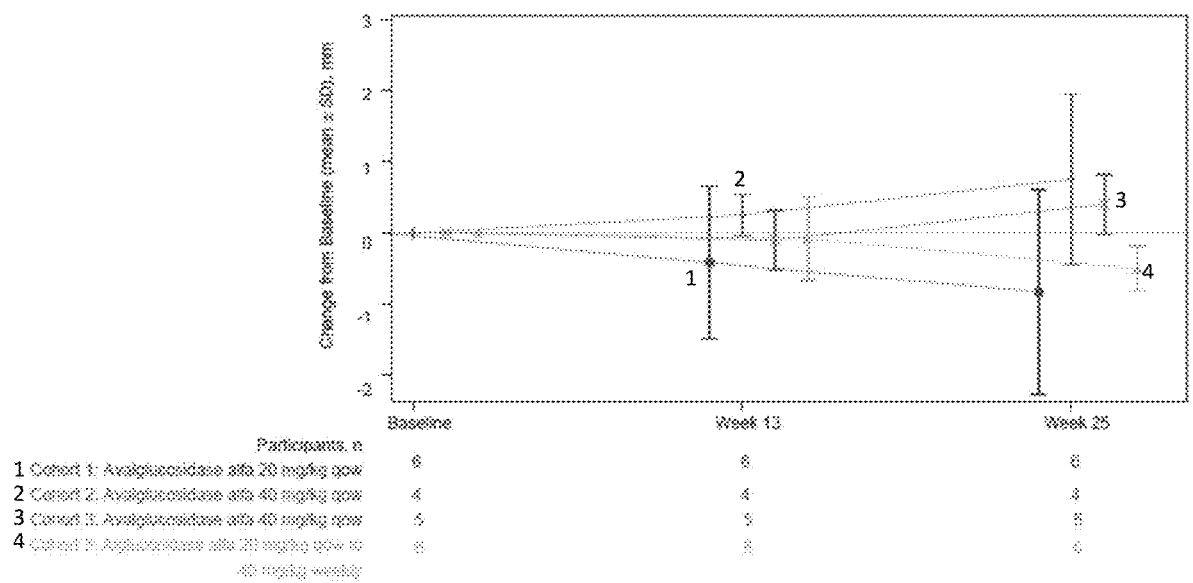

Ptosis may be assessed by measuring one or more eyelid positions using known methods in the art, for example, by using measurement tools as shown in FIG. 6A. Exemplary eyelid position measurements include, but are not limited to interpalpebral fissure distance (IPFD), margin reflex distance-1 (MRD-1), and margin pupil distance (MPD), which are shown in FIGS. 6B-6D. Ptosis (drooping eyelids) has been shown to occur in long-term survivors with infantile-onset Pompe disease (IOPD) receiving alglucosidase alfa and may be due to glycogen storage in the levator palpebrae muscle. Ptosis is potentially amblyogenic and if severe, may require surgical intervention. See, e.g., De Wilde F. et al. Surgical treatment of myogenic blepharoptosis. Bull Soc Belge Ophtalmol. 1995; 255:139-46; Slingerland N W, et al. Ptosis, extraocular motility disorder, and myopia as features of Pompe disease. Orbit. 2011; 30(2):111-3; and Prakalapakorn S G, et al. Ocular and histologic findings in a series of children with infantile Pompe disease treated with enzyme replacement therapy. J Pediatr Ophthalmol Strabismus. 2014; 51(6):355-9, which are incorporated herein by reference. The eyelid positions may be measured using flash photography or non-flash photography. In some embodiments, the eyelid positions (e.g., IPDF and MPD) are measured with non-flash photography. In some embodiments, the method decreases one or more of an IPFD, a MRD-1 and a MPD of the individual. In some embodiments, the method decreases an IPFD, a MRD-1 and a MPD of the individual. In some embodiments, the decrease is in both eyes. In some embodiments, the decrease is in one eye.

In some embodiments, there is provided a method of decreasing an interpalpebral fissure distance (IPFD) in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the pharmaceutical composition is administered at a frequency of every other week or weekly. In some embodiments, the oligosaccharide-protein conjugate is avalglucosidase alfa. In some embodiments, the decrease is in both eyes. In some embodiments, the decrease is in one eye.

In some embodiments, there is provided a method of decreasing a margin reflex distance-1 (MRD-1) in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the pharmaceutical composition is administered at a frequency of every other week or weekly. In some embodiments, the oligosaccharide-protein conjugate is avalglucosidase alfa. In some embodiments, the decrease is in both eyes. In some embodiments, the decrease is in one eye.

In some embodiments, there is provided a method of decreasing a margin pupil distance (MPD) in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the pharmaceutical composition is administered at a frequency of every other week or weekly. In some embodiments, the oligosaccharide-protein conjugate is avalglucosidase alfa. In some embodiments, the decrease is in both eyes. In some embodiments, the decrease is in one eye.

In some embodiments, the individual shows improvement or stabilization of one or more of respiratory functions as assessed by ventilator use. IOPD patients may require the use of a ventilator. Ventilators can be either invasive or non-invasive, used in the daytime or nighttime only, or used during both the daytime and the nighttime. In some embodiments, the individual uses a ventilator less frequently during the day, week, or month relative to baseline when measured after a certain duration of treatment. In some embodiments, the individual uses a less invasive ventilator relative to baseline when measured after a certain duration of treatment, such as about any one of 1 months, 3 months, 6 months, 25 weeks, 7 months, 8 months, 9 months, 12 months, 2 years, 5 years, 10 years or more, including any value or range in between these values.

In some embodiments, there is provided a method of delaying ventilator use in a human individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa.

In some embodiments, there is provided a method of prolonging invasive ventilator free survival and/or overall survival of an individual having IOPD, comprising administering to the individual a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg). In some embodiments, the oligosaccharide-protein conjugate is avalglucosidase alfa. In some embodiments, the invasive ventilator free survival is increase for about any one of 1 year, 2 years, 3 years, 4 years, 5 years, 10 years, 15 years, 20 years, 25 years, 30 years, 40 years or more, including any value or range in between these values. In some embodiments, the overall survival is increase for about any one of 1 year, 2 years, 3 years, 4 years, 5 years, 10 years, 15 years, 20 years, 25 years, 30 years, 40 years or more, including any value or range in between these values.

The methods described herein are also associated with low incidents of adverse effects. In some embodiments, there is provided a method of treating IOPD, comprising administering to a human individual in need thereof a pharmaceutical composition comprising any one of the oligosaccharide-GAA conjugates described herein (e.g., Formulae I-III, or avalglucosidase alfa) and a pharmaceutically acceptable carrier, wherein the pharmaceutical composition is administered at a dose of about 20 mg/kg to about 40 mg/kg (e.g., about 20 mg/kg or about 40 mg/kg), and wherein the individual has decreasing level of anti-drug antibody (ADA) against the oligosaccharide-protein conjugate over time. ADAs may form against a drug such as an oligosaccharide-protein conjugate. ADAs have the potential to neutralize the effects of a drug, and can therefore present a challenge in ERTs.

In some embodiments, the methods described herein further comprise preparing the pharmaceutical composition. In some embodiments, the pharmaceutical composition is reconstituted from a lyophilized formulation. In some embodiments, the pharmaceutical composition is reconstituted from a lyophilized formulation comprising the oligosaccharide-protein conjugate.

In some embodiments, there is provided use of any one of the oligosaccharide-GAA conjugates described herein (e.g., Formulae I-III, or avalglucosidase alfa) in the manufacture of a medicament for treating IOPD in a human individual in need thereof. In some embodiments, there is provided a pharmaceutical composition comprising any one of the oligosaccharide-GAA conjugates described herein (e.g., Formulae I-III, or avalglucosidase alfa) for treating IOPD in a human individual in need thereof.

The pharmaceutical compositions described herein may be administered to the individual intravenously, or with another suitable route of administration. Suitable dosage of the pharmaceutical composition is about 20 mg/kg to about 40 mg/kg, including about any one of 20, 21, 22, 23, 24, 25, 26, 27, 28, 29, 30, 31, 32, 33, 34, 35, 36, 37, 38, 39, or 40 mg/kg, including any value or range in between these values. In some embodiments, the pharmaceutical composition is administered at a dose of about 20 mg/kg. In some embodiments, the pharmaceutical composition is administered at a dose of about 40 mg/kg.

The pharmaceutical compositions described herein may be administered at a suitable frequency, including, for example, biweekly, once per week, once every two weeks, once every three weeks, or once every month. In some embodiments, the pharmaceutical composition is administered to the individual once every two weeks.

Administration of a pharmaceutical composition of the present application to an individual may occur in a single dose or in repeat administrations. For example, the pharmaceutical compositions described herein may be administered by intravenous infusion at a dose of about 20 mg/kg to about 40 mg/kg of body weight every two weeks over approximately, e.g., 1, 2, 3, 4, 5, 6, 7, 8, 9, or 10 hours. In some embodiments, the rate of administration may be started at, e.g., 1 mg/kg/hr and then increased by, e.g., 2 mg/kg/hr every 30 minutes, after establishing patient tolerance to the infusion rate, until a maximum of, e.g., 7 mg/kg/hr.

The pharmaceutical compositions described herein may be administered to the individual over an extended period of time, including, for example, at least about any one of 25 weeks, 6 months, 7 months, 8 months, 9 months, 10 months, 11 months, 12 months, 2 years, 3 years, 4 years, 5 years, 6 years, 7 years, 8 years, 9 years, 10 years, 12 years, 15 years, 20 years, 25 years, 30 years, or longer, including any value or range between these values.

A. Patient Population

Pompe disease (also known as acid maltase deficiency or glycogen storage disease (GSD) type II) is a rare, autosomal recessive genetic disorder caused by the deficiency of lysosomal acid α-glucosidase (GAA), an enzyme that degrades glycogen (see OMIM 232300). It has been classified into infantile onset and late onset forms. Classical infantile onset Pompe disease (IOPD) is characteristically fatal by one year of age without treatment. Late onset Pompe disease (LOPD) has a more variable course.

In particular, IOPD is characterized by rapidly progressive hypertrophic cardiomyopathy, left ventricular outflow obstruction, hypotonia and muscle weakness, respiratory distress, and progressive loss of independent ventilation (Kohler, L. et al., *Neurotherapeutics* 2018 15:4). Breathing difficulties, feeding problems, and macroglossia are common manifestations of IOPD, and motor development is typically significantly delayed (Kohler, L. et al., *Neurotherapeutics* 2018 15:4). IOPD may be diagnosed by newborn screening, as described in Burton, B. K. et al. *Pediatrics* 2017 140:s1.

Alglucosidase alfa, which contains the active ingredient recombinant human acid α-glucosidase (rhGAA), can be used as to treat Pompe disease as a long-term enzyme replacement therapy (ERT) for patients with a confirmed diagnosis of Pompe disease. Alglucosidase alfa treatment is globally approved (tradenames MYOZYME® and LUMIZYME®) for the treatment of Pompe disease based on its efficacy to prolong invasive ventilator free survival and overall survival in infants, and its ability to improve mobility and stabilize respiratory function in children and adults with the disease. Despite the availability of rhGAA, there remains an unmet need in Pompe disease, in particular for IOPD patients who frequently experience long-term motor decline despite early treatment. Without wishing to be bound by theory, this is thought to be, at least in part, due to the relative low level of bis-mannose-6-phosphate (bis-M6P) on alglucosidase alfa. Increasing the level of bis-M6P on alglucosidase alfa may provide a mechanism to drive uptake into the skeletal muscle and thereby improve outcomes in IOPD and LOPD.

The methods described herein are suitable for treating human individuals having IOPD. In some embodiments, the individual has cardiomyopathy at the time of diagnosis in the first year of life. In some embodiments, the individual has hypertrophic cardiomyopathy at the time of diagnosis in the first year of life. In some embodiments, the individual has arrhythmia at the time of diagnosis in the first year of life. In some embodiments, the individual has cardiomegaly at the time of diagnosis in the first year of life. In some embodiments, the individual has severe hypotonia at the time of diagnosis in the first year of life. In some embodiments, the individual has severe myopathy at the time of diagnosis in the first year of life.

In some embodiments, the individual is 18 years old or younger. In particular embodiments, the individual is 17 years old or younger, 16 years old or younger, 15 years old or younger, 14 years old or younger, 13 years old or younger, 12 years old or younger, 11 years old or younger, 10 years old or younger, 9 years old or younger, 8 years old or younger, 7 years old or younger, 6 years old or younger, 5 years old or younger, 4 years old or younger, 3 years old or younger, 2 years old or younger or 1 year old or younger. In some embodiments, the individual is greater than 18 years old. In some embodiments, the individual is 11 months old or younger, 10 months old or younger, 9 months old or younger, 8 months old or younger, 7 months old or younger, 6 months old or younger, 5 months old or younger, 4 months old or younger, 3 months old or younger, 2 months old or younger or younger than 1 month old. In some embodiments, the individual is a new born. In some embodiments, the individual is about any one of 0-1 months old, 0-2 months old, 0-3 months old, 0-4 months old, 0-5 months old, 0-6 months old, 1-6 months old, 2-6 months old, 3-6 months old, 4-6 months old, 5-6 months old, 2-4 months old, 3-6 months old, or 4-6 months old. In some embodiments, the individual is first administered with the oligosaccharide-GAA conjugate within the first month of life. In some embodiments, the individual is administered an immune induction therapy (e.g., methotrexate, rituximab and IVIG) within the first month of life.

In some embodiments, the individual has received at least 6 months of treatment with a recombinant GAA. In some embodiments, the individual has received at least about any one of 8 months, 10 months, 1 year, 2 years, 3 years, 4 years, 5 years, 10 years or more, including any value or range in between these values, of treatment with a recombinant GAA. In other embodiments, the individual has not received treatment with a recombinant GAA. Exemplary recombinant GAA include, but are not limited to, alglucosidase alfa, reveglucosidase alfa (BioMarin), and ATB200 (Amicus).

In some embodiments, the individual shows clinical decline after treatment with the recombinant GAA, wherein the clinical decline is determined by assessing one or more parameters selected from the group consisting of respiratory functions, motor skills and cardiac parameters. In some embodiments, the individual has suboptimal clinical response to treatment with the recombinant GAA. A suboptimal clinical response may be determined by assessing respiratory functions, motor skills, or cardiac parameters. Respiratory functions, motor skills, and/or cardiac parameters can be assessed by CK level, urinary Hex4 level, GMFM-88, Alberta Infant Motor Scale (AIMS) score, Pompe-Pediatric Evaluation of Disability Inventory (PEDI) functional skills scale, Echocardiographic (ECHO)-left ventricular mass (LVM) Z-score, ECHO LVMI score, Gross Motor Function Classification System-Expanded and Revised (GMFCS-E&R) score, Quick Motor Function Test, 6 Minute Walk test (6MWT), onset of ptosis, interpalpebral fissure distance (IPFD), margin reflex distance-1 (MRD-1), and margin pupil distance (MPD), and/or use of respiratory support.

In some embodiments, the individual is cross-reactive immunologic material (CRIM)-negative. CRIM negative patients do not produce any GAA enzyme, and as a result may produce high levels of neutralizing antibodies to a GAA ERT (Dasouki, M. et al. *Neurol Clin.* 2014 32:3). In other embodiments, the individual is CRIM-positive. CRIM-positive patients have some residual GAA activity. CRIM status may be determined by a by Western blot analysis from cultured skin fibroblasts, predicted from GAA gene mutations, or determined from a blood test (Burton, B. K. et al. *Pediatrics* 2017 140:s1; Bali, D. S. et al., *Am J Med Genet C Semin Med Genet.* 2012 15:160C; Wang, Z. et al. *Mol Genet Metab.* 2014 111:2).

B. Oligosaccharide-Protein Conjugate

The methods described herein use oligosaccharide-protein conjugates (also referred herein as "oligosaccharide GAA conjugates") comprising an oligosaccharide, a GAA (also known as acid α-glucosidase), and a chemical linker connecting the oligosaccharide and the GAA, e.g., via an oxime group. In some embodiments, the oligosaccharide is a hexasaccharide. In some embodiments, the oligosaccharide has two mannose-6-phosphate (M6P). In some embodiments, the oligosaccharide-protein conjugate has about any one of 2, 4, 6, 8, 10, 12, 14, 16, 18, 20 or more M6P, including any value or range between these values. In some embodiments, the oligosaccharide-protein conjugate is avalglucosidase alfa.

In some embodiments, described herein is an oligosaccharide-protein conjugate comprising (1) a GAA protein, (2) an oligosaccharide, and (3) an oxime group connecting the GAA protein and the oligosaccharide.

In some embodiments, the oligosaccharide-protein conjugate has a structure of Formula (I):

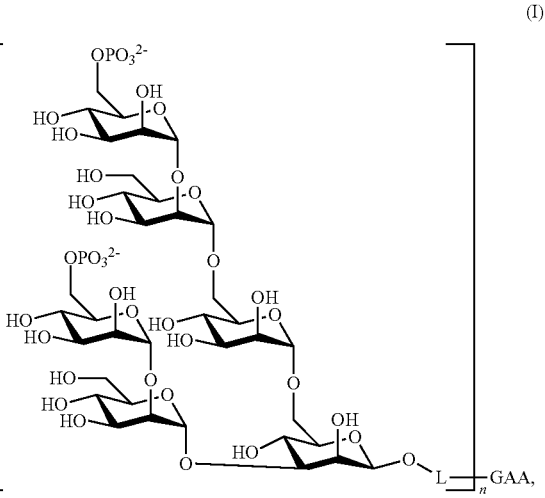

wherein GAA is acid α-glucosidase, L is a chemical linker connecting the oligosaccharide and the GAA, and n is 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is at least 1, 2, 3, 4, 5, 6, 7, 8, or 9. In some embodiments, n is no more than 2, 3, 4, 5, 6, 7, 8, 9, or 10. In some embodiments, n is selected from the following ranges: 1-2, 2-3, 3-4, 4-5, 5-6, 6-7, 7-8, 8-9, 9-10, 1-3, 3-5, 5-7, 7-9, 1-4, 4-7, 7-10, 1-5, 5-10, 2-10, 3-9, 4-8, 2-9, 3-8, 4-7, 5-8, 5-9, 5-10, 4-7, 3-7, 2-7, and 1-7. In some embodiments, n is 5-9.

In some embodiments, the oligosaccharide-protein conjugate has a structure of Formula (II):

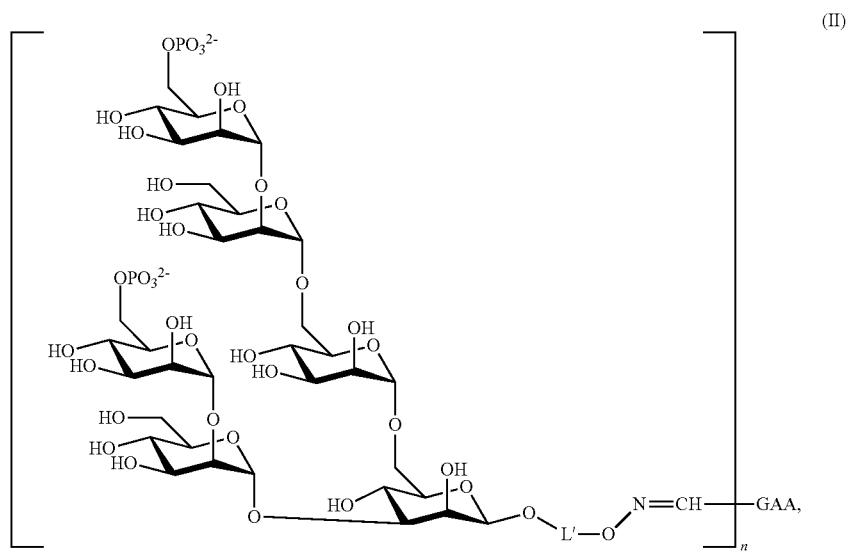

wherein GAA is acid α-glucosidase, L' is a chemical linker, and n is 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is at least 1, 2, 3, 4, 5, 6, 7, 8, or 9. In some embodiments, n is no more than 2, 3, 4, 5, 6, 7, 8, 9, or 10. In some embodiments, n is selected from the following ranges: 1-2, 2-3, 3-4, 4-5, 5-6, 6-7, 7-8, 8-9, 9-10, 1-3, 3-5, 5-7, 7-9, 1-4, 4-7, 7-10, 1-5, 5-10, 2-10, 3-9, 4-8, 2-9, 3-8, 4-7, 5-8, 5-9, 5-10, 4-7, 3-7, 2-7, and 1-7. In some embodiments, n is 5-9.

In some embodiments, the oligosaccharide-protein conjugate has a structure of Formula (III):

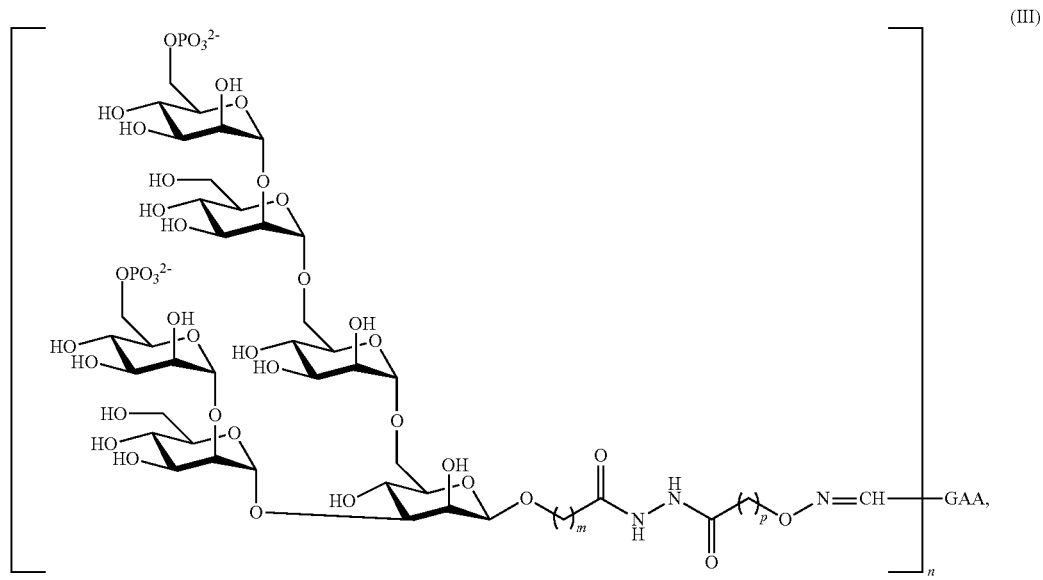

wherein GAA is acid α-glucosidase, n is 1 to 10, and m and p are independently chosen from integers ranging from 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is at least 1, 2, 3, 4, 5, 6, 7, 8, or 9. In some embodiments, n is no more than 2, 3, 4, 5, 6, 7, 8, 9, or 10. In some embodiments, n is selected from the following ranges: 1-2, 2-3, 3-4, 4-5, 5-6, 6-7, 7-8, 8-9, 9-10, 1-3, 3-5, 5-7, 7-9, 1-4, 4-7, 7-10, 1-5, 5-10, 2-10, 3-9, 4-8, 2-9, 3-8, 4-7, 5-8, 5-9, 5-10, 4-7, 3-7, 2-7, and 1-7. In some embodiments, n is 5-9. In some embodiments, m is 1, 2, 3, 4, 5, 6, 7, 8, or 9, or 10. In some embodiments, p is 1, 2, 3, 4, 5, 6, 7, 8, 9, or 10. In some embodiments, m and p are independently chosen from integers selected from the following ranges: 1-4, 4-8, 8-10, 2-4, 2-6, 2-8, 2-10, 1-3, 3-6, 6-9, and 4-10. In some embodiments, m and p are independently chosen from integers ranging from 1 to 5. In some embodiments, m is 1, 2, 3, 4, or 5 and p is 1, 2, 3, 4, or 5. In some embodiments, m is 1, 2, or 3 and p is 1, 2, or 3. In some embodiments, m is 5 and p is 1. In some embodiments, m is 4 and p is 1. In some embodiments, m is 3 and p is 1. In some embodiments, m is 2 and p is 1. In some embodiments, m is 1 and p is 1. In some embodiments, m is no more than 5, and p is no more than 3. In some embodiments, m is no more than 4, and p is no more than 2. In some embodiments, m is no more than 3, and p is no more than 1. In some embodiments, m is at least 1, and p is at least 1. In some embodiments, m is at least 2, and p is at least 1. In some embodiments, m is at least 3, and p is at least 1.

In some embodiments, the number of phosphate groups per oligosaccharide-protein conjugate (e.g., conjugate of formula (I), (II), or (III)] is about 2-20. In some embodiments, the number of phosphate groups per oligosaccharide-protein conjugate is 2, 4, 6, 8, 10, 12, 14, 16, 18, or 20. In some embodiments, the number of phosphate groups per oligosaccharide-protein conjugate is at least 2, 4, 6, 8, 10, 12, 14, 16, 18, or 20. In some embodiments, the number of phosphate groups per oligosaccharide-protein conjugate is no more than 2, 4, 6, 8, 10, 12, 14, 16, 18, or 20. In some embodiments, the number of phosphate groups per oligosaccharide-protein conjugate is an even integer selected from the following ranges: 2-4, 4-6, 6-8, 8-10, 10-12, 12-14, 14-16, 16-18, 18-20, 2-6, 6-10, 10-14, 14-18, 2-8, 8-14, 14-20, 2-10, 10-20, 4-20, 6-18, 8-16, 4-18, 6-16, 8-14, 10-16, 10-18, 10-20, 8-14, 6-14, 4-14, and 2-14.

In some embodiments, the oligosaccharide-protein conjugate is avalglucosidase alfa. Avalglucosidase alfa is also known as neoGAA or GZ402666. Avalglucosidase alfa is an oligosaccharide-modified form of human GAA, comprising a number of hexamannose structures containing two terminal mannose-6-phosphate (M6P) moieties conjugated to the GAA.

Methods of preparing the oligosaccharide-protein conjugates described herein are known in the art. See, for example, U.S. Pat. No. 7,723,296, WO2008/089403 and WO2010/075010, which are incorporated herein by reference in their entirety.

The oligosaccharide may be isolated from a natural source or may be prepared by chemical or enzymatic synthesis. An oligosaccharide isolated from a natural source may be homogeneous or may be a heterogeneous mixture of related oligosaccharides. In some embodiments, an oligosaccharide may be prepared by chemical or enzymatic modification of an oligosaccharide isolated from a natural source ("semi-synthesis"). In some embodiments, the oligosaccharide may be a synthetic oligosaccharide having the chemical structure of a naturally occurring oligosaccharide.

The sequence of GAA is well known (see, e.g., Martiniuk et al., *Proc. Natl. Acad. Sci. USA* 83:9641-9644 (1986); Hoefsloot et al., *Biochem.* 1 272:493-497 (1990); Moreland et al., *J. Biol. Chem.* 280:6780-6791 (2005). See also GenBank Accession No. NM_000152. The GAA may be a wildtype GAA or a sequence variant thereof.

The GAA may be obtained from a natural source, or recombinantly. In some embodiments, the GAA is a glycoprotein. In some embodiments, the GAA is a human GAA produced in Chinese hamster ovary (CHO) cells. In some embodiments, the human GAA has glycoform alfa. In some embodiments, the GAA has at least one carbonyl group. For example, a GAA having at least one carbonyl group may be obtained by oxidation of the GAA by any means known to those of skill in the art. In some embodiments, e.g., a GAA having at least one carbonyl group may be obtained by oxidation of the GAA with periodate (e.g., sodium periodate) or galactose oxidase. In some embodiments, the GAA having at least one carbonyl group may be chemically conjugated with an oligosaccharide functionalized at the reducing end with a carbonyl-reactive group (such as, e.g., a hydrazine, hydrazide, aminooxy, thiosemicarbazide, semicarbazide, or amine group) to yield an oligosaccharide-GAA conjugate. In some embodiments, the GAA is oxidized with about 1, 2, 3, 4, 5, 7.5, 10, or 22.5 mM periodate. In some embodiments, the GAA is oxidized under conditions sufficient to oxidize sialic acid residues on the glycans of the GAA, and minimize fucose and mannose oxidation. In some embodiments, the periodate concentration used in less than about 2, 3, 4, or 5 mM. In some embodiments, the periodate is sodium periodate.

Other methods of conjugating the oligosaccharide to the GAA protein may be used. In some embodiment, the oligosaccharide-protein conjugate is prepared by reacting an oligosaccharide comprising a first reactive group with a GAA protein having a second reactive group. In some embodiments, the oligosaccharide-protein conjugate is prepared by reacting an oligosaccharide comprising an aminooxy group with a GAA having at least one carbonyl group.

In some embodiments, the oligosaccharide may be conjugated to an amino acid of the GAA protein, such as a cysteine or lysine.

In some embodiments, the oligosaccharide can be conjugated to a glycan on the GAA. In some embodiments, the oligosaccharide may be conjugated to a sialic acid residue on a glycan. In other embodiments, the oligosaccharide may be conjugated to mannose, fucose, galactose, and/or sialic acid residues on a glycan. For conjugation through galactose, the glycoprotein may first be treated with sialidase to remove sialic acid residues, then treated with galactose oxidase prior to reaction with the oligosaccharide.

For example, the oligosaccharide-protein conjugate may be prepared by reaction of any functional group that may be present (including, e.g., an amine, a thiol, a carboxylic acid, a hydroxyl) and/or introduced into a protein with a suitable second functional group on an oligosaccharide. Methods for the introduction of functional groups are well known in the art. For example, a glycoprotein having at least one carbonyl group may be obtained by oxidation of that glycoprotein with, e.g., periodate (e.g., sodium periodate) or with galactose oxidase. In another example, a carbonyl group may be introduced by use of an expression system having an expanded genetic code, as described in, e.g., Wang et al., *Proc. Natl. Acad. Sci. USA* 100:56-61 (2003). See also, e.g., U.S. Patent Application Pub. No. 2006/0228348, which describes the introduction of reactive groups into a glycoprotein.

In certain embodiments, the methods further comprise adding a reducing agent to the oligosaccharide-protein conjugate. The reducing agent may be any reducing agent known to those of skill in the art, such as, e.g., sodium cyanoborohydride or sodium triacetoxyborohydride (STAB).

In certain embodiments, protein aggregates that form during conjugation can be removed using various chromatography methods. In one embodiment, hydrophobic interaction chromatography (HIC) may be employed. Examples of HIC columns include Butyl 650C and 650M, Hexyl 650C, Phenyl 6FF, Capto Octyl and Capto Phenyl. In other embodiments, aggregates may be removed by metal chelation chromatography, such as copper, nickel, cobalt, or mercury. In one embodiment, a copper column can be used in bind-and-elute or in flow-through mode.

In some embodiments, the oligosaccharide comprising a first reactive group is an oligosaccharide comprising an aminooxy group and has a structure of Formula (IV):

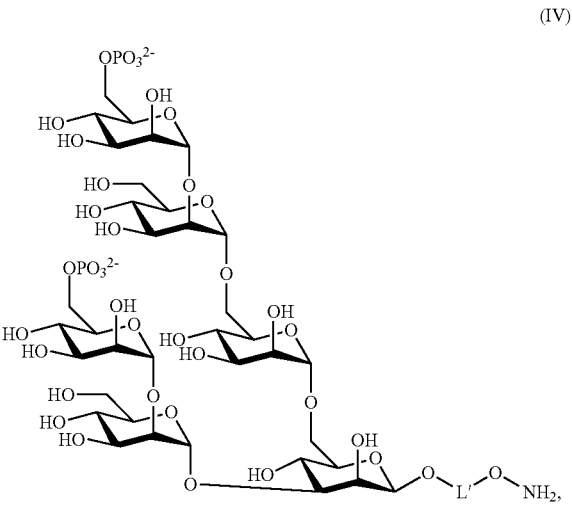

(IV)

wherein L' is a chemical linker.

In some embodiments, the oligosaccharide of Formula (III) is an oligosaccharide of Formula (V):

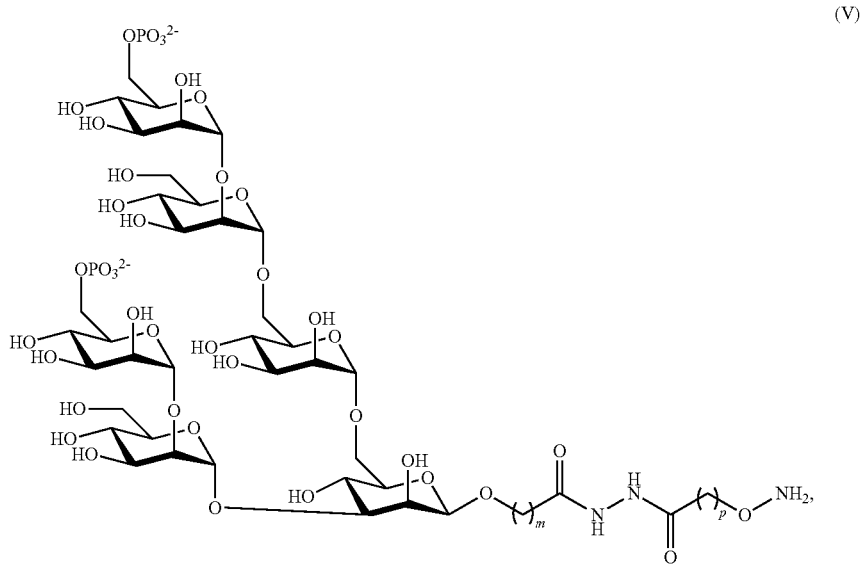

(V)

wherein m and p are independently chosen from integers ranging from 1 to 10. In some embodiments, m is 1, 2, 3, 4, 5, 6, 7, 8, 9, or 10. In some embodiments, p is 1, 2, 3, 4, 5, 6, 7, 8, 9, or 10. In some embodiments, p is at least 1, 2, 3, 4, 5, 6, 7, 8, 9, or 10. In some embodiments, m and p are independently chosen from integers selected from the following ranges: 1-4, 4-8, 8-10, 2-4, 2-6, 2-8, 2-10, 1-3, 3-6, 6-9, and 4-10. In some embodiments, m and p are independently chosen from integers ranging from 1 to 5. In some embodiments, m is 1, 2, 3, 4, or 5 and p is 1, 2, 3, 4, or 5. In some embodiments, m is 1, 2, or 3 and p is 1, 2, or 3. In some embodiments, m is 5 and p is 1. In some embodiments, m is 4 and p is 1. In some embodiments, m is 3 and p is 1. In some embodiments, m is 2 and p is 1. In some embodiments, m is 1 and p is 1. In some embodiments, m is no more than 5, and p is no more than 3. In some embodiments, m is no more than 4, and p is no more than 2. In some embodiments, m is no more than 3, and p is no more than 1. In some embodiments, m is at least 1, and p is at least 1. In some embodiments, m is at least 2, and p is at least 1. In some embodiments, m is at least 3, and p is at least 1.

C. Immune Tolerance Induction Therapy

Any one of the methods described herein may further comprise administration of an immune tolerance induction therapy. In some embodiments, the immune tolerance induction therapy comprises methotrexate. In some embodiments, the immune tolerance induction therapy comprises methotrexate and additional immune tolerance induction therapy. In some embodiments, the immune tolerance induction therapy comprises methotrexate, rituximab, and IVIG. In some embodiments, the immune tolerance induction therapy is for prophylactic use.

In some embodiments, the method further comprises administering to the individual an effective amount of methotrexate. In some embodiments, the methotrexate is used to induce immune tolerance to the oligosaccharide-GAA conjugate described herein (e.g., Formulae I-III, or avalglucosidase alfa) in the individual. Any of the available dosing regimens can be used to induce immune tolerance, including continuous weekly repeat doses regimen (Garman et al. Clin Exp Immunol, 137(3):496-502 (2004); Joseph et al, Clin Exp Immunol, 152(1): 138-46 (2008); Mendelsohn et al, N Engl J Med, 360(2): 194-5 (2009)), and transient low-dose regimens (See U.S. Patent Publication No. 20140135337). In some embodiments, the effective amount of methotrexate is administered in three cycles. In some embodiments, the methotrexate is administered in a single cycle. In some embodiments, the methotrexate is administered in one, two, three, four, five or more cycles.

As used herein, a single cycle refers to a treatment regimen, or a treatment unit, of consecutive or non-consecutive days and is started at preferably no more than five (e.g., no more than three) days following the dosing of the oligosaccharide-GAA conjugate. A single cycle of methotrexate may consist of a single dose of methotrexate, or about any one of 2, 3, 4, 5, 6, 7, 8, 9, 10, or 11 consecutive daily doses of methotrexate. If the oligosaccharide-GAA conjugate is dosed in multiple periods, a single cycle of treatment with methotrexate preferably does not extend past the first period of the oligosaccharide-GAA conjugate dosing. By way of example, in a weekly, monthly, or annual oligosaccharide-GAA conjugate administration, a single cycle of methotrexate consists of three consecutive days of methotrexate intake (e.g., orally), starting on day 0, the day when the oligosaccharide-GAA conjugate is given to the patient for the first time. Then the patient receives a single dose of methotrexate on day 1 (about 24 hours later) and on day 2 (about 48 hours later). In some embodiments, a single cycle of methotrexate does not last longer than about 8 days.

Methotrexate and the oligosaccharide-GAA conjugate can be administered in any order deemed appropriate. For example, the methotrexate can be administered to the subject before, during, and/or after administration of the oligosaccharide-GAA conjugate. In some embodiments, the methotrexate is administered between about 48 hours prior to and about 48 hours after the administration of the oligosaccharide-GAA conjugate. For example, the methotrexate may be administered about any one of 48 hours prior to, 36 hours prior to, 24 hours prior to, 12 hours prior to, concurrently with, 12 hours after, 24 hours after, 36 hours after, or 48 hours after the administration of the oligosaccharide-GAA conjugate treatment. In some embodiments, the methotrexate is administered concurrently with the oligosaccharide-GAA conjugate. In some embodiments, the methotrexate is administered concurrently with administration of the oligosaccharide-GAA conjugate, and about 24 and about 48 hours after administration of the oligosaccharide-GAA conjugate. In some embodiments, the oligosaccharide-GAA conjugate is alglucosidase alfa, and the methotrexate is administered concurrently with administration of the oligosaccharide-GAA conjugate and about 24 and about 48 hours after administration of the oligosaccharide-GAA conjugate.

Methotrexate can be administered at any dose effective in reducing undesired immunological responses, such as antibody or cellular responses. An effective amount of methotrexate in human patients may be in the range of about 0.05 mg/kg to about 10 mg/kg, such as no more than about any one of 0.1 mg/kg, 0.2 mg/kg, 0.3 mg/kg, 0.4 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7.5 mg/kg, or 10 mg/kg. In some embodiments, the effective amount is any one of about 0.1 mg/kg to about 1.5 mg/kg, about 0.12 mg/kg to about 1.28 mg/kg, about 1 mg/kg to about 2.5 mg/kg, or about 2.5 mg/kg to about 5 mg/kg, or about 0.1 mg/kg to about 5 mg/kg. In some embodiments, the dosage of methotrexate may pose minimal safety risks because the dosing regimen involves only a brief course of methotrexate at dose levels that are more similar to doses for rheumatoid arthritis than low neoplastic doses. Rheumatoid arthritis patients can receive up to 25 mg of methotrexate per week without suffering from significant toxicities. The low neoplastic dose of methotrexate is considered to be 30 mg/m$^2$.

In some embodiments, methotrexate is administered in more than one cycle, but at a low total dosage. For instance, the methotrexate can be administered in two or more (e.g., 3, 4, 5, 6, etc.) cycles, but with a total combined dosage of no more than 5 mg/kg in a patient.

In some embodiments, in addition to methotrexate, the subject is administered an additional immune tolerance induction therapy concurrently with the administration of any one of the oligosaccharide-GAA conjugates described herein (e.g., Formulae I-III, or avalglucosidase alfa). In some embodiments, the methotrexate and/or the additional immune tolerance induction therapy are administered to the individual upon initiation of the oligosaccharide-GAA conjugate as opposed to immune tolerance induction therapy administered in further cycles of treatment with the oligosaccharide-GAA conjugate. In some embodiments, the methotrexate and/or the additional immune tolerance induction therapy are administered to the individual upon initiation of the oligosaccharide-GAA conjugate and in one or more further cycles of treatment with the oligosaccharide-GAA conjugate. In some embodiments, the additional immune tolerance induction therapy is administered concurrently with methotrexate. In some embodiments, the additional immune tolerance induction therapy is administered after administration of methotrexate, such as after any one of 1, 2, 3, 4, 5, 6, 7 days or more after administration of methotrexate. In some embodiments, the additional immune tolerance induction therapy is administered before administration of methotrexate, such as any one of 1, 2, 3, 4, 5, 6, 7 days or more before administration of methotrexate. In some embodiments, the subject has CRIM-negative IOPD.

In some embodiments, the subject has CRIM-positive IOPD. In some embodiments, methotrexate is administered enterally. In some embodiments, methotrexate is administered at a dose of about 0.5 mg/kg. In some embodiments, methotrexate is administered weekly. In some embodiments, methotrexate is administered subcutaneously. In some embodiments, methotrexate is administered at a dose of about 0.4 mg/kg. In some embodiments, methotrexate is administered at three doses per week for three weeks.

In some embodiments, the additional immune tolerance induction therapy comprises rituximab, intravenous immunoglobulin (IVIG), or combination thereof. In some embodiments, the additional immune tolerance induction therapy comprises administration of rituximab. In some embodiments, rituximab is administered at a dose of about 375 mg/m$^2$. In some embodiments, such as when the body surface area (BSA) of the subject is less than 0.5 m$^2$, rituximab is administered at a dose of about 12.5 mg/kg. In some embodiments, rituximab is administered intravenously. In some embodiments, rituximab is administered weekly. In some embodiments, the additional immune tolerance induction therapy comprises administration of IVIG. In some embodiments, IVIG is administered at a dose of about 0.5 g/kg. In some embodiments, IVIG is administered at a dose of about 400-500 mg/kg. In some embodiments, IVIG is administered about every four weeks. In some embodiments, IVIG is administered monthly. In some embodiments, the additional immune tolerance induction therapy comprises administration of both rituximab and IVIG.

Figure 12:
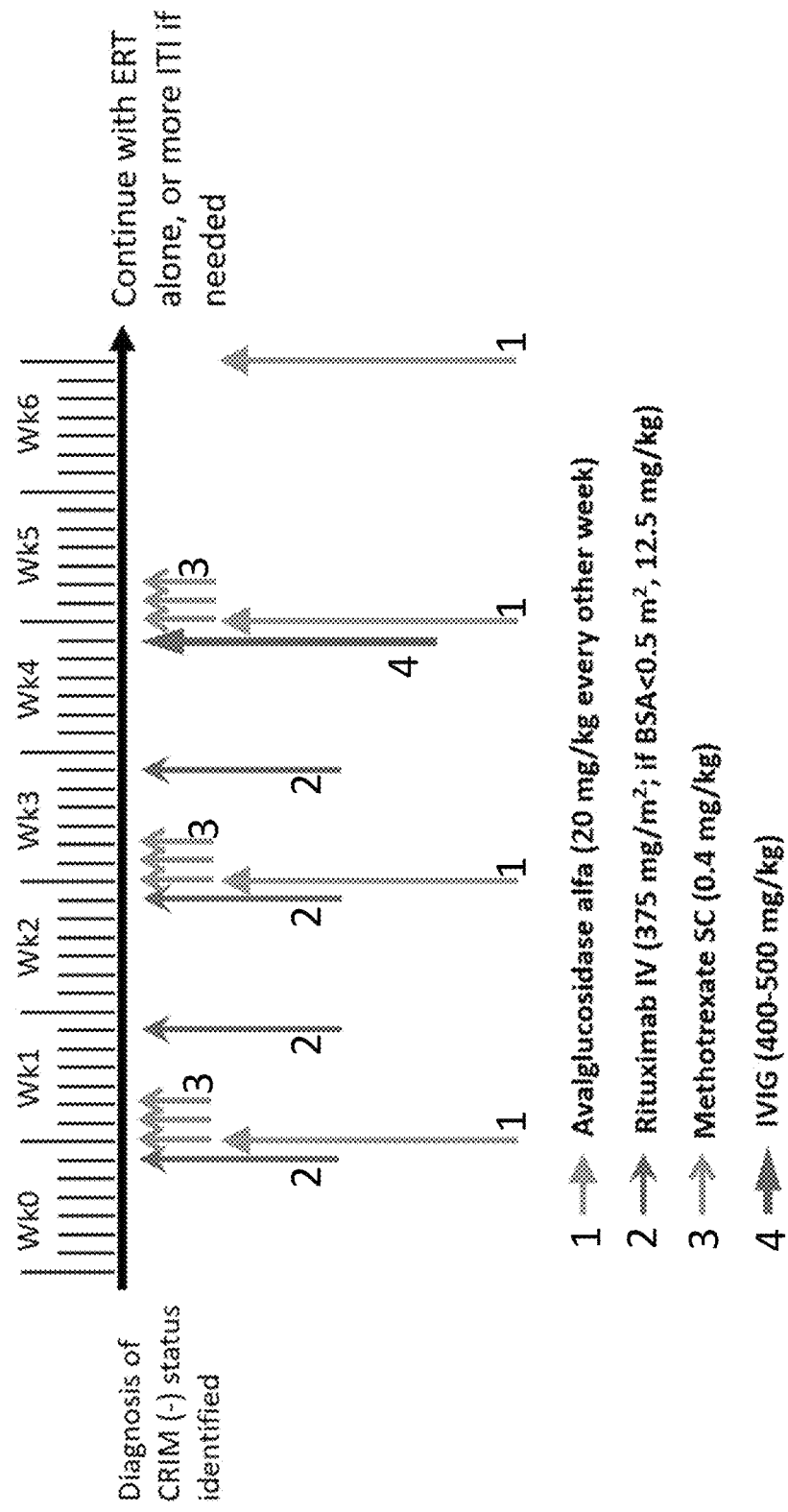
FIG. 12 shows an exemplary dosage regimen for CRIM-negative patients. ERT: enzyme replacement therapy; ITI.

In some embodiments, the method comprises: (a) administering to the individual an effective amount of any one of the oligosaccharide-GAA conjugates described herein (e.g., Formulae I-III, or avalglucosidase alfa); and (b) administering to the individual an effective amount of methotrexate, an effective amount of rituximab and an effective amount of IVIG. In some embodiments, the oligosaccharide-GAA conjugate is administered at about 20 mg/kg every other week. In some embodiments, the methotrexate is administered subcutaneously. In some embodiments, the methotrexate is administered at about 0.4 mg/kg. In some embodiments, the methotrexate is administered at three doses per week for three weeks. In some embodiments, the rituximab is administered at about 375 mg/m$^2$. In some embodiments, such as when the body surface area (BSA) of the subject is less than 0.5 m$^2$, rituximab is administered at a dose of about 12.5 mg/kg. In some embodiments, rituximab is administered intravenously. In some embodiments, rituximab is administered weekly. In some embodiments, IVIG is administered at a dose of about 400-500 mg/kg. In some embodiments, IVIG is administered about every four weeks. In some embodiments, the dosage regimen of the oligosaccharide-GAA conjugate, methotrexate, rituximab and IVIG is as shown in FIG. 12.

The effect of methotrexate and the additional immune tolerance induction therapy on managing undesired antibody responses in the patient can be monitored by well-known methods, including clinical examination of the patient, symptoms, blood tests assaying anti-drug antibody titers, and immunohistochemical assays (e.g., C4 deposition assays and other solid-phase antibody detection methods such as the enzyme-linked immunosorbent assay (ELISA) and bead-based flurometric assays). The effect also can be monitored by measuring levels of biomarkers such as MCP-1, IL-13, IL-6, and IL-12, whose levels have been shown to be reduced by methotrexate treatment, and transitional 2 B cells, transitional 3 B cells, follicular B cells, marginal zone B cells, B10 B cells, and B1 B cells, whose numbers have been shown to be increased by methotrexate treatment. Additionally, TGF-beta, FoxP3, IL-5, IL-10, IL-15, and GM-CSF may be used as biomarkers to monitor the effects of methotrexate on undesired immune responses as needed. The levels of biomarkers also may be used to monitor the effects of methotrexate on T cell responsiveness to the oligosaccharide-GAA conjugate. Biomarkers for T cell activation such as IL-2, interferon-γ, and TNF-α, may also be monitored as readouts for methotrexate's effect on T cell responses. In some embodiments, the level of CD19 is further detected to monitor undesirable immune response. In some embodiments, the individual is monitored throughout the treatment for one or more of anti-drug antibody level (such as anti-rhGAA IgG antibody level), CD19 level, and disease progression.

III. Formulations and Pharmaceutical Compositions

Further provided are formulations and pharmaceutical compositions comprising any one of the oligosaccharide-GAA conjugates described herein (e.g., Formulae I-III, or avalglucosidase alfa). In some embodiments, the formulation is a lyophilized formulation. In some embodiments, the formulation is a lyophilizable formulation. In some embodiments, the pharmaceutical composition is reconstituted from the lyophilized formulation. Also provided are methods and use of the formulations and pharmaceutical compositions described herein for treating Pompe disease, such as IOPD.

The oligosaccharide-GAA conjugates described herein is unstable in liquid formulation when storage over an extended period of time. Without being bound by any theory or hypothesis, the chemical linkage between the oligosaccharide moiety and the GAA protein may be subject to degradation in a liquid formulation. Lyophilization formulations are developed to allow storage of the oligosaccharide-GAA conjugates in the dry powder form, and reconstituted into a liquid formulation prior to administration to the patients. Previous attempts to formulate recombinant GAA as lyophilized formulation were unsuccessful and resulted in aggregation upon reconstitution because GAA is an enzyme that can break down sugar moieties commonly used as cryoprotectants in lyophilized or lyophilizable formulations. The lyophilized formulations described herein comprise one or more cryoprotectants such as mannitol that are not subject to degradation by GAA.

In some embodiments, there is provided a formulation comprising: (a) any one of the oligosaccharide-GAA conjugates described herein (e.g., Formulae I-III, or avalglucosidase alfa); and (b) a sugar that is not degraded by the GAA. In some embodiments, there is provided a formulation comprising: (a) any one of the oligosaccharide-GAA conjugates described herein (e.g., Formulae I-III, or avalglucosidase alfa); (b) a sugar that is not degraded by the GAA; and (c) a buffering agent. In some embodiments, the sugar is mannitol. In some embodiments, the buffering agent is histidine. In some embodiments, the formulation further comprises one or more stabilizing agents, such as glycine or arginine. In some embodiments, the formulation further comprises a surfactant, such as polysorbate, e.g., polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation.

In some embodiments, there is provided a lyophilized or lyophilizable formulation comprising: (a) any one of the oligosaccharide-GAA conjugates described herein (e.g., Formulae I-III, or avalglucosidase alfa); and (b) one or more cryoprotectants comprising a sugar that is not degraded by the GAA. In some embodiments, there is provided a lyophilized or lyophilizable formulation comprising: (a) any one of the oligosaccharide-GAA conjugates described herein (e.g., Formulae I-III, or avalglucosidase alfa); (b) (b) one or more cryoprotectants comprising a sugar that is not degraded by the GAA; and (c) a buffering agent. In some embodiments, the one or more cryoprotectants comprise mannitol. In some embodiments, the one or more cryoprotectants comprise glycine and mannitol. In some embodiments, the one or more cryoprotectants comprise arginine and mannitol. In some embodiments, the one or more cryoprotectants further comprises a surfactant, such as polysorbate, e.g., polysorbate 80. In some embodiments, the buffering agent is histidine. In some embodiments, the formulation is a lyophilized formulation. In some embodiments, the formulation is a lyophilizable formulation. In some embodiments, there is provided a pharmaceutical composition that is reconstituted from the lyophilized formulation.

In some embodiments, there is provided a formulation comprising: (a) any one of the oligosaccharide-GAA conjugates described herein (e.g., Formulae I-III, or avalglucosidase alfa); (b) mannitol; and (c) a buffering agent, such as histidine. In some embodiments, the formulation further comprises a surfactant, such as polysorbate, e.g., polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation.

In some embodiments, there is provided a formulation comprising: (a) any one of the oligosaccharide-GAA conjugates described herein (e.g., Formulae I-III, or avalglucosidase alfa); (b) mannitol; and (c) a buffering agent, such as histidine. In some embodiments, the formulation further comprises a surfactant, such as polysorbate, e.g., polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation.

In some embodiments, there is provided a formulation comprising: (a) any one of the oligosaccharide-GAA conjugates described herein (e.g., Formulae I-III, or avalglucosidase alfa); (b) mannitol; (c) glycine; and (d) a buffering agent, such as histidine. In some embodiments, the formulation further comprises a surfactant, such as polysorbate, e.g., polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation.

In some embodiments, there is provided a formulation comprising: (a) any one of the oligosaccharide-GAA conjugates described herein (e.g., Formulae I-III, or avalglucosidase alfa); (b) mannitol; (c) arginine; and (d) a buffering agent, such as histidine. In some embodiments, the formulation further comprises a surfactant, such as polysorbate, e.g., polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation.

In some embodiments, there is provided a formulation comprising: (a) any one of the oligosaccharide-GAA conjugates described herein (e.g., Formulae I-III, or avalglucosidase alfa); (b) mannitol; (c) glycine; and (d) histidine. In some embodiments, there is provided a formulation comprising: (a) any one of the oligosaccharide-GAA conjugates described herein (e.g., Formulae I-III, or avalglucosidase alfa); (b) mannitol; (c) glycine; (d) histidine; and (e) polysorbate (e.g., polysorbate 80). In some embodiments, the formulation is a lyophilized formulation. In some embodiments, the formulation is a lyophilizable formulation. In some embodiments, there is provided a pharmaceutical composition that is reconstituted from the lyophilized formulation.

Unless indicated otherwise, the percentage concentrations described herein are weight-by-weight percentages. When referring to concentrations of the oligosaccharide-GAA conjugate or various excipients in a lyophilized formulation, the concentrations are determined in the composition prior to lyophilization (i.e., in a lyophilizable formulation), or after reconstitution of the lyophilized formulation. The pH of a lyophilized formulation also refers to the pH of the composition prior to lyophilization (i.e., in a lyophilizable formulation), or after reconstitution of the lyophilized formulation.

In some embodiments, the formulation comprises about 1% to about 5% of the sugar that is not degraded by the GAA, including for example, about any one of 1%, 1.5%, 2%, 2.5%, 3%, 3.5%, 4%, 4.5%, or 5% of the sugar, including any value or range between these values. In some embodiments, the formulation comprises about any one of 1%-2%, 2%-3%, 3%-4%, 4%-5%, 1%-3%, 2%-4%, 1%-4% or 1%-5% of the sugar. In some embodiments, the formulation comprises about 2% of the sugar.

In some embodiments, the formulation comprises about 1% to about 5% of mannitol, including for example, about any one of 1%, 1.5%, 2%, 2.5%, 3%, 3.5%, 4%, 4.5%, or 5% of mannitol, including any value or range between these values. In some embodiments, the formulation comprises about any one of 1%-2%, 2%-3%, 3%-4%, 4%-5%, 1%-3%, 2%-4%, 1%-4% or 1%-5% of mannitol. In some embodiments, the formulation comprises about 1-4% mannitol. In some embodiments, the formulation comprises about 2% mannitol.

In some embodiments, the formulation comprises about 0.5% to about 4% of an amino acid (e.g., arginine), including for example, about any one of 0.5%, 1%, 1.5%, 2%, 2.5%, 3%, 3.5%, or 4% of the amino acid, including any value or range between these values. In some embodiments, the formulation comprises about any one of 0.5%-1%, 1%-2%, 2%-3%, 3%-4%, 1%-3%, 2%-4%, or 1%-4% of the amino acid.

In some embodiments, the formulation comprises about 0.25% to about 4% of glycine, including for example, about any one of 0.25%, 0.5%, 1%, 1.5%, 2%, 2.5%, 3%, 3.5%, or 4% of the sugar, including any value or range between these values. In some embodiments, the formulation comprises about any one of 0.25%-0.5%, 0.5%-1%, 1%-2%, 2%-3%, 3%-4%, 1%-3%, 2%-4%, 0.25%-1%, 0.25%-1.5%, or 0.25%-2% of glycine. In some embodiments, the formulation comprises about 0.25%-2% glycine. In some embodiments, the formulation comprises about 2% glycine.

In some embodiments, the formulation comprises mannitol and an amino acid (e.g., arginine or glycine) at a weight ratio of about any one of 16:1, 8:1, 4:1, 2:1, 1:1, 1:2, 1:3, 1:4 or 1:5, including any value or range between these values. In some embodiments, the formulation comprises mannitol and glycine at a weight ratio of about 1:1.

In some embodiments, the formulation comprises about 5 mM to about 50 mM buffering agent, including for example, about any one of 5 mM, 10 mM, 15 mM, 20 mM, 25 mM, 30 mM, 35 mM, 40 mM, 45 mM or 50 mM, including any value or range between these values. In some embodiments, the formulation comprises about any one of 5-10 mM, 10-20 mM, 20-30 mM, 30-40 mM, 40-50 mM, 5-20 mM, 10-40 mM, 10-50 mM, 5-25 mM, or 25-50 mM of the buffering agent.

In some embodiments, the formulation comprises about 5 mM to about 50 mM histidine, including for example, about any one of 5 mM, 10 mM, 15 mM, 20 mM, 25 mM, 30 mM, 35 mM, 40 mM, 45 mM or 50 mM, including any value or range between these values. In some embodiments, the formulation comprises about any one of 5-10 mM, 10-20 mM, 20-30 mM, 30-40 mM, 40-50 mM, 5-20 mM, 10-40 mM, 10-50 mM, 5-25 mM, or 25-50 mM of histidine. In some embodiments, the formulation comprises about 10-50 mM histidine. In some embodiments, the formulation comprises about 10 mM histidine.

In some embodiments, the formulation has a pH of about 5.5 to about 6.5, including, for example, about any one of 5.5, 5.6, 5.7, 5.8, 5.9, 6.0, 6.1, 6.2, 6.3, 6.4, or 6.5, including any value or range between these values. In some embodiments, the formulation has a pH of about any one of 5.5-6, 6-6.5, 5.5-5.75, 5.75-6, 6-6.25, 5.75-6.25, or 6.25-6.5. In some embodiments, the formulation has a pH of about 6.2.

In some embodiments, the formulation comprises about 0.005-0.05% of a surfactant (e.g., polysorbate), including for example, about any one of 0.005%, 0.0075%, 0.01%, 0.015%, 0.02%, 0.025%, 0.03%, 0.035%, 0.04%, 0.045%, or 0.05%, including any value or range between these values. In some embodiments, the formulation comprises about any one of 0.005-0.01%, 0.01-0.02%, 0.02-0.03%, 0.03-0.04%, 0.04-0.05%, 0.005-0.02%, 0.01-0.04%, or 0.005-0.05% of the surfactant (e.g., polysorbate).

In some embodiments, the formulation comprises about 0.005-0.05% of polysorbate 80, including for example, about any one of 0.005%, 0.0075%, 0.01%, 0.015%, 0.02%, 0.025%, 0.03%, 0.035%, 0.04%, 0.045%, or 0.05%, including any value or range between these values. In some embodiments, the formulation comprises about any one of 0.005-0.01%, 0.01-0.02%, 0.02-0.03%, 0.03-0.04%, 0.04-0.05%, 0.005-0.02%, 0.01-0.04%, or 0.005-0.05% of polysorbate 80. In some embodiments, the formulation comprises about 0.01% polysorbate 80.

In some embodiments, the formulation comprises about 1-10 mg/mL of the oligosaccharide-GAA conjugate, including, for example, about any one of 1, 2, 3, 4, 5, 6, 7, 8, 9, or 10 mg/mL of the oligosaccharide-GAA conjugate. In some embodiments, the formulation comprises about any one of 1-5, 2-8, 3-7, 4-6, 1-2.5, 2.5-5, 5-7.5, 7.5-10 or 5-10 mg/mL of the oligosaccharide-GAA conjugate. In some embodiments, the formulation comprises about 5-10 mg/mL of the oligosaccharide-GAA conjugate. In some embodiments, the formulation comprises about 5 mg/mL of the oligosaccharide-GAA conjugate.

In some embodiments, there is provided a formulation comprising: (a) any one of the oligosaccharide-GAA conjugates described herein (e.g., Formulae I-III, or avalglucosidase alfa); and (b) about 1-4% mannitol. In some embodiments, there is provided a formulation comprising: (a) any one of the oligosaccharide-GAA conjugates described herein (e.g., Formulae I-III, or avalglucosidase alfa); (b) about 1-4% mannitol; and (c) about 0.25-2% glycine. In some embodiments, there is provided a formulation comprising: (a) any one of the oligosaccharide-GAA conjugates described herein (e.g., Formulae I-III, or avalglucosidase alfa); (b) about 1-4% mannitol; (c) about 0.25-2% glycine; and (d) about 10-50 mM histidine. In some embodiments, there is provided a formulation comprising: (a) any one of the oligosaccharide-GAA conjugates described herein (e.g., Formulae I-III, or avalglucosidase alfa); (b) about 1-4% mannitol; (c) about 0.25-2% glycine; (d) about 10-50 mM histidine; and (e) about 0.005-0.05% polysorbate (e.g., polysorbate 80). In some embodiments, the formulation is a lyophilized formulation. In some embodiments, the formulation is a lyophilizable formulation. In some embodiments, there is provided a pharmaceutical composition that is reconstituted from the lyophilized formulation. In some embodiments, the formulation comprises about 5 mg/mL to about 10 mg/mL of the oligosaccharide-GAA conjugate. In some embodiments, the formulation has a pH of about 5.5 to about 6.5.

In some embodiments, there is provided a formulation comprising: (a) any one of the oligosaccharide-GAA conjugates described herein (e.g., Formulae I-III, or avalglucosidase alfa); and (b) about 2% mannitol. In some embodiments, there is provided a formulation comprising: (a) any one of the oligosaccharide-GAA conjugates described herein (e.g., Formulae I-III, or avalglucosidase alfa); (b) about 2% mannitol; and (c) about 2% glycine. In some embodiments, there is provided a formulation comprising: (a) any one of the oligosaccharide-GAA conjugates described herein (e.g., Formulae I-III, or avalglucosidase alfa); (b) about 2% mannitol; (c) about 2% glycine; and (d) about 10 mM histidine. In some embodiments, there is provided a formulation comprising: (a) any one of the oligosaccharide-GAA conjugates described herein (e.g., Formulae I-III, or avalglucosidase alfa); (b) about 2% mannitol; (c) about 2% glycine; (d) about 10 mM histidine; and (e) about 0.01% polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation. In some embodiments, the formulation comprises about 5 mg/mL of the oligosaccharide-GAA conjugate. In some embodiments, the formulation has a pH of about 6.2.

In some embodiments, there is provided a lyophilized or lyophilizable formulation comprising: (a) avalglucosidase alfa; (b) about 1-4% mannitol; (c) about 0.25-2% glycine; (d) about 10-50 mM histidine; and (e) about 0.005-0.05% polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation. In some embodiments, the formulation comprises about 5 mg/mL of avalglucosidase alfa. In some embodiments, the formulation has a pH of about 6.2.

In some embodiments, there is provided a lyophilized or lyophilizable formulation comprising: (a) avalglucosidase alfa; (b) about 2% mannitol; (c) about 2% glycine; (d) about 10 mM histidine; and (e) about 0.01% polysorbate 80. In some embodiments, the formulation is a lyophilized formulation. In some embodiments, the formulation is a lyophilizable formulation. In some embodiments, there is provided a pharmaceutical composition that is reconstituted from the lyophilized formulation. In some embodiments, the formulation comprises about 5 mg/mL of avalglucosidase alfa. In some embodiments, the formulation has a pH of about 6.2.

The term "buffer" encompasses those agents which maintain the solution pH in an acceptable range prior to lyophilization and may include succinate (sodium or potassium), histidine, phosphate (sodium or potassium), Tris(tris (hydroxymethyl)aminomethane), diethanolamine, citrate (sodium) and the like. Examples of buffers that will control the pH in this range include succinate (such as sodium succinate), gluconate, histidine, citrate and other organic acid buffers.

The term "cryoprotectants" generally includes agents, which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as mannitol; surfactants such as polysorbates; and amino acids such as glycine, arginine, and serine.

The formulations described herein may further comprise one or more pharmaceutically acceptable excipients, such as bulking agents, tonicity modifiers, anti-oxidants and preservatives The cryoprotectants described herein, such as mannitol and glycine, may serve the multiple roles, including being a bulking agent and/or a tonicity modifier. The term "bulking agents" comprise agents that provide the structure of the freeze-dried product. In addition to providing a pharmaceutically elegant cake, bulking agents may also impart useful qualities in regard to modifying the collapse temperature, providing freeze-thaw protection, and enhancing the protein stability over long-term storage. The term "tonicity modifiers" includes salts (NaCl, KCl, $MgCl_2$, $CaC_{12}$, etc.) that used as tonicity modifiers to control osmotic pressure.

In some embodiments, the formulations described herein comprise an anti-oxidant, such as methionine. In some embodiments, the formulations described herein do not comprise an anti-oxidant. In some embodiments, the formulation comprises about 1-20 mM of an anti-oxidant (e.g., methionine), including for example, about any one of 1, 2, 5, 10, 15, or 20 mM of the anti-oxidant, including any value or range between these values.

The formulations described herein are stable. A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

A "stable" lyophilized formulation is a lyophilized formulation with no significant changes observed at a refrigerated temperature (2-8° C.) for at least 12 months, preferably 2 years, and more preferably 3 years; or at room temperature (23-27° C.) for at least 3 months, preferably 6 months, and more preferably 1 year. The criteria for stability are as follows: no more than 10%, preferably 5%, 3%, 2%, 1% or less of the oligosaccharide-GAA conjugate monomer is degraded as measured by size exclusion chromatography (SEC). The rehydrated solution is colorless, or clear to slightly opalescent by visual analysis. The concentration, pH and osmolality of the formulation have no more than +/−10% change. Potency is within 70-130, preferably 80-120% of the control. No more than 10%, preferably 5%, 3%, 2%, 1% or less of clipping is observed. No more than 10%, preferably 5%, 3%, 2%, 1% or less of aggregation is formed.

The following criteria are considered in developing stable lyophilized formulations. Protein unfolding during lyophilization should be minimized. Various degradation pathways should be minimized, including degradation of the chemical linkage between the GAA and the oligosaccharide, and degradation of the GAA protein. Glass transition temperature (Tg) should be greater than the product storage temperature. Residual moisture should be low (<1% by mass). A strong and elegant cake structure should be obtained. A preferred shelf life should be at least 3 months, preferably 6 months, more preferably 1 year at room temperature (22 to 28° C.). A reconstitution time should be short, for example, less than 5 minutes, preferably less than 2 minutes, and more preferably less than 1 minute. When the lyophilized product is reconstituted, the reconstituted sample should be stable for at least 48 hours at 2-8° C.

The formulations described herein minimize the formation of aggregates and particulates in pharmaceutical compositions comprising the oligosaccharide-GAA conjugates and ensure that the oligosaccharide-GAA conjugate maintains its activity after reconstitution from the lyophilized formulation. The pharmaceutical compositions described herein may comprise a sterile, pharmaceutically acceptable lyophilized formulation prepared from an aqueous pre-lyophilized (i.e., lyophilizable) formulation.

Lyophilization is a freeze-drying process that is often used in the preparation of pharmaceutical products to preserve their biological activity. A liquid composition is prepared, and then lyophilized to form a dry cake-like product. The process generally involves drying a previously frozen sample in a vacuum to remove the ice, leaving the non-water components intact, in the form of a powdery or cake-like substance. The lyophilized product can be stored for prolonged periods of time, and at elevated temperatures, without loss of biological activity, and can be readily reconstituted into a particle-free solution by the addition of an appropriate diluent. An appropriate diluent can be any liquid which is biologically acceptable and in which the lyophilized powder is completely soluble. Water, particularly sterile, pyrogen-free water, is a preferred diluent, since it does not include salts or other compounds, which may affect the stability of the oligosaccharide-GAA conjugate. The advantage of lyophilization is that the water content is reduced to a level that greatly reduce the various molecular events, which lead to instability of the product upon long-term storage. The lyophilized product is also more readily able to withstand the physical stresses of shipping. The reconstituted product is particle free, thus it can be administered without prior filtration.

A liquid pre-lyophilized (i.e., lyophilizable) formulation can be lyophilized using appropriate drying parameters. For example, the following drying parameters can be used: a primary drying phase temperature of about −20° C. to −50° C. and pressure between about 80 mTorr to about 120 mTorr; and a secondary drying phase at ambient temperature, and pressure between about 80 mTorr to 120 mTorr.

The lyophilized formulation is rehydrated at the time of use in a diluent (e.g., sterile water or saline) to yield a particle-free pharmaceutical composition. The reconstituted pharmaceutical composition is particle-free even after prolonged storage of the lyophilized cake at ambient temperature. The reconstituted pharmaceutical composition is administered parenterally, preferably intravenously or subcutaneously, to the subject.

An important characteristic of the lyophilized formulation is the reconstitution time or the time taken to rehydrate the dry powder. To enable very fast and complete rehydration, it is important to have a cake with a highly porous structure. The cake structure is a function of a number of parameters including the concentration of the oligosaccharide-GAA conjugate, excipient type and concentration, and the process parameters of the lyophilization cycle. Generally the reconstitution time increases as the concentration increases, and thus, a short reconstitution time is an important goal in the development of high concentration lyophilized formulations of the oligosaccharide-GAA conjugate.

Further provided are use of any one of the formulations or pharmaceutical compositions described herein in the preparation of a medicament for treating Pompe disease (such as IOPD). Also provided are any one of the formulations or pharmaceutical compositions described herein for use in treating Pompe disease (such as IOPD).

IV. Kits and Articles of Manufacture

The present application further provides kits and articles of manufacture for use in any embodiment of the treatment methods described herein. The kits and articles of manufacture may comprise any one of the formulations and pharmaceutical compositions described herein. For example, a kit comprising a lyophilized formulation of avalglucosidase alfa is provided.

In some embodiments, provided herein is a kit comprising a formulation comprising any one of the oligosaccharide-GAA conjugates described herein (e.g., Formulae I-III, or avalglucosidase alfa), one or more cryoprotectants one or more buffer agents (for example, histidine), and one or more cryoprotectants comprising a sugar that is not degraded by the GAA (for example, mannitol). In some embodiments, the one or more cryoprotectants comprise mannitol and glycine. In some embodiments, the one or more cryoprotectants further comprise a surfactant (for example, polysorbate 80). In some embodiments, the kit comprises a formulation comprising any one of the oligosaccharide-GAA conjugates described herein (e.g., Formulae I-III, or avalglucosidase alfa), histidine, glycine, mannitol, and polysorbate 80. In some embodiments, the formulation comprises about 10-50 mM (e.g., about 10 mM) histidine, about 0.25-2% (e.g., about 2%) glycine, about 1-4% (e.g., about 2%) mannitol and about 0.005-0.05% (e.g., about 0.01%) polysorbate 80. In some embodiments, the formulation is a lyophilized formulation, a lyophilizable formulation, or a reconstituted liquid formulation. In some embodiments, the pH of the formulation is about 5.5 to about 6.5 (e.g., about 6.2). In some embodiments, the formulation comprises about 5 mg/mL to about 10 mg/mL of the oligosaccharide-GAA conjugate. In some embodiments, the formulation comprises avalglucosidase alfa.

In one embodiment, provided herein is an article of manufacture comprising a container comprising a formulation comprising any one of the oligosaccharide-GAA conjugates described herein (e.g., Formulae I-III, or avalglucosidase alfa), one or more cryoprotectants one or more buffer agents (for example, histidine), and one or more cryoprotectants comprising a sugar that is not degraded by the GAA (for example, mannitol). In some embodiments, the one or more cryoprotectants comprise mannitol and glycine. In some embodiments, the one or more cryoprotectants further comprise a surfactant (for example, polysorbate 80). In some embodiments, the article of manufacture comprises a container comprises a formulation comprising any one of the oligosaccharide-GAA conjugates described herein (e.g., Formulae I-III, or avalglucosidase alfa), about 10-50 mM (e.g., about 10 mM) histidine, about 0.25-2% (e.g., about 2%) glycine, about 1-4% (e.g., about 2%) mannitol and about 0.005-0.05% (e.g., about 0.01%) polysorbate 80. In some embodiments, the formulation is a lyophilized formulation, a lyophilizable formulation or a reconstituted liquid formulation. In some embodiments, the pH of the formulation is about 5.5 to about 6.5 (e.g., about 6.2). In some embodiments, the formulation comprises about 5 mg/mL to about 10 mg/mL of the oligosaccharide-GAA conjugate. In some embodiments, the formulation comprises avalglucosidase alfa. In some embodiments, the container is a vial. In some embodiments, the container is a 20 cc vial.

The kits and articles of manufacture of the present application are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

A kit further comprises instructions for using the oligosaccharide-GAA conjugate in treating Pompe disease (such as IOPD). In some embodiments, the kit further comprises an instructional manual, such as a manual describing a protocol of any embodiment of the treatment methods described herein. The instructions may include information on dosage, dosing schedule, and routes of administration of oligosaccharide-GAA conjugate (e.g., avalglucosidase alfa). In some embodiments, the kit further comprises instructions for selecting an individual for the treatment method. In some embodiments, the kit further comprises instructions for monitoring an individual after receiving the treatment.

The containers may be unit doses, bulk packages (e.g., multi-dose packages) or sub-unit doses. For example, kits may be provided that contain sufficient oligosaccharide-GAA conjugate (e.g., avalglucosidase alfa) as disclosed herein to provide effective treatment of an individual for an extended period, such as any of 3 weeks, 6 weeks, 9 weeks, 3 months, 4 months, 5 months, 6 months, 8 months, 9 months, 1 year or more.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

EXAMPLES

The examples below are intended to be purely exemplary of the invention and should therefore not be considered to limit the invention in any way. The following examples and detailed description are offered by way of illustration and not by way of limitation.

Example 1. Avalglucosidase Alfa in Infantile-Onset Pompe Disease Clinical Trial The following example describes an open-label ascending dose cohort study assessing the safety, pharmacokinetics, and preliminary efficacy of avalglucosidase alfa in patients with infantile-onset Pompe disease treated with alglucosidase alfa who demonstrate clinical decline or sub-optimal clinical response.

A. Study Design
Objectives

The primary objective of the study was to evaluate the safety profile of avalglucosidase alfa in patients with infantile-onset Pompe disease (IOPD) previously treated with alglucosidase alfa. The secondary objectives were to characterize the pharmacokinetic profile of avalglucosidase alfa and to evaluate the preliminary efficacy of avalglucosidase alfa in comparison to alglucosidase alfa.

Methodology

A multi-stage phase 2 open-label, multicenter, multinational, ascending dose cohort study was performed comprising repeated intravenous infusion study of avalglucosidase alfa in pediatric patients with IOPD who have been previously treated with alglucosidase alfa and demonstrated clinical decline (Stage 1) or sub-optimal clinical response (Stage 2) in specified respiratory function, motor skills, cardiac parameters, and/or new onset of ptosis (including eyelid position measurements, such as interpalpebral fissure distance (IPFD), margin reflex distance-1 (MRD-1), and margin pupil distance (MPD)). A schematic summary of the study design is provided in FIG. 1.

Patients in Cohorts 1 and 2 had documented evidence of clinical decline in at least one of the following parameters related to Pompe disease: respiratory function, motor skills, and/or cardiac parameters. Patients in Cohort 3 had documented evidence of suboptimal clinical response while receiving alglucosidase alfa in at least one of the following parameters related to Pompe disease: respiratory function, motor skills, and/or new onset of ptosis (confirmed by at least 2 sequential assessments).

In Stage 1, patients in Cohorts 1 received 20 mg/kg of avalglucosidase alfa throughout the study and patients in Cohort 2 received 40 mg/kg avalglucosidase alfa throughout the study (FIG. 1). In Stage 2, patients enrolled in Cohort 3 were randomized to receive either the maximum tolerated dose of avalglucosidase alfa from Cohorts 1 and 2 (i.e., 40 mg/kg) or alglucosidase alfa (at stable dose for at least 6 months prior to enrolling in the study, labelling or higher than labelling dose) for the first 6 months of the study before switching to 40 mg/kg avalglucosidase alfa. All patients received avalglucosidase alfa for the remainder of the study.

Diagnosis and Criteria for Inclusion and Exclusion

Included patients had a documented GAA deficiency, were aged <18 years old, had cardiac involvement at the time of Pompe disease diagnosis, had been receiving a stable dose of alglucosidase alfa regularly for a minimum of 6 months immediately prior to study entry, and had documented evidence of clinical decline (Stage 1 patients) or suboptimal clinical response (Stage 2 patients).

Inclusion criteria for the study were as follows:
- The patient had confirmed acid alpha-glucosidase (GAA) enzyme deficiency from any tissue source (e.g., blood, skin or muscle tissue).
- The patient who had reached legal age of majority as defined by local regulation, or the patient's legal guardian(s) provided signed informed consent prior to performing any study-related procedures. If the patient was legally minor per local regulations, assent was obtained from patients, if applicable.
- The patient (and patient's legal guardian if patient is legally minor as defined by local regulation) must have had the ability to comply with the clinical protocol.
- The patient was <18 years old.
- The patient, if female and of childbearing potential, must have had a negative serum pregnancy test (beta-human chorionic gonadotropin) and must not have been breastfeeding at screening/baseline.

The patient had cardiomyopathy at the time of diagnosis in the first year of life: i.e., left ventricular mass index (LVMI) equivalent to mean age specific LVMI plus 2 standard deviations.

The patient had been receiving a stable dose of alglucosidase alfa regularly for a minimum of 6 months immediately prior to study entry.

For participants in Stage 1: The patient had documented evidence of clinical decline in at least one of the following parameters related to Pompe disease and not related to intercurrent illness: respiratory function, motor skills, and/or cardiac parameters.

For participants in Stage 2: The patient had documented evidence of suboptimal clinical response in at least one of the following parameters related to Pompe disease and not related to intercurrent illness: respiratory function, motor skills, and/or new onset of ptosis.

Excluded patients had a high antibody titer (i.e., anti-alglucosidase alfa antibody titer ≥1:25,600) at 2 consecutive time points >1 month apart); clinically significant organic disease (except for Pompe disease), which may have resulted in abnormal laboratory parameters or potentially decreased survival; or high risk for severe allergic reaction to avalglucosidase alfa (i.e., previous moderate/severe anaphylactic reaction, IgE antibodies, or history of high IgG antibodies to alglucosidase alfa).

Exclusion criteria for the study were as follows:
The patient had high antibody titer to alglucosidase alfa.
The patient had a high risk for a severe allergic reaction to avalglucosidase alfa.
The patient required any prohibited concomitant medications (e.g., immune modulatory treatment) for the duration of the study.
The patient had previously participated in any ACT14132 study cohort.
Female patient of childbearing potential not protected by highly effective contraceptive method of birth control and/or who is unwilling or unable to be tested for pregnancy Primary and Main Secondary Key Endpoints Primary safety endpoints included (1) adverse events/treatment-emergent adverse events (TEAEs), including infusion-associated reactions (IARs) (Table 5); (2) clinical laboratory analyses including standard biochemistry, hematology and urinalysis as a descriptive summary; and (3) immunogenicity assessments as a descriptive summary.

Secondary pharmacokinetic endpoints included plasma parameters including $C_{max}$, $t_{max}$, area under the curve ($AUC_{0-last}$), terminal half-life ($t_{1/2z}$), clearance (CL), and volume of distribution (Vd).

Figure 2A:
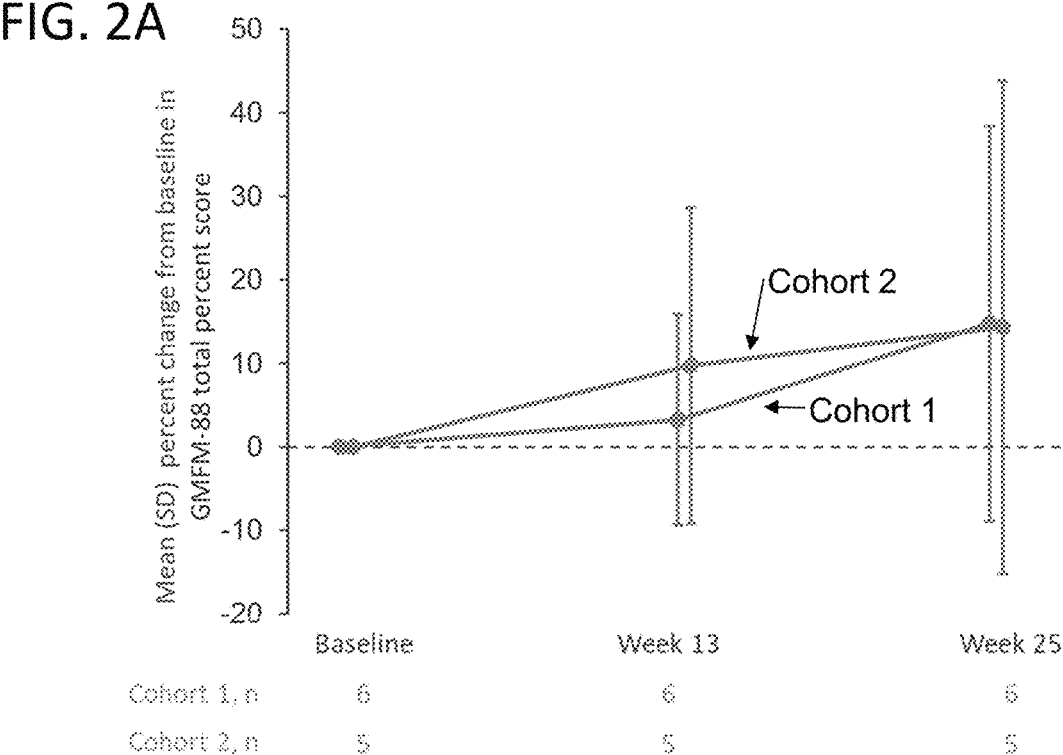
FIGS. 2A-2B show changes in Gross Motor Function Measure-88 (GMFM-88) total percent scores relative to baseline.
Figure 2B:
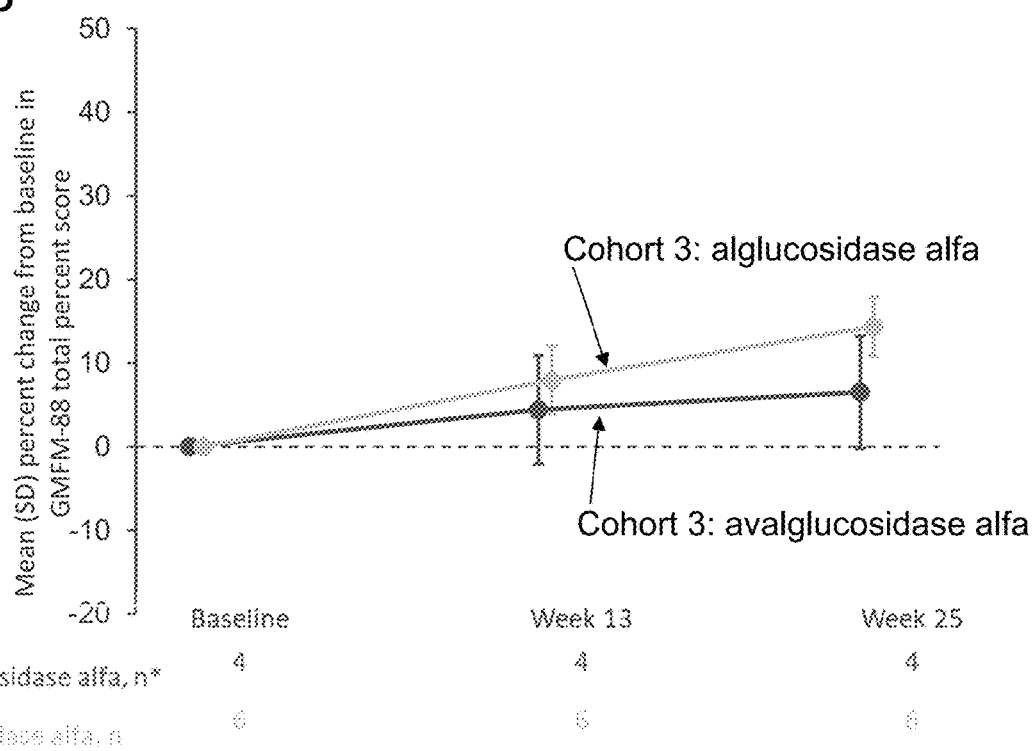
Figure 3:
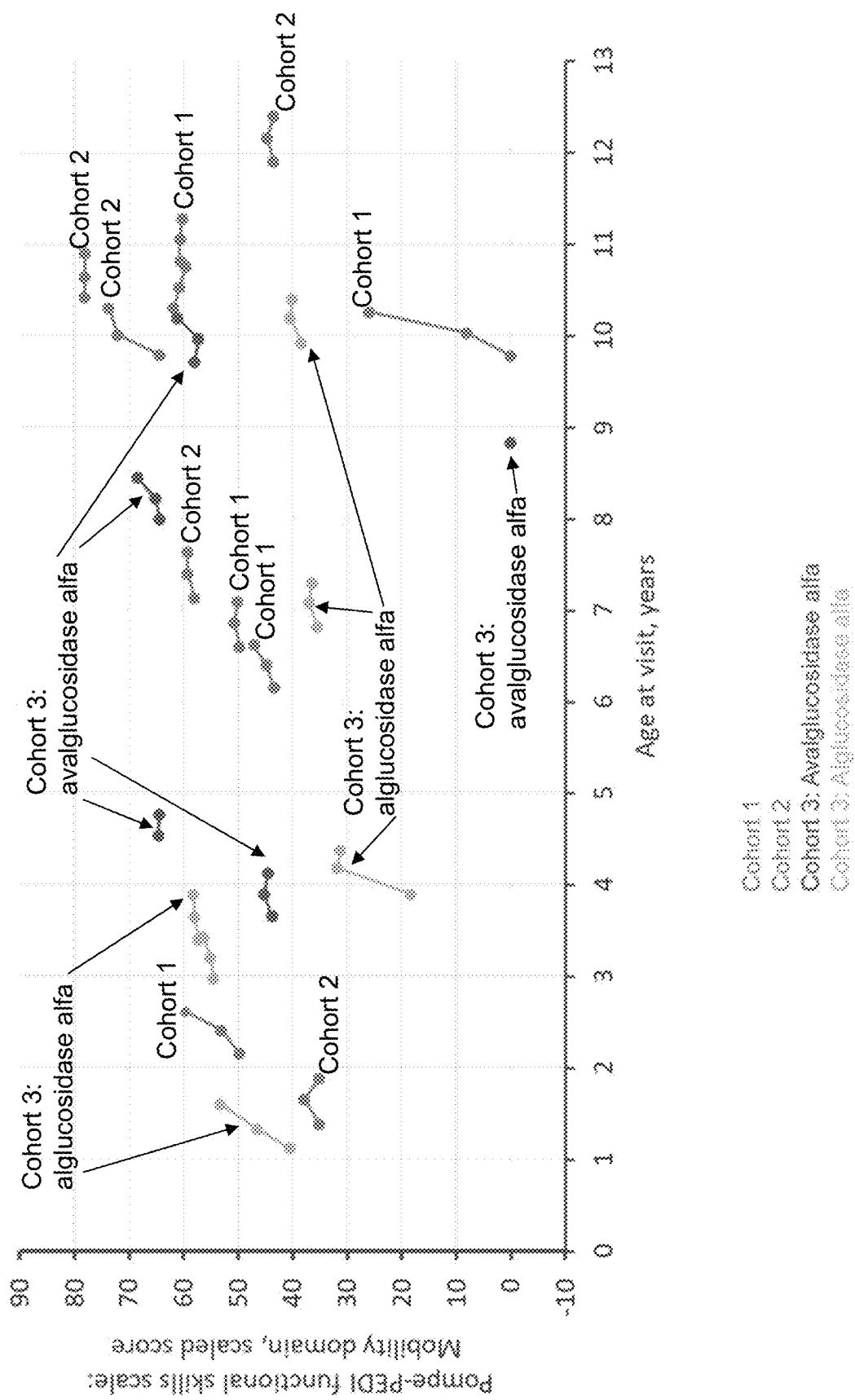
FIG. 3 show Pompe Pediatric Evaluation of Disability Inventory (Pompe-PEDI) Functional Skills Scale: Mobility Domain scaled scores over time, by patient age. The patient age at the time of visit is shown on the x-axis, and the scaled score is shown on the y-axis. Cohort 1 individuals are shown in blue, Cohort 2 individuals are shown in orange, Cohort 3 individuals receiving alglucosidase alfa to be followed by avalglucosidase alfa after week 25 are shown in pink, and Cohort 3 individuals receiving alglucosidase alfa are shown in green.
Figure 4A:
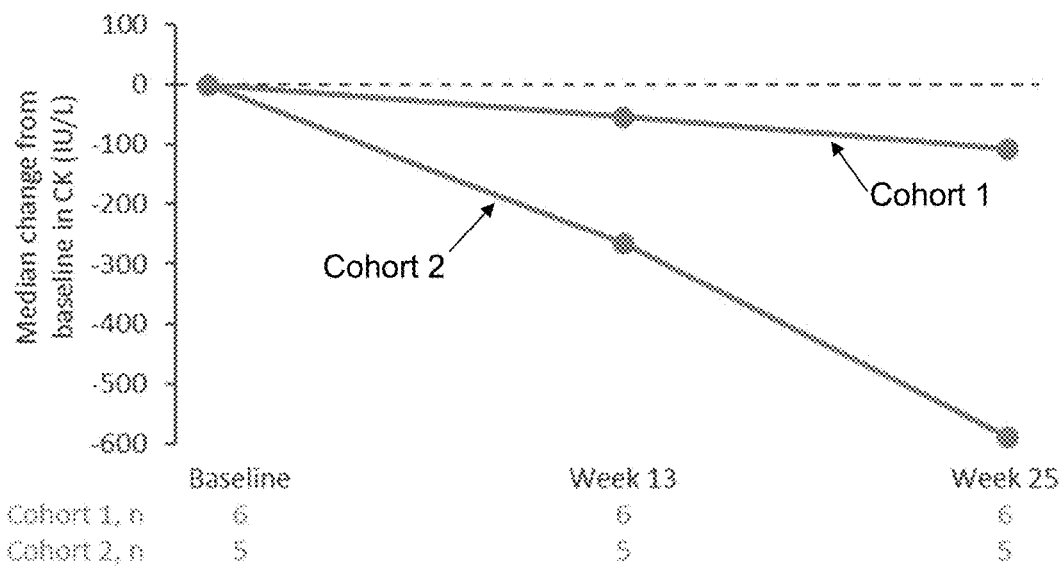
FIGS. 4A-4B show changes in creatine kinase (CK) levels relative to baseline over time.
Figure 4B:
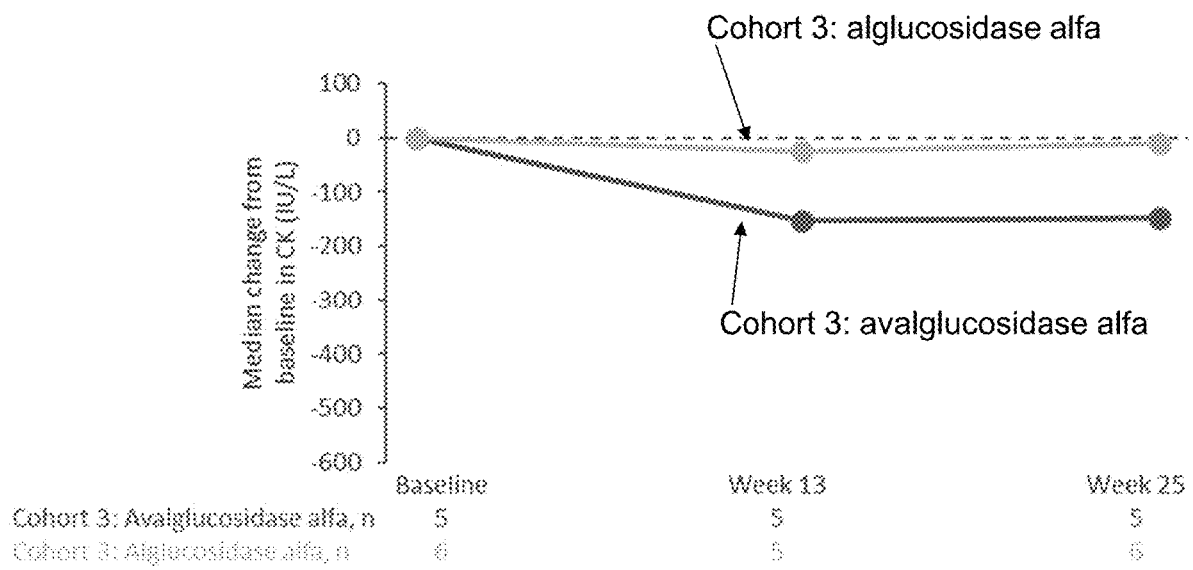

Secondary efficacy endpoints included change in the following parameters at 6 months: Gross Motor Function Measure-88 (GMFM-88, see FIGS. 2A-2B) and Gross Motor Function Classification System-Expanded and Revised (GMFCS-E&R); Pompe Pediatric Evaluation of Disability Inventory (Pompe-PEDI) Functional Skills Scale: Mobility Domain (FIG. 3); Quick Motor Function Test (QMFT); Echocardiography (ECHO) endpoints (Table 6): left ventricular mass index (LVMI) and left ventricular mass (LVM) Z-score; and creatine kinase levels (FIGS. 4A-4B).

Figure 5A:
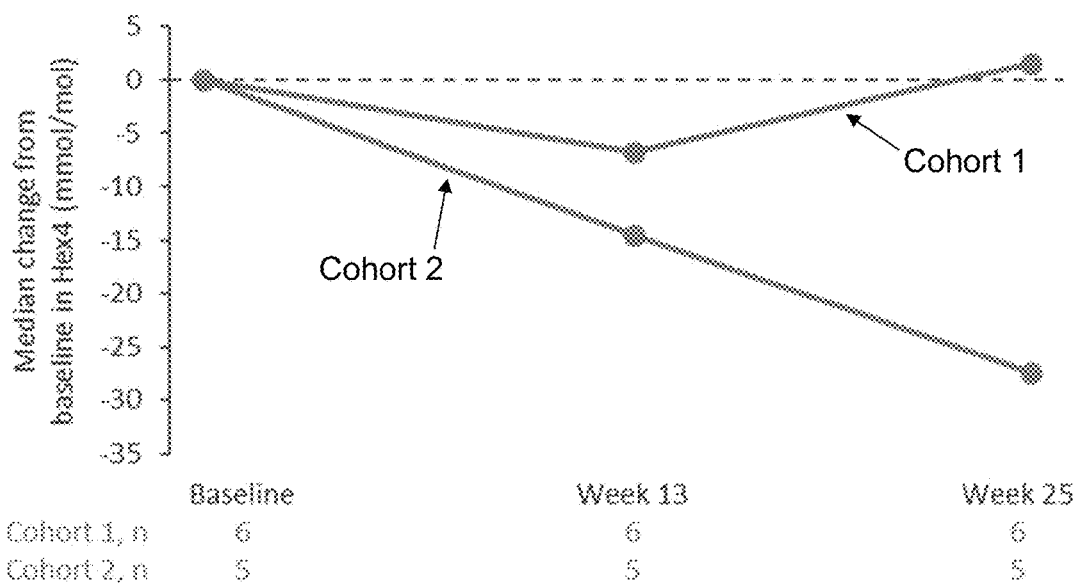
FIGS. 5A-5B show changes in HEX4 levels relative to baseline over time.
Figure 5B:
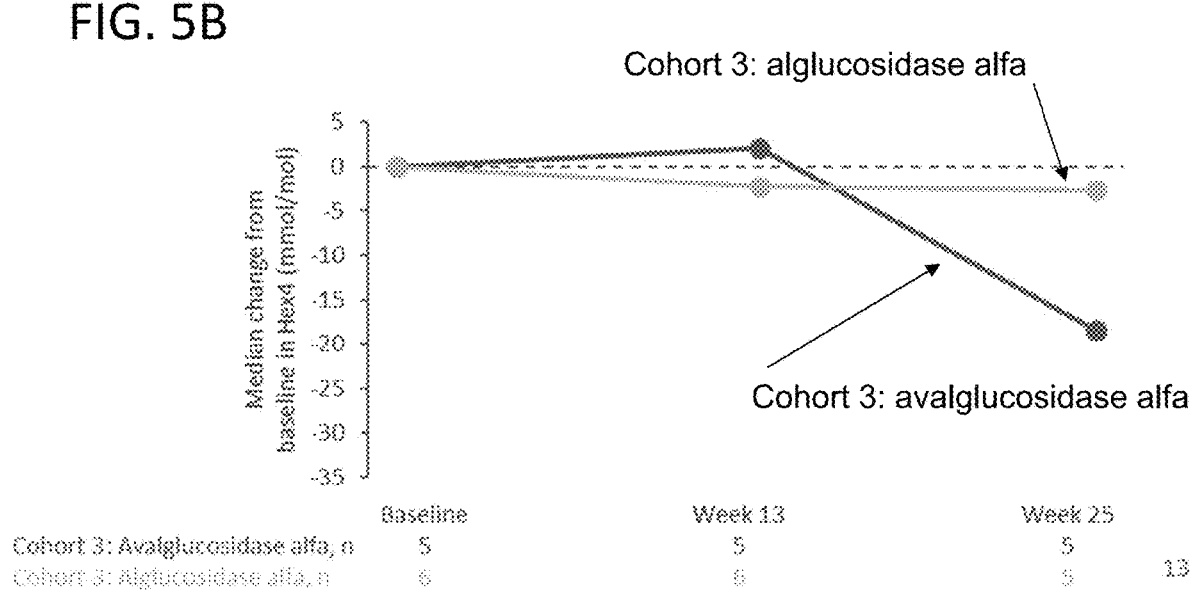

Other secondary endpoints included a 6 Minute Walk test (6MWT) measuring the distance walked in patients who were able to ambulate at least 40 meters (approximately 130 feet) without stopping and without an assistive device; ventilator use and urinary HEX-4 levels (FIGS. 5A-5B).

Another secondary endpoint was eyelid position measurements. The assessments were made at screening/Baseline, Day 1, and every 2 weeks from Week 3 through to Week 25 (inclusive). The diagnosis of ptosis as defined as an inclusion criteria for suboptimal improvement was based on the treating Principal Investigator's assessment; in addition, a central reader checked the evaluated presence of ptosis based on photographs taken at baseline and at each visit, including Week 25. Images of participants' eyes were taken while they were wearing a novel measuring device, consisting of a pair of empty eyeglass frames with rulers attached as a standardized measurement tool (FIG. 6A). The following eyelid position measurements were performed by an independent central reader masked to the treatment group and dose: (1) Interpalpebral Fissure Distance (IPFD): vertical distance between upper and lower eyelid margins (FIG. 6B); (2) Margin Reflex Distance-1 (MRD-1): distance between corneal light reflex and upper eyelid margin (FIG. 6C); (3) Margin Pupil Distance (MPD): distance between center of the pupil and upper eyelid margin (FIG. 6D).

Statistical Methods

Descriptive summaries of safety results were provided based on the safety population which was defined as all patients who received at least one infusion (partial or total) in the study. The data on adverse event, laboratory safety variables and immunogenicity were summarized.

Descriptive summaries and/or plots of efficacy endpoints, pharmacokinetics and pharmacodynamics endpoints were provided for all cohorts.

Avalglucosidase Alfa Formulation and Administration

Avalglucosidase alfa was formulated in vials each containing approximately 105 mg of avalglucosidase alfa in 10 mM histidine, 2% glycine, 2% mannitol, 0.01% polysorbate 80, pH 6.2. It was reconstituted with sterile water to a final concentration of about 10 mg/mL for injection prior to administration. The reconstituted solution was diluted in 5% Dextrose in Water to a final concentration of 0.5 mg/mL to 4 mg/mL.

Infusion should be administered incrementally as determined by patient response and comfort over approximately 6 hours for patients with IOPD. For patients with IOPD, it is recommended that the infusion begins at an initial rate of 1 mg/kg/hour and is gradually increased by 2 mg/kg/hour every 30 minutes if there are no signs of infusion-associated reactions (IARs), until a maximum rate of 7 mg/kg/hour (for patients with LOPD) and 10 mg/kg/hour (for patients with IOPD) is reached. Vital signs should be obtained at each step, before increasing the infusion rate. Patients may be pretreated with antihistamines, antipyretics and/or corticosteroids to prevent or reduce allergic reactions.

B. Results

Population Characteristics

Six patients were enrolled in Cohort 1, 5 were enrolled in Cohort 2, and 11 were enrolled in Cohort 3 (Table 1). Patients were enrolled at two sites in France, two sites in Japan, two sites in UK, 3 sites in the US and one site in Taiwan, China. Of the Cohort 3 patients, six were randomized to alglucosidase alfa and five to avalglucosidase alfa. Patients were aged between 1 and 12 years.

Patients' demographics and characteristics at baseline were comparable across the three cohorts and treatment arms except for age: cohort 3 patients randomized to alglucosidase alfa were of a younger age (Table 1). Table 2 provides a summary of patient medical history from time of diagnosis, prior to enrollment in study. Baseline functional levels were heterogeneous across all patients, with less severe motor dysfunction in cohort 3 (Table 3). There were two cross-reactive immunologic material (CRIM)-negative patients and 20 CRIM-positive patients (Table 3).

Cohort 3 alglucosidase alfa treatment-arm participants were younger at Baseline than in the other cohorts and received dose regimens ranging from 20 mg/kg qow up to 40 mg/kg weekly. Cohort 1 participants were predominantly male. Overall, participants' growth parameters were essentially within normal ranges.

TABLE 1

Summary of patient demographics at baseline

| Parameter | Cohort 1 (N = 6) | Cohort 2 (N = 5) | Cohort 3 Avalglucosidase alfa (N = 5) | Cohort 3 Alglucosidase alfa (N = 6) |
|---|---|---|---|---|
| Country, n (%) | | | | |
| France | 2 (33) | 1 (20) | 0 | 1 (17) |
| Japan | 1 (17) | 1 (20) | 0 | 0 |
| Taiwan | 2 (33) | 2 (40) | 1 (20) | 0 |
| United Kingdom | 0 | 0 | 1 (20) | 1 (17) |
| United States | 1 (17) | 1 (20) | 3 (60) | 4 (67) |
| Age at study entry, mean (standard deviation), years | 7.6 (3.4) | 8.1 (4.1) | 6.9 (2.7) | 4.7 (3.2) |
| Age at study entry, median (min, max), years | 8.2 (2, 11) | 9.8 (1, 12) | 8.0 (4, 10) | 3.6 (1, 10) |
| Sex, n (%) | | | | |
| Male | 5 (83) | 3 (60) | 2 (40) | 2 (33) |
| Female | 1 (17) | 2 (40) | 3 (60) | 4 (67) |
| Race, n (%) | | | | |
| White | 3 (50) | 2 (40) | 3 (60) | 4 (67) |
| Black or African American | 0 | 0 | 0 | 2 (33) |
| Asian | 3 (50) | 3 (60) | 2 (40) | 0 |
| Height, Z-score, mean (standard deviation) | −0.2 (0.7) | 0.0 (1.4) | −0.8 (0.8) | −0.1 (1.2) |
| Height, Z-score, median (min, max) | −0.3 (−1, 1) | −0.3 (−1, 2) | −1.2 (−2, 0) | 0.3 (−2, 1) |
| Weight, Z-score, mean (standard deviation) | −0.1 (1.4) | −0.2 (2.1) | 0.4 (0.9) | 0.1 (0.9) |
| Weight, Z-score, median (min, max) | 0.0 (−2, 2) | −0.1 (−3, 3) | 0.5 (−1, 1) | 0.4 (−1, 1) |
| Body Mass Index, Z-score, mean (standard deviation) | −0.16 (1.91) | −0.06 (2.57) | 1.07 (1.25) | 0.48 (0.36) |
| Body Mass Index, Z-score, median (min, max) | 0.41 (−2.7, 1.6) | 0.64 (−3.7, 2.2) | 0.98 (−0.7, 2.4) | 0.50 (0.1, 1.0) |
| Head circumference, mean (standard deviation) | 53.4 (3.4) | 51.7 (2.7) | 53.2 (1.5) | 50.6 (2.5) |
| Head circumference, median (min, max), cm* | 54.0 (48, 58) | 52.0 (49, 56) | 53.2 (52, 56) | 50.9 (46, 54) |

*Head circumference Z-scores available for patients aged between 0 and 35 months (inclusive) only (n = 4) WHO head circumference Z-score tables.

TABLE 2

Summary of patient medical history from time of diagnosis/prior to enrollment in study

| Parameter | Cohort 1 (N = 6) | Cohort 2 (N = 5) | Cohort 3 Avalglucosidase alfa (N = 5) | Cohort 3 Alglucosidase alfa (N = 6) |
|---|---|---|---|---|
| Congestive heart failure, yes, n (%) | 0 | 1 (20.0) | 0 | 0 |
| Cardiac involvement, yes, n (%) | 6 (100) | 5 (100) | 5 (100) | 6 (100) |
| Arrhythmia | 0 | 0 | 1 (20) | 0 |
| Cardiomegaly | 6 (100) | 5 (100) | 2 (40) | 4 (67) |
| Other | 0 | 0 | 2 (40) | 2 (33) |
| Enlarged tongue, yes, n (%) | 4 (67) | 3 (60) | 4 (80) | 2 (33) |
| Hearing loss, yes, n (%) | 6 (100) | 3 (60) | 5 (100) | 4 (67) |
| Hepatomegaly, yes, n (%) | 1 (17) | 2 (40) | 1 (20) | 2 (33) |
| Gastroesophageal reflux, yes, n (%) | 1 (17) | 1 (20) | 0 | 4 (67) |
| Tracheostomy, yes, n (%) | 1 (17) | 0 | 0 | 1 (17) |
| Pneumonia*, yes, n (%) | 4 (67) | 2 (40) | 3 (60) | 3 (50) |
| Sleep disturbances, yes, n (%) | 2 (33) | 0 | 3 (60) | 0 |
| Sleep apnea, yes, n (%) | 2 (33) | 2 (40) | 2 (40) | 2 (33) |
| Muscle weakness in upper extremities, yes, n (%) | 5 (83) | 4 (80) | 3 (60) | 5 (83) |

TABLE 2-continued

Summary of patient medical history from time of diagnosis/prior to enrollment in study

|  |  |  | Cohort 3 | |
| --- | --- | --- | --- | --- |
| Parameter | Cohort 1 (N = 6) | Cohort 2 (N = 5) | Avalglucosidase alfa (N = 5) | Alglucosidase alfa (N = 6) |
| Muscle weakness in lower extremities, yes, n (%) | 6 (100) | 4 (80) | 5 (100) | 6 (100) |
| Scoliosis, yes, n (%) | 3 (50) | 2 (40) | 2 (40) | 0 |
| Joint contractures, yes, n (%) | 3 (50) | 0 | 2 (40) | 2 (33) |
| Ambulatory device use, yes, n (%) | 4 (67) | 1 (20) | 3 (60) | 4 (67) |

*Of all patients with pneumonia in their history, all but one patient had <5 episodes during the year prior to enrollment; one patient in the Cohort 3 alglucosidase alfa arm had between 5 and 10 episodes in the year prior to enrollment.

TABLE 3

Summary of Pompe disease history, CRIM, and functional status at baseline

|  |  |  | Cohort 3 | |
| --- | --- | --- | --- | --- |
| Parameter | Cohort 1 (N = 6) | Cohort 2 (N = 5) | Avalglucosidase alfa (N = 5) | Alglucosidase alfa (N = 6) |
| Age at first symptoms, median (min, max), months | 0.34 (0.0, 4.4) | 4.40 (0.1, 6.5) | 0.00 (0.0, 0.9) | 1.79 (0.0, 3.7) |
| Age at diagnosis, median (min, max), months | 1.10 (0.3, 5.5) | 4.47 (0.3, 8.7) | 1.84 (0.0, 3.5) | 3.45 (0.3, 15.9) |
| Age at first treatment with alglucosidase alfa, median (min, max), months | 2.41 (0.4, 5.7) | 4.63 (0.5, 10.4) | 1.94 (0.2, 5.7) | 4.44 (0.3, 19.4) |
| Family history of Pompe disease, n (%) | 1 (17) | 1 (20) | 1 (20) | 1 (17) |
| Historical CRIM negative status, n (%)* | 0 | 1 (20) | 0 | 1 (17) |
| GMFCS-E&R |  |  |  |  |
| Level I (walks without limitations) | 1 | 1 | 2 | 3 |
| Level II (walks with limitations) | 1 | 2 | 1 | 0 |
| Level III (walks using a hand-held mobility device) | 1 | 0 | 1 | 1 |
| Level IV (self-mobility with limitations; may use powered mobility) | 2 | 2 | 0 | 1 |
| Level V (transported in a manual wheelchair) | 1 | 0 | 1 | 1 |

*2 CRIM (historical) negative patients enrolled (one patient in Cohort 2 and one patient in Cohort 3 alglucosidase alfa [pre-treated with immune tolerance induction at time of diagnosis])

No patient discontinued in the primary analysis period (25-week treatment period) or up to the data cut-off date of Sep. 30, 2019, after the last visit of the last patient (LPLV) in the primary analysis period. All patients have data available for at least 6 months.

Study Drug Exposure During Primary Analysis Period

There were no missed infusions or decreases in dose, and all 22 patients who were enrolled completed the primary analysis period (up to Week 25; Table 4). Overall treatment compliance was good; no participants missed infusions or had their dose decreased.

In the Cohort 3 alglucosidase alfa treatment arm, each patient had their own regimen based on prior stable dose, ranging from 20 mg/kg every 2 weeks up to 40 mg/kg weekly. Two patients in Cohort 1 increased dose following the primary analysis period according to protocol.

TABLE 4

Study drug exposure during primary analysis period

|  |  |  | Cohort 3 | |
| --- | --- | --- | --- | --- |
| Parameter | Cohort 1 (N = 6) | Cohort 2 (N = 5) | Avalglucosidase alfa (N = 5) | Alglucosidase alfa (N = 6) |
| Cumulative exposure to treatment, patient-years | 3.0 | 2.5 | 2.5 | 3.0 |
| Duration of study drug exposure, median (min, max), weeks | 26.1 (26, 26) | 26.1 (26, 27) | 26.0 (26, 26) | 26.0 (26, 27) |
| Total number of infusions, n | 78 | 65 | 65 | 115 |
| Number of infusions received per patient, median (min, max), n | 13 (13, 13) | 13 (13, 13) | 13 (13, 13) | 19 (13, 26) |

Safety Results

There were similar incidence of treatment-emergent adverse events (TEAEs) across all cohorts and between the two treatment arms of Cohort 3 (Table 5). Safety was in line with known safety profile for both products and the underlying disease at both dose levels (20 and 40 mg/kg qow) tested in severely affected, previously treated IOPD patients. The most common TEAEs were vomiting and pyrexia (6 patients each), upper respiratory tract infections (5 patients), cough and rash (4 patients each).

TABLE 5

Summary of safety results

|  |  |  | Cohort 3 | |
| --- | --- | --- | --- | --- |
| Parameter | Cohort 1 (N = 6) | Cohort 2 (N = 5) | Avalglucosidase alfa (N = 5) | Alglucosidase alfa (N = 6) |
| TEAEs, n (%) | 5 (83) | 5 (100) | 5 (100) | 5 (83) |
| TEAEs potentially related to treatment, n (%) | 0 | 2 (40) | 1 (20) | 1 (17) |
| Serious TEAEs, n (%) | 1 (17) | 3 (60) | 0 | 2 (33) |
| Infusion-associated reactions, n (%) | 0 | 2 (40) | 1 (20) | 1 (17) |

There were no treatment-related serious adverse events. There were no deaths or withdrawals due to adverse events in any cohort.

Four patients experienced at least one infusion associated reaction (IAR) in the primary analysis period and four patients experienced at least one IAR in the extension treatment period (ETP) (Table 5).

There were no lab or echocardiographic potentially clinically significant abnormality-related adverse events.

6 patients developed anti-drug antibodies (ADA) against avalglucosidase alfa with median peak titers of 6400, including 1 patient with boosted ADA—i.e., a pre-existing ADA that was boosted at least 2 titer steps from baseline (i.e., 4-fold increase in titers) following administration of the study drug (any time after the first drug administration). All but one patient decreased ADA over time; this patient had a peak titer of 6400 at the last available time point.

Of note, there were few CRIM-negative patients. Alglucosidase alfa treatment experienced patients were included, and patients with previous high antibody titer (anti-alglucosidase alfa antibody titer ≥1:25600) were excluded.

Efficacy Results

A majority of patients (14/16 patients treated with avalglucosidase alfa, 6/6 patients treated with alglucosidase alfa) experienced stabilization or improvement of qualifying symptoms (i.e. entry criteria of clinical decline/suboptimal response). Two worsening patients increased avalglucosidase alfa dose from 20 to 40 mg/kg per protocol, after the primary analysis period.

There were positive trends (stabilization or improvement) for motor scales GMFM-88 (FIGS. 2A-2B), Pompe-PEDI (FIG. 3) and echocardiographic assessment (e.g., echocardiographic left ventricular mass (LVM) Z-score) (Table 6) with avalglucosidase alfa treatment. Individual patients demonstrated improvement or stabilization on the Pompe-PEDI functional skills scale across all cohorts (FIG. 3). There was no decline from baseline observed in ECHO-LVM Z-scores during the primary analysis period, and the sole patient with an abnormal LVM Z-score at baseline improved to normal range at Week 25 (a CRIM negative Cohort 2 patient) (Table 6).

TABLE 6

Echocardiographic (ECHO)-LVM Z-score M-MODE* outcome

|  | Cohort 1 (N = 6) | | Cohort 2 (N = 5) | | Cohort 3 | | | |
|---|---|---|---|---|---|---|---|---|
|  |  |  |  |  | Avalglucosidase alfa (N = 5) | | Alglucosidase alfa (N = 6) | |
|  | Observed | Change from baseline | Observed | Change from baseline | Observed | Change from baseline | Observed | Change from baseline |
| Baseline |  |  |  |  |  |  |  |  |
| Number | 6 | NA | 3 | NA | 5 | NA | 4 | NA |
| Median | −1.30 |  | −0.60 |  | −0.70 |  | 0.0 |  |
| (min, max) | (−2.0, 0.9) |  | (−1.8, 2.8) |  | (−1.8, −0.1) |  | (−1.8, 0.1) |  |
| Week 25 |  |  |  |  |  |  |  |  |
| Number | 5 | 5 | 4 | 2 | 5 | 5 | 4 | 3 |
| Median | −1.00 | 0.20 | −0.65 | −0.60 | −1.50 | −0.70 | 0.50 | 0.70 |
| (min, max) | (−5.2, −0.1) | (−3.2, 1.9) | (−4.6, 1.7) | (−1.1, −0.1) | (−2.5, 0.0) | (−1.3, 0.3) | (−1.4, 1.0) | (−1.4, 2.1) |

At group level there was no clear difference observed in Cohort 3 at week 25 between avalglucosidase alfa (40 mg/kg every other week) and alglucosidase alfa (at prior stable dose; range 20-40 mg/kg every other week/every week), except for the imbalance between treatment arms regarding the age of patients (i.e. there were younger patients in alglucosidase alfa arm).

Pharmacodynamics Results

There was high inter-individual variability in creatine kinase (FIGS. 4A-4B) and urinary HEX4 (FIGS. 5A-5B) parameters at all dose levels with a trend to more pronounced decrease in avalglucosidase alfa 40 mg/kg groups. Levels of the pharmacodynamic disease biomarkers for muscle damage (creatine kinase [CK]) and glycogen burden (hexose tetrasaccharide [Hex4]) also decreased with avalglucosidase alfa compared to stability with alglucosidase alfa.

Ptosis

Results of eyelid position measurements are shown in Table 7 below. At baseline, 7 of the 22 participants who were enrolled in Mini-COMET had a clinical diagnosis of ptosis, including 3 bilateral and 4 unilateral. At Week 25, 7 participants had ptosis, including 3 bilateral and 4 unilateral. In Cohort 1 (avalglucosidase alfa 20 mg/kg qow), 1 participant had left eye ptosis which resolved, and 2 additional participants developed bilateral ptosis by Week 25. In Cohort 2 (avalglucosidase alfa 40 mg/kg qow), 1 participant had right eye ptosis at Baseline and no participants had ptosis of either eye by Week 25. In Cohort 3 (avalglucosidase alfa 40 mg/kg qow), 1 additional participant developed right eye ptosis by Week 25, while 1 participant with bilateral ptosis at Baseline had none by Week 25. In Cohort 3 (alglucosidase alfa 20 mg/kg qow to 40 mg/kg weekly), 2 participants had right eye ptosis at Baseline, which was still present in 1 participant and resolved in 1 participant by Week 25, while 1 participant had left eye ptosis at Baseline which was still present at Week 25.

TABLE 7

Clinical assessment of the presence of ptosis in participants
(data are number of participants)

| | | Right eye ptosis | | Left eye ptosis | |
|---|---|---|---|---|---|
| | | Baseline absent (n = 4) | Baseline present (n = 2) | Baseline absent (n = 4) | Baseline present (n = 2) |
| Cohort 1: Avalglucosidase alfa 20 mg/kg qow (N = 6) | Week 25 Absent | 2 | 0 | 2 | 1 |
| | Week 25 Present | 2 (ptosis developed) | 2 | 2 (ptosis developed) | 1 (ptosis resolved) |
| | | Baseline absent (n = 4) | Baseline present (n = 1) | Baseline absent (n = 5) | Baseline present (n = 0) |
| Cohort 2: Avalglucosidase alfa 40 mg/kg qow (N = 5) | Week 25 Absent | 4 | 1 | 5 | 0 |
| | Week 25 Present | 0 | 0 (ptosis resolved) | 0 | 0 |
| | | Baseline absent (n = 4) | Baseline present (n = 1) | Baseline absent (n = 4) | Baseline present (n = 1) |
| Cohort 3: Avalglucosidase alfa 40 mg/kg qow (N = 5) | Week 25 Absent | 3 | 1 | 4 | 1 |
| | Week 25 Present | 1 (ptosis developed) | 0 (ptosis resolved) | 0 | 0 (ptosis resolved) |
| | | Baseline absent (n = 4) | Baseline present (n = 2) | Baseline absent (n = 5) | Baseline present (n = 1) |
| Cohort 3: Alglucosidase alfa 20 mg/kg to 40 mg/kg weekly (N = 6*) | Week 25 Absent | 4 | 1 | 5 | 1 |
| | Week 25 Present | 0 | 1 (ptosis resolved) | 0 | 0 |

FIGS. 7A-7F compare results of the various eyelid position measurements among the different Cohorts. There was a trend from Baseline to Week 25 for improvement of the eyelid position measurements in the 40 mg/kg qow avalglucosidase alfa groups (Cohort 2 and Cohort 3 avalglucosidase alfa arm). In contrast, the 20 mg/kg qow avalglucosidase alfa group (Cohort 1) and the alglucosidase alfa group (Cohort 3 alglucosidase alfa arm) showed stabilization or worsening in these measurements. Differences between the treatment groups were more pronounced for the Interpalpebral Fissure Distance (both eyes, with and without flash) than for the Margin Reflex Distance-1 (both eyes) or the Margin Pupil Distance (both eyes). Of note, non-flash images, particularly those measuring the Interpalpebral Fissure Distance and Margin Pupil Distance, may have allowed for more accurate measurements, due to the absence of eye squinting due to flash photography.

Individual Participant Responses

Individual participant responses in the Mini-COMET study have been analyzed by plotting Baseline and Week 25 data in spaghetti plots.

Figure 8A:
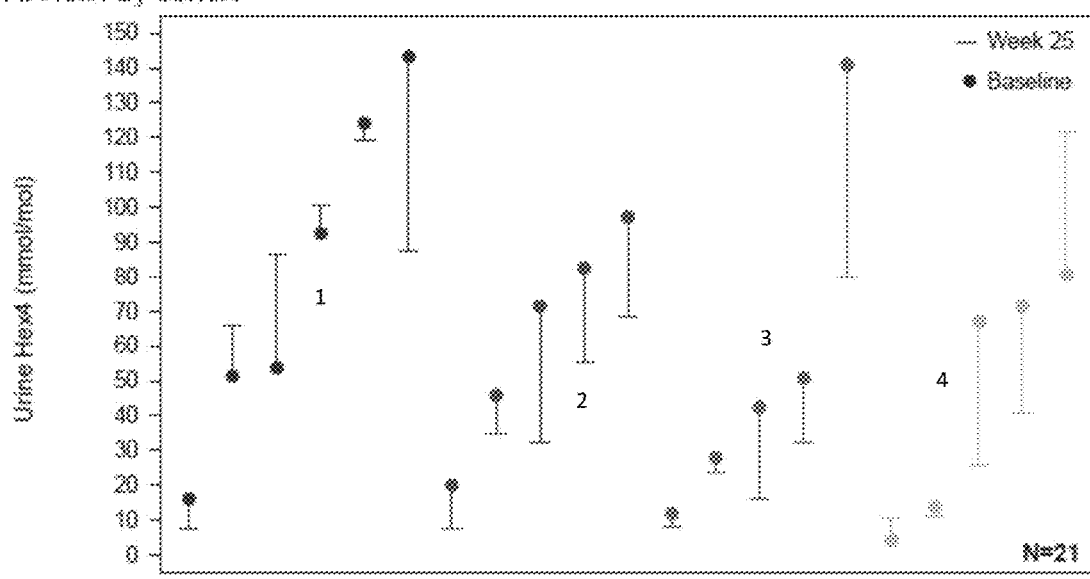
FIGS. 8A-8D show change from baseline to Week 25 in hexose tetrasaccharide (Hex4) ordered by cohort (FIG. 8A) and baseline value (FIG. 8B), and in creatine kinase (CK) ordered by cohort (FIG. 8C) and baseline value (FIG. 8D). 1: Cohort 1 (Avalglucosidase alfa 20 mg/kg qow); 2: Cohort 2 (Avalglucosidase alfa 40 mg/kg qow); 3: Cohort 3 (Avalglucosidase alfa 40 mg/kg qow); and 4: Cohort 3 (Alglucosidase alfa 20 mg/kg qow to 40 mg/kg weekly).
Figure 8B:
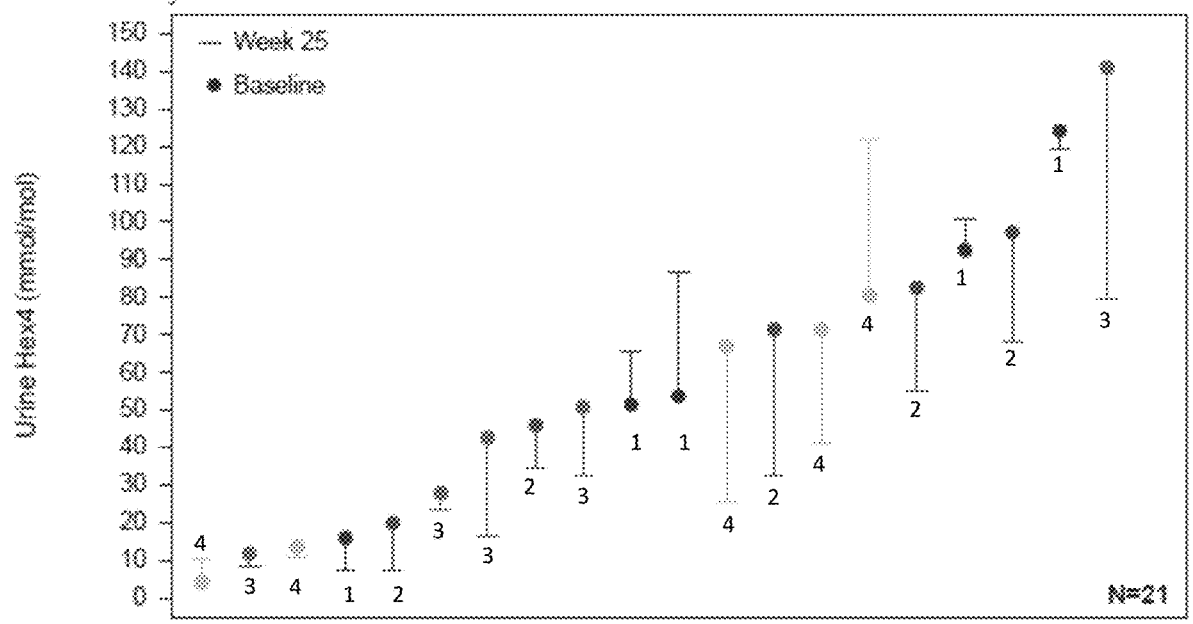
Figure 8C:
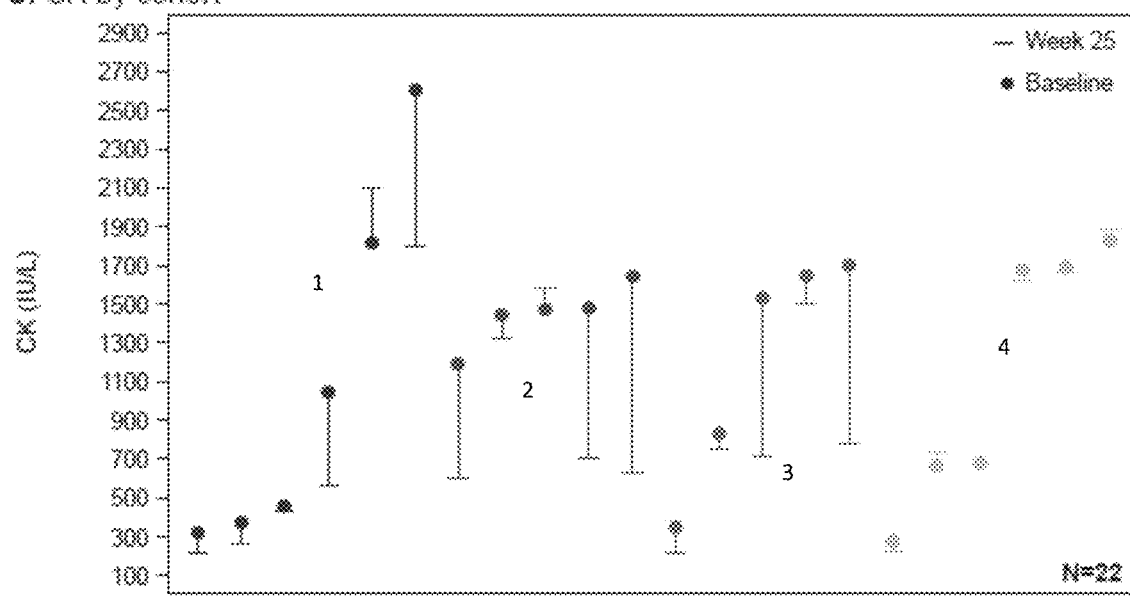
Figure 8D:
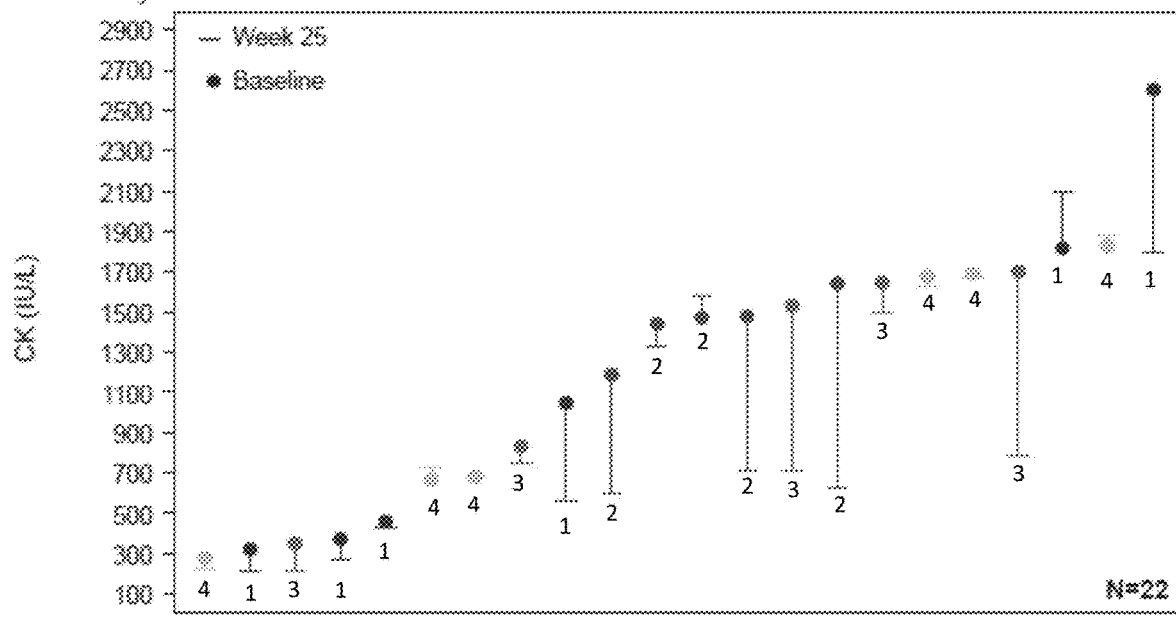
Figure 9A:
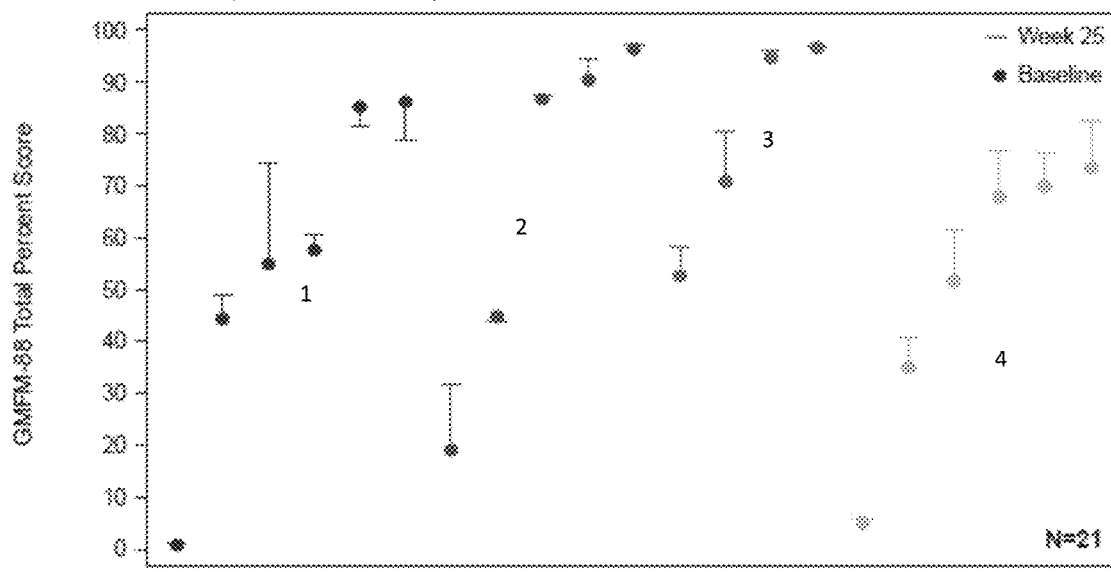
FIGS. 9A-9D show change from baseline to Week 25 in Growth Motor Function Measure-88 items (GMFM-88) ordered by cohort (FIG. 9A) and baseline value (FIG. 9B), and in Quick Motor Function Test (QMFT) ordered by cohort (FIG. 9C) and baseline value (FIG. 9D). 1: Cohort 1 (Avalglucosidase alfa 20 mg/kg qow); 2: Cohort 2 (Avalglucosidase alfa 40 mg/kg qow); 3: Cohort 3 (Avalglucosidase alfa 40 mg/kg qow); and 4: Cohort 3 (Alglucosidase alfa 20 mg/kg qow to 40 mg/kg weekly).
Figure 9B:
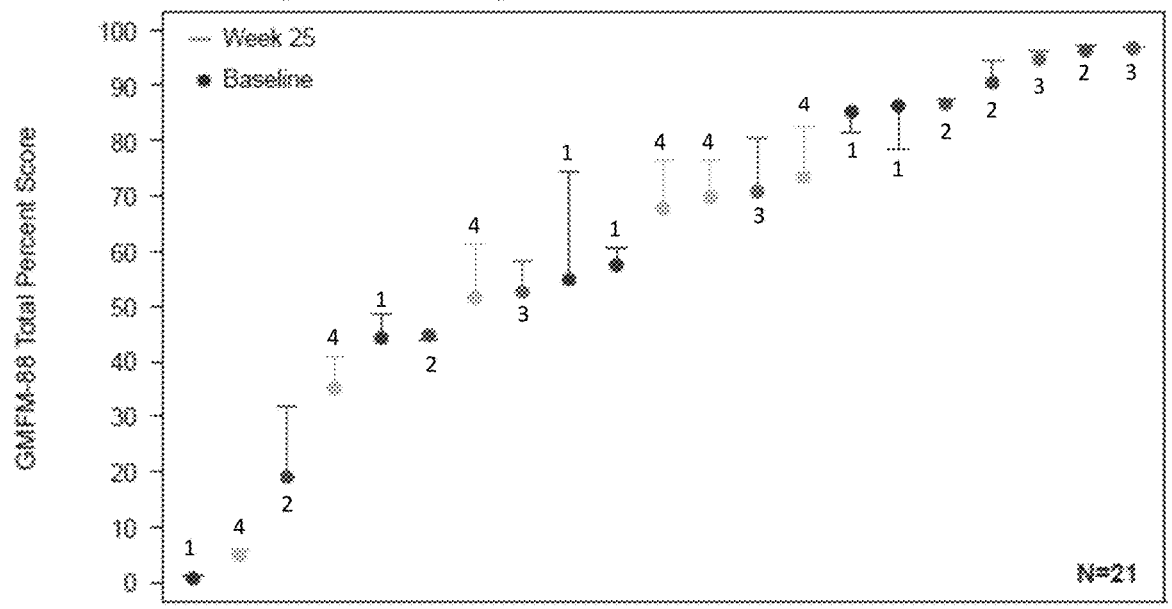
Figure 9C:
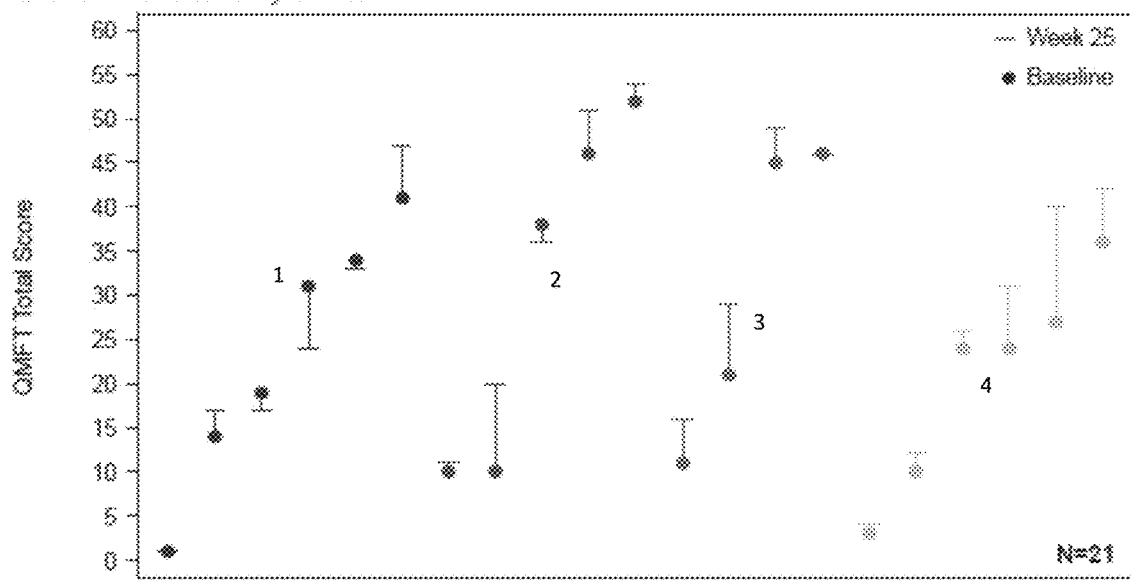
Figure 9D:
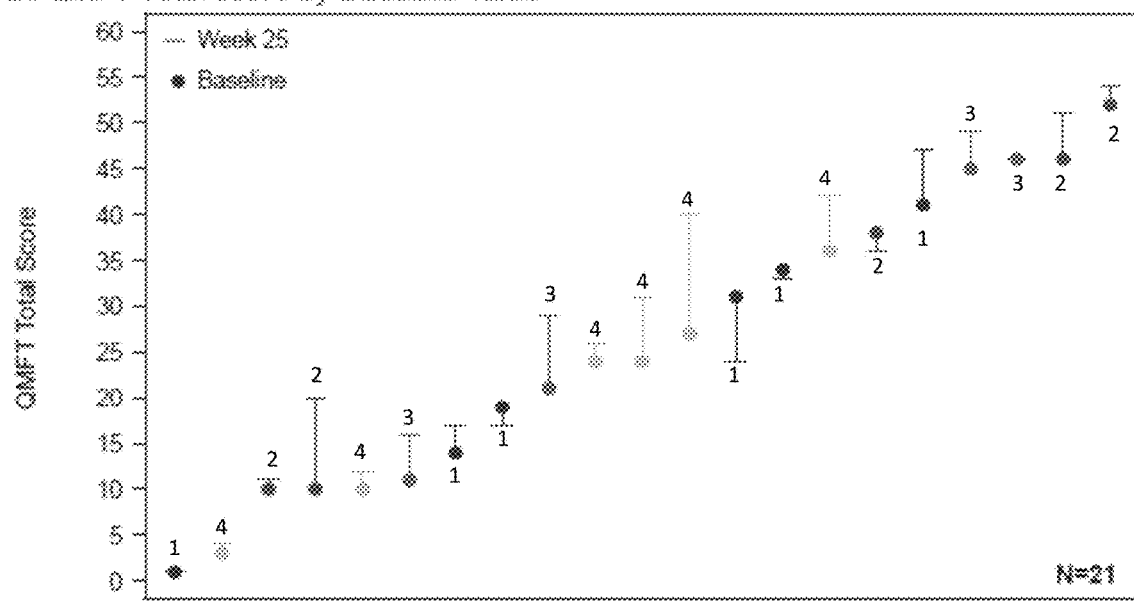

FIGS. 8A-8D show individual responses in different cohorts as measured by Pompe disease burden biomarkers: (1) hexose tetrasaccharide (Hex4) level and (2) creatine kinase (CK) levels. Hex4 decrease from Baseline to Week 25 was largest in participants treated with avalglucosidase alfa 40 mg/kg qow with Baseline values >40 mmol/mol, while changes were more variable for those treated with alglucosidase alfa and avalglucosidase alfa 20 mg/kg qow (FIGS. 8A-8B). CK decrease from Baseline to Week 25 appears to be observed primarily in participants with Baseline levels >900 IU/L, and tended to decrease in participants treated with avalglucosidase alfa and remained stable in those treated with alglucosidase alfa (FIGS. 8C-8D).

FIGS. 9A-9D show individual responses in different cohorts as measured by motor function parameters, including GMFM-88 and QMFT. GMFM-88 and Quick Motor Function Test (QMFT) appear to have the greatest improvements with a Baseline score between 20-70% (on a scale of 0-100%) and 10-45 (on a scale of 0-64), respectively. Lower or higher functioning participants remain stable or tend to decrease (FIGS. 9A-9D).

Figure 10A:
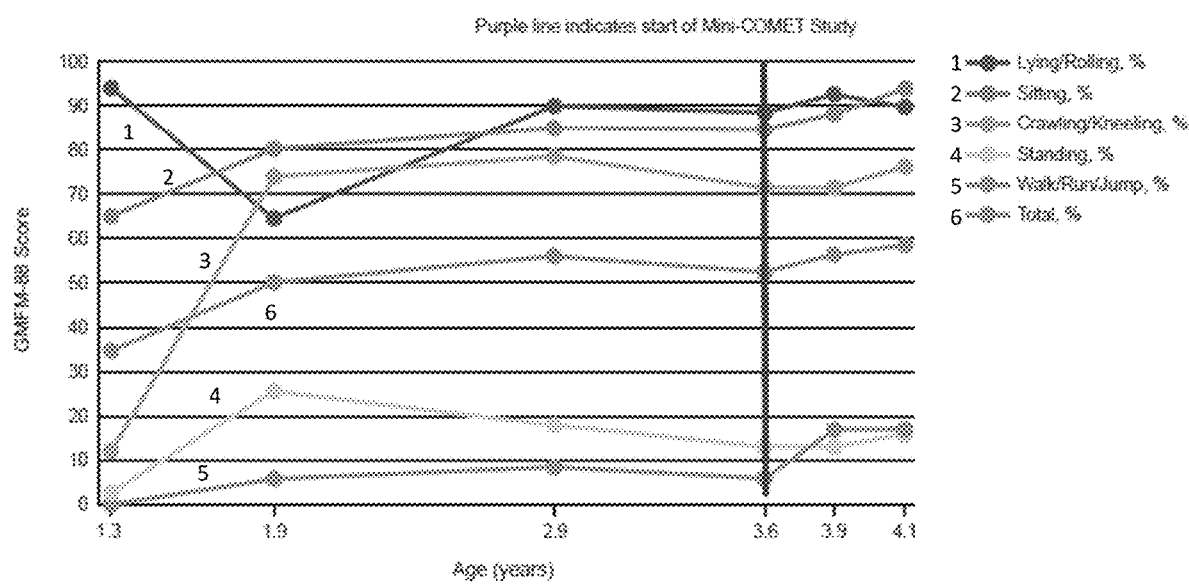
FIGS. 10A-10C show Gross Motor Function Measure-88 items (GMFM-88) performance as documented in retrospective chart data and after start of avalglucosidase alfa treatment for individual participates of three case studies.
Figure 10B:
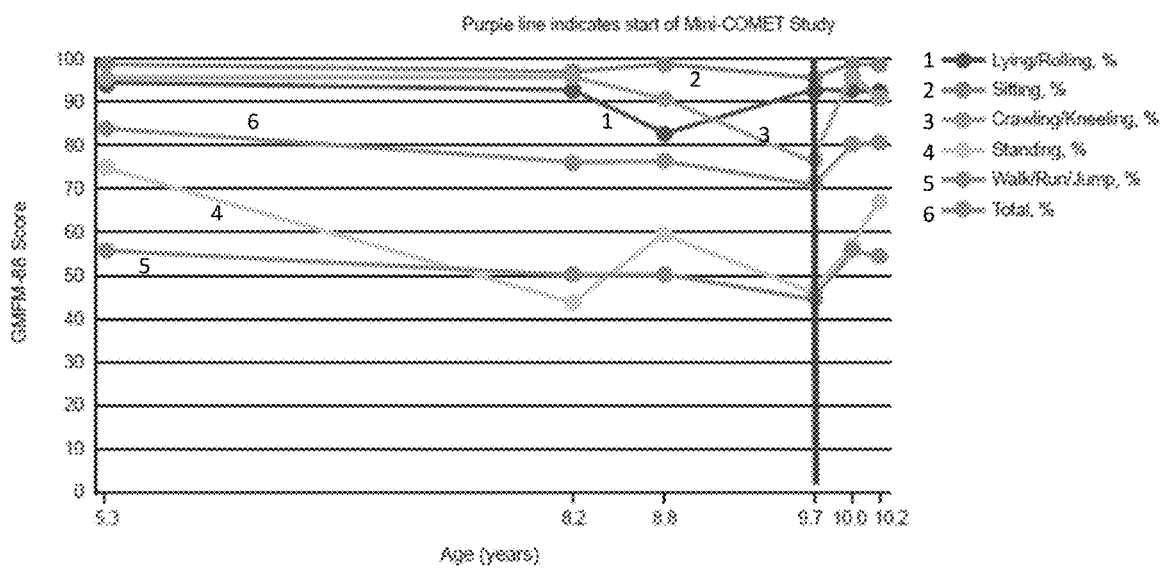
Figure 10C:
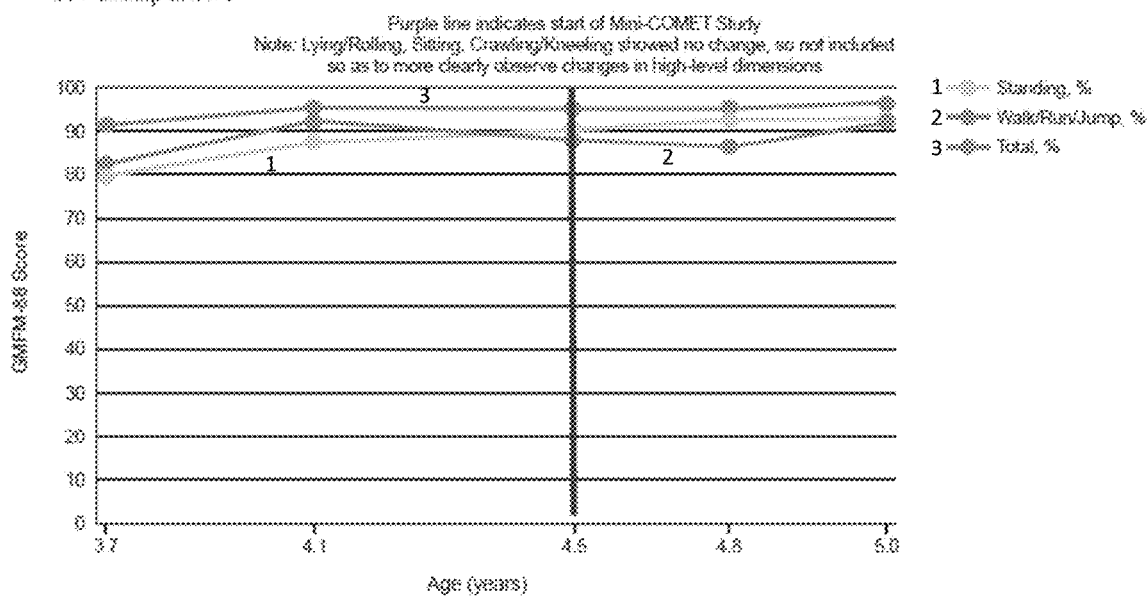

In those participants where GMFM-88 score was available prior to starting avalglucosidase alfa treatment, consistent improvement in motor function was evidenced after switching from weekly high alglucosidase alfa treatment to avalglucosidase alfa 40 mg/kg qow. Three individual case studies are shown in FIGS. 10A-10C and Table 8 below.

TABLE 8

Case studies

| Participant | Characteristics at enrollment | Biomarker | Baseline | Week 25 | Change Baseline to Week 25 |
|---|---|---|---|---|---|
| #1 | 3.6 years of age Male GMFM-88: plateau GMFCS E&R level III Treatment prior to Mini-COMET: alglucosidase alfa 42.6 mg/kg weekly | Hex4, mmol/mol CK, IU/L | 50.83 1704 | 32.34 779 | −18.49 −925 |
| #2 | 9.7 years of age Female GMFM-88: decline GMFCS E&R level II Treatment prior to Mini-COMET: alglucosidase alfa 35 mg/kg weekly | Hex4, mmol/mol CK, IU/L | 27.73 829 | 23.53 748 | −4.2 −81 |
| #3 | 4.5 years of age Female GMFM-88: plateau GMFCS E&R level I Treatment prior to Mini-COMET: alglucosidase alfa 25 mg/kg weekly | Hex4, mmol/mol CK, IU/L | 11.94 347 | 8.29 213 | −3.65 −134 |

Figure 11A:
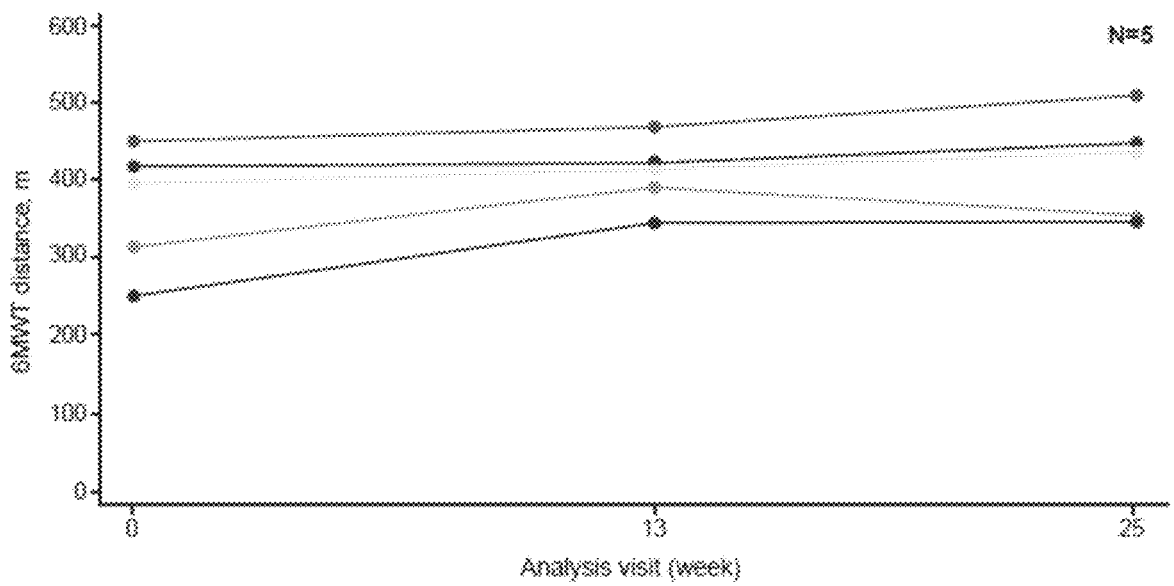
FIGS. 11A-11B show 6-minute walk test (6MWT) distance at baseline and Week 13 and 25 in ambulatory participants >6 years of age at baseline.
Figure 11B:
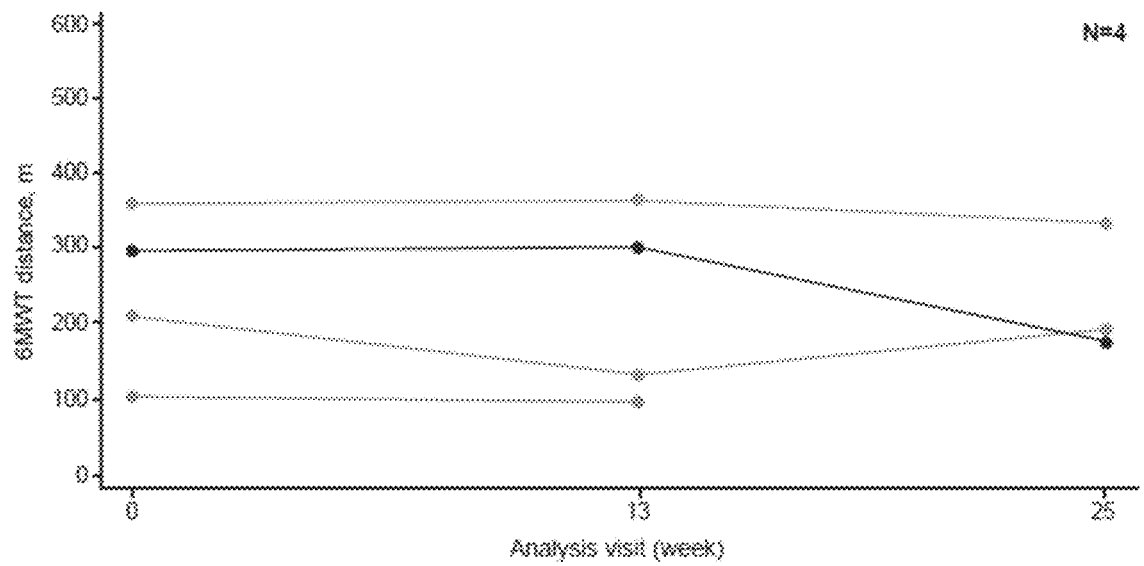

6-Minute walk test (6MWT) distance in ambulatory participants >6 years of age at Baseline improved for all those receiving avalglucosidase alfa 40 mg/kg qow in Cohorts 2 and 3 (FIG. 11A), while participants in Cohort 1 receiving a lower dose of avalglucosidase alfa (20 mg/kg qow) and in the Cohort 3 alglucosidase alfa arm (dose range, 20 mg/kg qow to 40 mg/kg weekly) were stable or declined during the first 25 weeks of treatment (FIG. 11B).

Limited data on pulmonary function testing were available based on age-related limitations with ability to reliably undergo testing. 5 participants were receiving ventilation at Baseline, and few changes without respiratory decline were observed.

CONCLUSIONS

Patients' demographics and characteristics at baseline were comparable across the three cohorts and treatment arms except for age (the mean age was younger in Cohort 3 patients randomized to alglucosidase alfa). Functional levels at baseline were heterogeneous across all patients, with less severe motor dysfunction in Cohort 3.

No patient discontinued in the primary analysis period or up to the cut-off date. Further, there were no deaths, and no treatment-related serious adverse events.

There was a favorable safety and immunogenicity profile. Avalglucosidase alfa was generally safe and well tolerated at 20 and 40 mg/kg every 2 weeks in severely affected IOPD patients with incomplete treatment response to alglucosidase alfa who were previously treated at dose regimens ranging from 20 mg/kg every 2 weeks to 40 mg/kg weekly. Disease biomarkers and exploratory efficacy assessments show trends of improvement in the majority of study participants.

There was a trend for a more pronounced creatine kinase (and HEX4) decrease in patients receiving 40 mg/kg avalglucosidase alfa. There was high inter-individual variability.

There was also a trend for improvement in eyelid position was observed in participants receiving avalglucosidase alfa 40 mg/kg qow compared with stabilization or decline in participants receiving avalglucosidase alfa 20 mg/kg qow or alglucosidase alfa at doses ranging from 20 mg/kg qow to 40 mg/kg weekly. This effect was more pronounced for the Interpalpebral Fissure Distance than for either the Margin Reflex Distance-1 or Margin Pupil Distance. These data further support the more potent effect of avalglucosidase alfa 40 mg/kg qow on a clinically meaningful outcome measure (i.e., the prevention of worsening of ptosis, ultimately translating into decreased risk of amblyopia or need for surgical intervention) in long-term survivors with IOPD.

The majority of patients (14/16 patients treated with avalglucosidase alfa, 6/6 patients treated with alglucosidase alfa) experienced stabilization or improvement of entry criteria of clinical decline/suboptimal response.

Due to the heterogeneous baseline functional levels of the patient cohorts, patient level analyses clarify the effect of avalglucosidase alfa. Analyses are performed to account for heterogeneous functional levels at baseline, as well as differences in age at diagnosis and study entry, previous alglucosidase alfa treatment, and sex balance across patients in the three cohorts and treatment arms.

The participant-level analyses confirm that avalglucosidase alfa at 20 and 40 mg/kg qow appears to improve or better stabilize symptoms of Pompe disease compared with alglucosidase alfa (20 mg/kg qow to 40 mg/kg weekly) with regard to pharmacodynamic disease biomarkers, motor outcomes, respiratory parameters and eyelid measures. The highest dose of avalglucosidase alfa tested, 40 mg/kg qow, appears to afford additional benefits in meaningful outcome measures, while maintaining a favorable safety profile and acceptable immunogenicity.

These data support the positive clinical impact with use of avalglucosidase alfa in patients with IOPD, the most severely affected population of patients with Pompe disease Example 2. Avalglucosidase Alfa in Treatment-Naïve Infantile-Onset Pompe Disease Clinical Trial The following example describes a Phase 3, open-label, multinational, multicenter, intravenous infusion study of the efficacy, safety, pharmacokinetics, and pharmacodynamics of avalglucosidase alfa in treatment-naïve pediatric infantile-onset Pompe disease patients less than or equal to 6 months of age.

A. Study Design

Objectives

The primary objective of the study is to determine the effect of avalglucosidase alfa treatment on survival and invasive ventilator-free survival of infantile-onset Pompe disease (IOPD) patients less than or equal to 6 months of age after 52 weeks of treatment. The secondary objectives of the study are to determine the effect of avalglucosidase alfa treatment on survival and invasive ventilator-free survival at 12 and 18 months of age, as well the changes in left ventricular mass Z-score (LVM Z-score), Alberta Infant Motor Scale (AIMS) score, body length, body weight, and head circumference percentiles, and urinary Hex4 levels at Week 52 of the study. Other secondary objectives of the study are to determine safety, tolerability, and immunogenicity of avalglucosidase alfa, and to determine the pharmacokinetic (PK) profile at Week 12 and Week 52.

Methodology

Patients are included in a single, experimental arm, who receive an avalglucosidase alfa intravenous (IV) infusion every two weeks. Primary endpoint data is collected at 52 weeks, prior to completion of the study.

Diagnosis and Criteria for Inclusion and Exclusion

Included patients must have a confirmed diagnosis of infantile-onset Pompe disease, and be less than or equal to 6 months of age.

Inclusion criteria for the study are as follows:

The patient has a confirmed diagnosis of infantile-onset Pompe disease defined as: (1) the presence of two lysosomal acid α-glucosidase (GAA) pathogenic variants and a documented GAA deficiency from blood, skin, or muscle tissue, or (2) the presence of one GAA pathogenic variant and a documented GAA deficiency from blood, skin and muscle tissue in two separate samples (from either two different tissues or from the same tissue but at two different sampling dates).

The patient has an established cross-reactive immunological material (CRIM) status available prior to enrollment. This may be provided by historical CRIM test results, prediction of CRIM based on genotyping, or testing at screening by a Clinical Laboratory Improvement Amendments (CLIA) or other appropriately certified laboratory.

The patient has cardiomyopathy at the time of diagnosis; i.e. left ventricular mass index (LVMI) equivalent to mean age-specific LVMI plus 1 standard deviation for participants diagnosed by newborn screening or sibling screening, or plus 2 standard deviations for participants diagnosed by clinical evaluation.

The patient's parents or legally authorized representative(s) are capable of giving signed informed consent.

Exclusion criteria for the study are as follows:

The patient has symptoms of respiratory insufficiency, or any ventilation use (invasive or noninvasive) at the time of enrollment.

The patient has a major congenital abnormality.

The patient has a clinically significant organic disease (with the exception of symptoms relating to Pompe disease).

The patient has received enzyme-replacement therapy (ERT) with recombinant human acid α glucosidase (rhGAA) from any source.

The patient was previously been treated in any clinical trial of avalglucosidase alfa.

The patient is judged by the Investigator to be not suitable for participation, for whatever the reason, including medical or clinical conditions, or the patient is potentially at risk of noncompliance to study procedures.

Primary and Main Secondary Key Endpoints

The primary endpoint of the study is the proportion of patients who are alive and free of invasive ventilation at Week 52.

Secondary endpoints for the study include the following evaluations at Week 52: the proportion of patients who are alive and free of invasive ventilation at 12 and 18 months of age; the proportion of participants who are alive at Week 52; the proportion of patients who are alive at 12 and 18 months of age; and the proportion of patients who are free of ventilator use and free of supplemental oxygen use at Week 52.

The secondary endpoints also include the following evaluations at Week 52: assessment of treatment-emergent adverse effects (TEAE), including infusion associated reactions; a physical examination; clinical laboratory evaluations; vital sign measurements; a 12-lead electrocardiogram (ECG); and immunogenicity assessments.

Other secondary endpoints include a change in the following parameters, from baseline to Week 52: left ventricular mass (LMV) Z-score, Alberta Infant Motor Scale (AIMS) score, body growth Z-scores, urinary Hex4, and body length, body weight and head circumference percentiles.

Additionally, plasma concentrations of acid α glucosidase (GAA) at day 1, week 12 and week 52 are assessed.

Duration of the Study Period

Patients are treated for 52 weeks for the primary analysis period and continue to receive treatment in the subsequent 52-week study extended treatment period. This is followed by an extended long-term treatment period up to 104 weeks plus 4-week follow-up period for a total study duration of up to 4.08 years. This duration may be variable by country, but lasts until avalglucosidase alfa is approved in the patient's country or up to 4.08 years, whichever comes first.

Avalglucosidase Alfa Formulation

Avalglucosidase alfa is formulated as a sterile lyophilized powder. It is reconstituted prior to administration by IV infusion.

What is claimed is:

1. A method for treating an infantile-onset Pompe disease (IOPD), comprising administering to a human individual in need thereof a pharmaceutical composition comprising an oligosaccharide-protein conjugate and a pharmaceutically acceptable carrier, wherein the oligosaccharide-protein conjugate is avalglucosidase alfa;
wherein the pharmaceutical composition is administered at a dose of about 20 mg/kg to about 40 mg/kg;
wherein the pharmaceutical composition is administered to the individual for at least about 25 weeks; and
wherein creatine kinase (CK) level of the individual decreases by at least about 100 IU/L when measured after at least about 25 weeks of treatment.

2. The method of claim 1, wherein the pharmaceutical composition is administered at a dose of about 20 mg/kg.

3. The method of claim 1, wherein the pharmaceutical composition is administered to the individual once every two weeks.

4. The method of claim 1, wherein the pharmaceutical composition is administered intravenously.

5. The method of claim of claim 1, wherein the individual has cardiomyopathy at the time of diagnosis in the first year of life.

6. The method of claim 1, wherein the individual is 18 years old or younger.

7. The method of claim 1, wherein the individual has received at least 6 months of treatment with a recombinant GAA.

8. The method of claim 7, wherein:
(i) the individual shows clinical decline after treatment with the recombinant GAA, wherein the clinical decline is determined by assessing one or more parameters selected from the group consisting of respiratory functions, motor skills and cardiac parameters; or
(ii) the individual has suboptimal clinical response to treatment with the recombinant GAA, wherein the clinical response is determined by assessing one or more parameters selected from the group consisting of respiratory functions, motor skills and cardiac parameters.

9. The method of claim 1, wherein the individual has not received treatment with a recombinant GAA.

10. The method of claim 7, wherein the recombinant GAA is alglucosidase alfa.

11. The method of claim 1, wherein the individual is cross-reactive immunologic material (CRIM)-negative.

12. The method of claim 1, wherein urinary hexose tetrasaccharide (Hex4) level of the individual decreases by at least about 10 mmol/mol when measured after at least about 25 weeks of treatment.

13. The method of claim 1, wherein Gross Motor Function Measure (GMFM-88) score of the individual increases by at least 5% when measured after at least about 25 weeks of treatment.

14. The method of claim 1, wherein the individual shows improvement or stabilization of one or more parameters selected from the group consisting of respiratory functions, motor skills, cardiac parameters and eyelid positions.

15. The method of claim 14, wherein the improvement or stabilization is assessed based on one or more parameters selected from the group consisting of Alberta Infant Motor Scale (AIMS) score, Pompe-Pediatric Evaluation of Disability Inventory (PEDI) functional skills scale, Echocardiographic (ECHO)-left ventricular mass (LVM) Z-score, ECHO LVMI score, Gross Motor Function Classification System-Expanded and Revised (GMFCS-E&R) score, Quick Motor Function Test, 6 Minute Walk test (6MWT), interpalpebral fissure distance (IPFD), margin reflex distance-1 (MRD-1), margin pupil distance (MPD), onset of ptosis, and use of respiratory support.

* * * * *